(12) United States Patent
Lee et al.

(10) Patent No.: US 12,344,709 B2
(45) Date of Patent: Jul. 1, 2025

(54) CATIONIC POLYMER AND USE FOR BIOMOLECULE DELIVERY

(71) Applicant: GenEdit Inc., South San Francisco, CA (US)

(72) Inventors: Kunwoo Lee, Berkeley, CA (US); Santanu Maity, Berkeley, CA (US)

(73) Assignee: GenEdit Inc., South San Francisco, CA (US)

(*) Notice: Subject to any disclaimer, the term of this patent is extended or adjusted under 35 U.S.C. 154(b) by 990 days.

(21) Appl. No.: 17/051,157

(22) PCT Filed: Apr. 29, 2019

(86) PCT No.: PCT/US2019/029746
§ 371 (c)(1),
(2) Date: Oct. 27, 2020

(87) PCT Pub. No.: WO2019/210326
PCT Pub. Date: Oct. 31, 2019

(65) Prior Publication Data
US 2021/0238347 A1  Aug. 5, 2021

Related U.S. Application Data

(60) Provisional application No. 62/750,097, filed on Oct. 24, 2018, provisional application No. 62/663,985, filed on Apr. 27, 2018.

(51) Int. Cl.
*C08G 69/10* (2006.01)
*A61K 9/51* (2006.01)
(Continued)

(52) U.S. Cl.
CPC ............ *C08G 69/10* (2013.01); *A61K 9/5146* (2013.01); *A61K 47/10* (2013.01);
(Continued)

(58) Field of Classification Search
None
See application file for complete search history.

(56) References Cited

U.S. PATENT DOCUMENTS 5,858,278 A   1/1999  Itoh et al.
7,001,891 B1  2/2006  Domb
(Continued)

FOREIGN PATENT DOCUMENTS

CN   112334510 A   2/2021
EA       016911 B1   8/2012
(Continued)

OTHER PUBLICATIONS

PCT/US2019/029746 International Search and Written Opinion Issued on Nov. 18, 2019.
(Continued)

*Primary Examiner* — Tae H Yoon
(74) *Attorney, Agent, or Firm* — Leydig, Voit & Mayer, Ltd.

(57) ABSTRACT

Provided is a polymer comprising a structure of Formula (1): (1) and a method of preparing said polymer. Also provided is a composition comprising the polymer and a nucleic acid and/or polypeptide, and a method of delivering a nucleic acid and/or polypeptide to a cell.

(Continued)

-continued

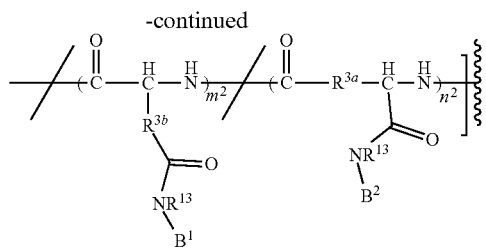

28 Claims, 18 Drawing Sheets

Specification includes a Sequence Listing.

(51) Int. Cl.
A61K 47/10 (2017.01)
A61K 47/24 (2006.01)
A61K 47/64 (2017.01)
A61K 47/69 (2017.01)
C08G 69/04 (2006.01)
C08G 69/48 (2006.01)

(52) U.S. Cl.
CPC ...... *A61K 47/6455* (2017.08); *A61K 47/6931* (2017.08); *C08G 69/04* (2013.01); *C08G 69/48* (2013.01)

(56) References Cited

U.S. PATENT DOCUMENTS

| | | |
|---|---|---|
| 7,557,110 B2 | 7/2009 | Kataoka et al. |
| 7,719,796 B2 | 5/2010 | Takahashi et al. |
| 7,780,957 B2 | 8/2010 | Kataoka et al. |
| 7,829,657 B2 | 11/2010 | Kataoka et al. |
| 8,318,205 B2 | 11/2012 | Kataoka et al. |
| 8,450,282 B2 | 5/2013 | Kataoka et al. |
| 8,546,487 B2 | 10/2013 | Kataoka et al. |
| 8,592,385 B2 | 11/2013 | Kataoka et al. |
| 8,716,217 B2 | 5/2014 | Chan et al. |
| 8,791,086 B2 | 7/2014 | Kataoka et al. |
| 8,853,167 B2 | 10/2014 | Kato et al. |
| 8,906,503 B2 | 12/2014 | Kataoka et al. |
| 9,051,354 B2 | 6/2015 | Kataoka et al. |
| 9,114,177 B2 | 8/2015 | Kataoka et al. |
| 9,278,075 B2 | 3/2016 | Kataoka et al. |
| 9,303,122 B2 | 4/2016 | Kataoka et al. |
| 9,314,529 B2 | 4/2016 | Kataoka et al. |
| 9,750,687 B2 | 9/2017 | Kataoka et al. |
| 9,782,358 B2 | 10/2017 | Kataoka et al. |
| 12,116,458 B2 | 10/2024 | Lee et al. |
| 2006/0189632 A1 | 8/2006 | Kataoka et al. |
| 2007/0002494 A1 | 1/2007 | Takahashi et al. |
| 2007/0059271 A1 | 3/2007 | Kataoka et al. |
| 2008/0249049 A1 | 10/2008 | Kataoka et al. |
| 2009/0258416 A1 | 10/2009 | Kataoka et al. |
| 2010/0137512 A1 | 6/2010 | Kataoka et al. |
| 2011/0060123 A1 | 3/2011 | Kataoka et al. |
| 2011/0256227 A1 | 10/2011 | Mirosevich et al. |
| 2012/0046453 A1 | 2/2012 | Kataoka et al. |
| 2012/0053295 A1 | 3/2012 | Kazunori et al. |
| 2012/0064346 A1 | 3/2012 | Kataoka et al. |
| 2012/0149649 A1 | 6/2012 | Kato et al. |
| 2012/0177594 A1 | 7/2012 | Kataoka et al. |
| 2012/0196810 A1 | 8/2012 | Kataoka et al. |
| 2012/0237565 A1 | 9/2012 | Mirosevich et al. |
| 2013/0109743 A1 | 5/2013 | Kataoka et al. |
| 2013/0202711 A1 | 8/2013 | Kataoka et al. |
| 2014/0017328 A1 | 1/2014 | Kataoka et al. |
| 2015/0051347 A1 | 2/2015 | Kataoka et al. |
| 2015/0141575 A1 | 5/2015 | Kataoka et al. |
| 2016/0051484 A1 | 2/2016 | Kataoka et al. |
| 2016/0106855 A1 | 4/2016 | Ziv |
| 2016/0184457 A1 | 6/2016 | Kataoka et al. |
| 2016/0230189 A1* | 8/2016 | Kotha ..................... A61P 19/10 |
| 2017/0173182 A1 | 6/2017 | Kataoka et al. |
| 2017/0183389 A1 | 6/2017 | Itaka et al. |
| 2018/0185281 A1 | 1/2018 | Kataoka et al. |
| 2021/0238347 A1 | 8/2021 | Tavernier et al. |
| 2021/0340322 A1 | 11/2021 | Kim et al. |
| 2022/0340711 A1 | 10/2022 | Lee et al. |
| 2022/0340712 A1 | 10/2022 | Lee et al. |
| 2023/0147779 A1 | 5/2023 | Lee et al. |
| 2024/0285781 A1 | 8/2024 | Lee et al. |

FOREIGN PATENT DOCUMENTS

| | | | |
|---|---|---|---|
| EP | | 2397487 A1 | 12/2011 |
| EP | | 2399948 A1 | 12/2011 |
| JP | | 2003-505473 A | 2/2003 |
| JP | | 2010-285460 A | 12/2010 |
| JP | | 2011-026219 A | 2/2011 |
| JP | | 2011-173802 A | 9/2011 |
| WO | | 1999/061512 A1 | 12/1999 |
| WO | | 2000/067142 A1 | 11/2000 |
| WO | | 2001/007486 A1 | 2/2001 |
| WO | | 2006/085664 A1 | 6/2008 |
| WO | | 2007/099660 A1 | 7/2009 |
| WO | | 2010/093036 A1 | 8/2010 |
| WO | | 2011/105402 A1 | 1/2011 |
| WO | WO 2017/002979 A1 | | 1/2017 |
| WO | | 2017/053312 A1 | 3/2017 |
| WO | | 2017/056095 A1 | 4/2017 |
| WO | WO 2017/192512 A2 * | | 11/2017 |
| WO | WO 2018/053795 A1 | | 3/2018 |
| WO | | 2018/094356 A2 | 5/2018 |
| WO | | 2019/210326 A2 | 12/2019 |
| WO | | 2020/086910 A1 | 4/2020 |
| WO | | 2020/219776 A1 | 10/2020 |
| WO | | 2020/243370 A1 | 12/2020 |
| WO | | 2021/217082 A1 | 10/2021 |
| WO | | 2022/261561 A1 | 12/2022 |

OTHER PUBLICATIONS

Kim H. J. et al., "Introduction of stearoyl moieties into a biocompatible cationic polyaspartamide derivative, PAsp(DET), with endosomal escaping function for enhanced siRNA-mediated gene knockdown", *Journal of Controlled Release*, vol. 145, No. 2, pp. 141-148 (2010) (abstract only).

Maier, Kevin et al., "Acid-Labile Traceless Click Linker for Protein Transduction," *Journal of the American Chemical Society*, 134, pp. 10169-10173 (2012).

Rozema, David B. et al., "Endosomolysis by Masking of a Membrane-Active Agent (EMMA) for Cytoplasmic Release of Macromolecules," *Bioconjugate Chem*, 14, pp. 51-57 (2003).

Tangsangasaksri, Montira et al., "siRNA-Loaded Polyion Complex Micelle Decorated with Charge-Conversional Polymer Tuned to Undergo Stepwise Response to Intra-Tumoral and Intra-Endosomal pHs for Exerting Enhanced RNAi Efficacy," *BioMacromolecules*, 17, pp. 246-255 (2016).

Takemoto, Hiroyasu et al., "Acid pH-Responsive siRNA Conjugate for Reversible Carrier Stability and Accelerated Endosomal Escape with Reduced IFNα-Associated Immune Response", *Angew. Chem. Int. Ed*, 52, pp. 6218-6221 2013.

Foster, Suzanne et al., "Intracellular Delivery of a Protein Antigen with an Endosomal-Releasing Polymer Enhances CD8 T-Cell Production and Prophylactic Vaccine Efficacy," *Bioconjug Chem*, 21(12) pp. 2205-2212 (2010).

Fu, Ailing et al., "Promises and Pitfalls of Intracellular Delivery of Proteins," *Bioconjugate Chemistry*, 25, pp. 1602-1608 (2014).

Lackey, Chantal A. et al., "A biomimetic pH-Responsive Polymer Directs Endosomal Release and Intracellular Delivery of an Endocytosed Antibody Complex," *Bioconjugate Chemistry*, 13 (5), pp. 996-1001 (2002) (abstract only).

(56) References Cited

OTHER PUBLICATIONS

Nauka, PC et al., "Enhancing Conjugation Yield of Brush Polymer-Protein Conjugates by Increasing Linker Length at the Polymer End-Group," *Polym Chem*, 7 (13), pp. 2352-2357 (2016).

Uchida, Hirokuni et al, "Modulated Protonation of Side Chain Aminoethylene Repeats in N-Substituted Polyaspartamides Promotes mRNA Transfection," *Journal of the American Chemical Society*, 136, pp. 12396-12405 (2014).

Qi, Yizhi et al., "Protein-Polymer Conjungation-Moving Beyond PEGylation," *Curr Opin Chem Biol*, 28, pp. 181-193 (2015).

Tian, Li et al., "Endosomolytic reducible polymeric electrolytes for cytosolic protein delivery," *Biomacromolecules*, 14(8), pp. 2570-2581 (2013).

Van Dijk-Wolthuis, WN et al., "A versatile method for the conjugation of proteins and peptides to poly[2-(dimethylamino)ethyl methacrylate]," *Bioconjug Chem*, 10(4), pp. 687-692 (1999) (abstract only).

Song et al., "Synthetic polypeptides: from polymer design to supramolecular assembly and biomedical application," *Chem. Soc Rev.*, 25, vol. 46, No. 21, pp. 6570-6599 (2017).

U.S. Appl. No. 17/287,978, filed Apr. 22, 2021.
U.S. Appl. No. 17/605,981, filed Oct. 22, 2021.
U.S. Appl. No. 17/614,307, filed Nov. 24, 2021.
U.S. Appl. No. 17/921,016, filed Oct. 24, 2022.
U.S. Appl. No. 18/568,539, filed Dec. 8, 2023.

Kim et al., "Fine-Tuning of Hydrophobicity in Amphiphilic Polyaspartamide Derivatives for Rapid and Transient Expression of Messenger RNA Directed Toward Genome Engineering in Brain," *ACS Central Science*, 5(11): 1866-1875 (2019).

Liu et al., "Novel biodegradable lipid nano complex for siRNA delivery significantly improving the chemosensitivity of human colon cancer stem cells to paclitaxel," *Journal of Controlled Release*, 140(3): 277-283 (2009).

Miyata et al., "Polyplexes from Poly (aspartamide) Bearing 1,2-Diaminoethane Side Chains Induce pH-Selective, Endosomal Membrane Destabilization with Amplified Transfection and Negligible Cytotoxicity," *J. Am. Chem. Soc.*, 130: 16287-16294 (2008).

Jongmin Yum et al., "Fine-tuning of polyaspartamide derivatives with alicyclic moieties for systemic mRNA delivery," *Journal of Controlled Release*, 342(4): 148-156 (2022).

\* cited by examiner

FIG. 1

Francisella tularensis subsp. novicida U112 Cpf1

```
   1 msiyqefvnk yslsktlrfe lipqgktlen ikarglildd ekrakdykka kqiidkyhqf
  61 fieeilssvc isedllqnys dvyfklkksd ddnlqkdfks akdtikkqis eyikdsekfk
 121 nlfnqnlida kkgqesdlil wlkqskdngi elfkansdit dideal eiik sfkgwttyfk
 181 gfhenrknvy ssndiptsii yrivddnlpk flenkakyes lkdkapeain yeqikkdlae
 241 eltfdidykt sevnqrvfsl devfeianfn nylnqsgitk fntiiggkfv ngentkrkgi
 301 neyinlysqq indktlkkyk msvlfkqils dtesksfvid kleddsdvvt tmqsfyeqia
 361 afktveeksi ketlsllfdd lkaqkldlsk iyfkndkslt dlsqqvfddy svigtavley
 421 itqqiapknl dnpskkeqel iakktekaky lsletiklal eefnkhrdid kqcrfeeila
 481 nfaaipmifd eiaqnkdnla qisikyqnqg kkdllqasae ddvkaikdll dqtnnllhkl
 541 kifhisqsed kanildkdeh fylvfeecyf elanivplyn kirnyitqkp ysdekfklnf
 601 enstlangwd knkepdntai lfikddkyyl gvmnkknnki fddkaikenk gegykkivyk
 661 llpgankmlp kvffsaksik fynpsedilr irnhsthtkn gspqkgyekf efniedcrkf
 721 idfykqsisk hpewkdfgfr fsdtqrynsi defyrevenq gykltfenis esyidsvvnq
 781 gklylfqiyn kdfsayskgr pnlhtlywka lfdernlqdv vyklngeael fyrkqsipkk
 841 ithpakeaia nknkdnpkke svfeydlikd krftedkfff hcpitinfks sgankfndei
 901 nlllkekand vhilsidrge rhlayytlvd gkgniikqdt fniigndrmk tnyhdklaai
 961 ekdrdsarkd wkkinnikem kegylsqvvh eiaklvieyn aivvfedlnf gfkrgrfkve
1021 kqvyqklekm lieklnylvf kdnefdktgg vlrayqltap fetfkkmgkq tgiiyyvpag
1081 ftskicpvtg fvnqlypkye svsksqeffs kfdkicynld kgyfefsfdy knfgdkaakg
1141 kwtiasfgsr linfrnsdkn hnwdtrevyp tkelekllkd ysieyghgec ikaaicgesd
1201 kkffakltsv lntilqmrns ktgteldyli spvadvngnf fdsrqapknm pqdadangay
1261 higlkglmll grikknqegk klnlvikneе yfefvqnrnn
```

AsCpf1

```
   1 mtqfegftnl yqvsktlrfe lipqgktlkh iqeqgfieed karndhykel kpiidriykt
  61 yadqclqlvq ldwenlsaai dsyrkektee trnalieeqa tyrnaihdyf igrtdnltda
 121 inkrhaeiyk glfkaelfng kvlkqlgtvt ttehenallr sfdkfttyfs gfyenrknvf
 181 saedistaip hrivqdnfpk fkenchiftr litavpslre hfenvkkaig ifvstsieev
 241 fsfpfynqll tqtqidlynq llggisreag tekikglnev lnlaiqknde tahiiaslph
 301 rfiplfkqil sdrntlsfil eefksdeevi qsfckyktll rnenvletae alfnelnsid
 361 lthifishkk letissalcd hwdtlrnaly erriseltgk itksakekvq rslkhedinl
 421 qeiisaagke lseafkqkts eilshahaal dqplpttlkk qeekeilksq ldsllglyhl
 481 ldwfavdesn evdpefsarl tgiklemeps lsfynkarny atkkpysvek fklnfqmptl
 541 asgwdvnkek nngailfvkn glyylgimpk qkgrykalsf eptektsegf dkmyydyfpd
 601 aakmipkcst qlkavtahfq thttpillsn nfiepleitk eiydlnnpek epkkfqtaya
 661 kktgdqkgyr ealckwidft rdflskytkt tsidlsslrp ssqykdlgey yaelnpllyh
 721 isfqriaeke imdavetgkl ylfqiynkdf akghhgkpnl htlywtglfs penlaktsik
 781 lngqaelfyr pksrmkrmah rlgekmlnkk lkdqktpipd tlyqelydyv nhrlshdlsd
 841 earallpnvi tkevsheiik drrftsdkff fhvpitlnyq aanspskfnq rvnaylkehp
 901 etpiigidrg ernliyitvi dstgkileqr slntiqqfdy qkkldnreke rvaarqawsv
 961 vgtikdlkqg ylsqviheiv dlmihyqavv vlenlnfgfk skrtgiaeka vyqqfekmli
1021 dklnclvlkd ypaekvggvl npyqltdqft sfakmgtqsg flfyvpapyt skidpltgfv
1081 dpfvwktikn hesrkhfleg fdflhydvkt gdfilhfkmn rnlsfqrglp gfmpawdivf
1141 eknetqfdak gtpfiagkri vpvienhrft gryrdlypan elialleekg ivfrdgsnil
1201 pkllenddsh aidtmvalir svlqmrnsna atgedyinsp vrdlngvcfd srfqnpewpm
1261 dadangayhi alkgqlllnh lkeskdlklq ngisnqdwla yiqelrn
```

FIG. 16

LbCpf1

AASKLEKFTNCYSLSKTLRFKAIPVGKTQENIDNKRLLVEDEKRAEDYKGVKKLLDRYYL
SFINDVLHSIKLKNLNNYISLFRKKTRTEKENKELENLEINLRKEIAKAFKGAAGYKSLF
KKDIIETILPEAADDKDEIALVNSFNGFTTAFTGFFDNRENMFSEEAKSTSIAFRCINEN
LTRYISNMDIFEKVDAIFDKHEVQEIKEKILNSDYDVEDFFEGEFFNFVLTQEGIDVYNA
IIGGFVTESGEKIKGLNEYINLYNAKTKQALPKFKPLYKQVLSDRESLSFYGEGYTSDEE
VLEVFRNTLNKNSEIFSSIKKLEKLFKNFDEYSSAGIFVKNGPAISTISKDIFGEWNLIR
DKWNAEYDDIHLKKKAVVTEKYEDDRRKSFKKIGSFSLEQLQEYADADLSVVEKLKEIII
QKVDEIYKVYGSSEKLFDADFVLEKSLKKNDAVVAIMKDLLDSVKSFENYIKAFFGEGKE
TNRDESFYGDFVLAYDILLKVDHIYDAIRNYVTQKPYSKDKFKLYFQNPQFMGGWDKDKE
TDYRATILRYGSKYYLAIMDKKYAKCLQKIDKDDVNGNYEKINYKLLPGPNKMLPKVFFS
KKWMAYYNPSEDIQKIYKNGTFKKGDMFNLNDCHKLIDFFKDSISRYPKWSNAYDFNFSE
TEKYKDIAGFYREVEEQGYKVSFESASKKEVDKLVEEGKLYMFQIYNKDFSDKSHGTPNL
HTMYFKLLFDENNHGQIRLSGGAELFMRRASLKKEELVVHPANSPIANKNPDNPKKTTTL
SYDVYKDKRFSEDQYELHIPIAINKCPKNIFKINTEVRVLLKHDDNPYVIGIDRGERNLL
YIVVVDGKGNIVEQYSLNEIINNFNGIRIKTDYHSLLDKKEKERFEARQNWTSIENIKEL
KAGYISQVVHKICELVEKYDAVIALEDLNSGFKNSRVKVEKQVYQKFEKMLIDKLNYMVD
KKSNPCATGGALKGYQITNKFESFKSMSTQNGFIFYIPAWLTSKIDPSTGFVNLLKTKYT
SIADSKKFISSFDRIMYVPEEDLFEFALDYKNFSRTDADYIKKWKLYSYGNRIRIFAAAK
KNNVFAWEEVCLTSAYKELFNKYGINYQQGDIRALLCEQSDKAFYSSFMALMSLMLQMRN
SITGRTDVDFLISPVKNSDGIFYDSRNYEAQENAILPKNADANGAYNIARKVLWAIGQFK
KAEDEKLDKVKIAISNKEWLEYAQTSVK

FIG. 17

CATIONIC POLYMER AND USE FOR BIOMOLECULE DELIVERY

CROSS-REFERENCE TO RELATED APPLICATIONS

This application claims the benefit of U.S. Provisional Patent Application No. 62/663,985 filed on Apr. 27, 2018, and U.S. Provisional Patent Application No. 62/750,097 filed on Oct. 24, 2018, the entire disclosures of which are hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 62527 Byte ASCII (Text) file named "512879.TXT," created on Apr. 29, 2019.

BACKGROUND OF THE INVENTION

Peptide, protein, and nucleic based technologies have countless applications to prevent, cure and treat diseases. However, the safe and effective delivery of large molecules (e.g., polypeptides and nucleic acids) to their target tissues remains problematic. Accordingly, there continues to be a need for new compositions and methods useful for delivering therapeutic molecules.

BRIEF SUMMARY OF THE INVENTION

Provided herein is a polymer comprising a structure of Formula 1:

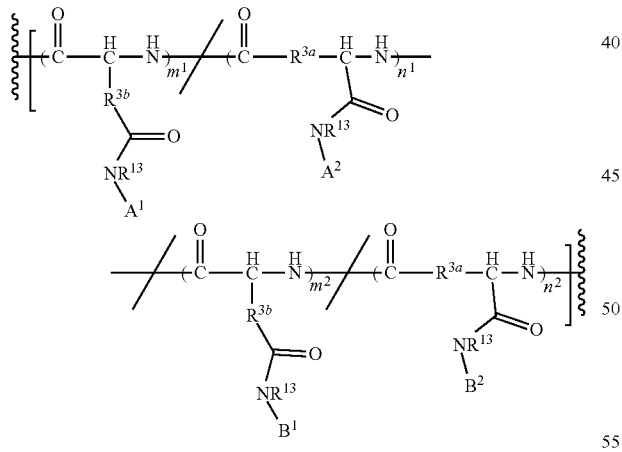

wherein:
each of $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
$R^{3a}$ and $R^{3b}$ are each independently a methylene or ethylene group;
each instance of $R^{13}$ is independently hydrogen or a $C_1$-$C_{12}$ alkyl group, alkenyl group, cycloalkyl group, or cycloalkenyl group;

$A^1$ and $A^2$ are each independently a group of formula

—$(CH_2)_{p1}$—[$NR^2$—$(CH_2)_{q1}$-]$_{r1}NR^2_2$;

—$(CH_2)_{p2}$—N[—$(CH_2)_{q2}$—$NR^2_2$]$_2$;

—$(CH_2)_{p3}$—N{[—$(CH_2)_{q3}$—$NR^2_2$][—$(CH_2)_{q4}$—$NR^2$-]$_{r2}R^2$}; or

—$(CH_2)_{p4}$—N{—$(CH_2)_{q5}$—N[—$(CH_2)_{q6}$—$NR^2_2$]$_2$}$_2$, $B^1$ and $B^2$ are each independently —$(CH_2)_{p1}$—[$NR^2$—$(CH_2)_{q1}$-]$_{r1}NR^2$—$(CH_2)_{s1}$—$R^4$—$R^5$;

—$(CH_2)_{p2}$—N[—$(CH_2)_{q2}$—$NR^2$—$(CH_2)_{s2}$—$R^4$—$R^5$]$_2$;

—$(CH_2)_{p3}$—N{[—$(CH_2)_{q3}$—$NR^2_2$][—$(CH_2)_{q4}$—$NR^2$-]$_{r2}(CH_2)_{s3}$—$R^4$—$R^5$};

—$(CH_2)_{p4}$—N{—$(CH_2)_{q5}$—N[—$(CH_2)_{q6}$—$NR^2$—$(CH_2)_{s4}$—$R^4$—$R^5$]$_2$}$_2$;

—$(CH_2)_{p1}$—[$NR^2$—$(CH_2)_{q1}$-]$_{r1}NR^2$—$CH_2$—CHOH—$R^5$;

—$(CH_2)_{p2}$—N[—$(CH_2)_{q2}$—$NR^2$—$CH_2$—CHOH—$R^5$]$_2$;

—$(CH_2)_{p3}$—N{[—$(CH_2)_{q3}$—$NR^2_2$][—$(CH_2)_{q4}$—$NR^2$—]$_{r2}$—$CH_2$—CHOH—$R^5$};

—$(CH_2)_{p4}$—N{—$(CH_2)_{q5}$—N[—$(CH_2)_{q6}$—$NR^2$—$CH_2$—CHOH—$R^5$]$_2$}$_2$;

—$(CH_2)_{p1}$—[$NR^2$—$(CH_2)_{q1}$-]$_{r1}NR^2$—$(CH_2)_{s1}$—$R^5$;

—$(CH_2)_{p2}$—N[—$(CH_2)_{q2}$—$NR^2$—$(CH_2)_{s2}$—$R^5$]$_2$;

—$(CH_2)_{p3}$—N{[$(CH_2)_{q3}$—$NR^2$][—$(CH_2)_{q4}$—$NR^2$—]$_{r2}(CH_2)_{s3}$—$R^5$};

—$(CH_2)_{p4}$—N{—$(CH_2)_{q5}$—N[—$(CH_2)_{q6}$—$NR^2$—$(CH_2)_{s4}$—$R^5$]$_2$}$_2$;

—$(CH_2)_{p1}$—[N{$(CH_2)_{s1}$—$R^4$—$R^5$}—$(CH_2)_{q1}$-]$_{r1}NR^2_2$; or

—$(CH_2)_{p1}$—[N{$(CH_2)_{s1}$—$R^5$}—$(CH_2)_{q1}$-]$_{r1}NR^2_2$, wherein p1 to p4, q1 to q6, r1 and r2, and s1 to s4 are each independently an integer of 1 to 5;
each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O) NH—, or —S(O)(O)—; and each instance of $R^5$ is independently a substituted or unsubstituted alkyl group, cycloalkyl group, alkenyl group, cycloalkenyl group, aryl group, heteroalkyl group, heterocyclic group, or combination thereof optionally comprising from 1 to 8 (e.g., 2 to 8) secondary or tertiary amines or a substituent comprising a tissue-specific or cell-specific targeting moiety.

Also provided is a polymer of Formula 2:

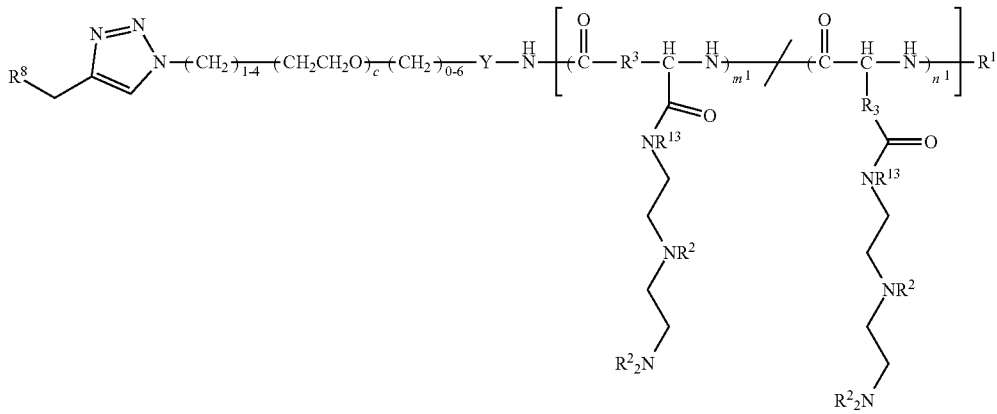

wherein:
each of $m^1$ and $n^1$ is an integer from 0 to 1000, provided that the sum of $m^1$ and $n^1$ is 10 to 2000;
c is an integer from 0 to 50;
Y is optionally present and is a cleavable linker;
$R^1$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents, such as one or more amines;
each instance of $R^2$ is independently hydrogen or a $C_1$-$C_{12}$ alkyl group, alkenyl group, cycloalkyl group, or cycloalkenyl group;
$R^8$ is a is a tissue-specific or cell-specific targeting moiety; and
each instance of $R^{13}$ is independently hydrogen or a $C_1$-$C_{12}$ alkyl group, alkenyl group, cycloalkyl group, or cycloalkenyl group.

The disclosure also provides a composition comprising a structure of Formula 1 and/or a polymer of Formula 2, and a nucleic acid and/or polypeptide. Further provided is a method of preparing a polymer comprising a structure of Formula 1 or a polymer of Formula 2, as well as methods of using the polymers and compositions comprising same, for example, to deliver a nucleic acid or protein to a cell.

BRIEF DESCRIPTION OF THE DRAWINGS

FIG. 1 provides the amino acid sequence of Cas9 from *Streptococcus pyogene* (SEQ ID NO:1).

FIG. 2 provides the amino acid sequence of Cpf1 from *Francisella tularensis* subsp. *Novicida* U112 (SEQ ID NO:2).

FIG. 16 provides the sequence of AsCpf1 (SEQ ID NO: 19).

FIG. 17 provides the sequence of LbCpf1 (SEQ ID NO: 20).

DETAILED DESCRIPTION OF THE INVENTION

Figure 3:
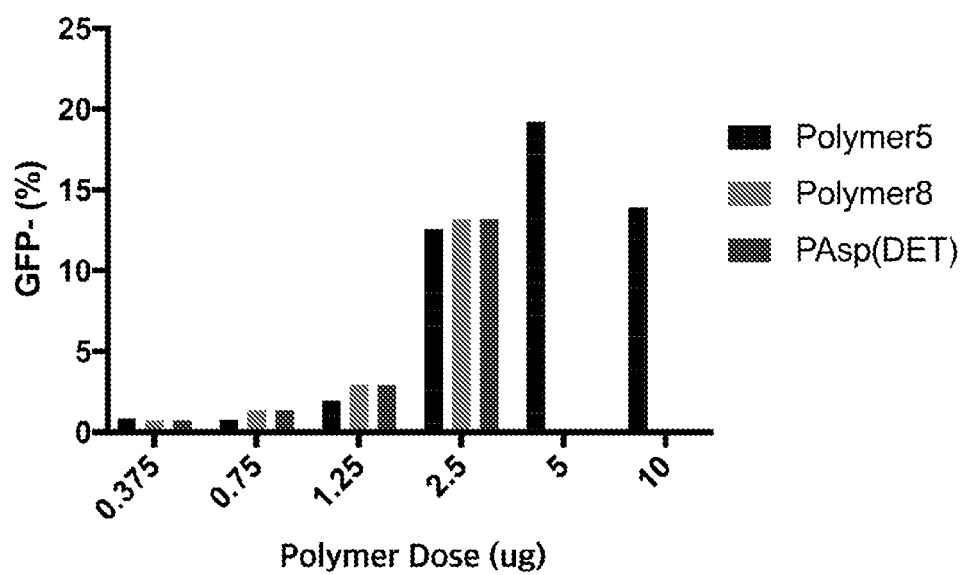
FIG. 3 is a graph of the level of Cas9 RNP delivery as measured by green fluorescent protein ("GFP") negative % in GFP-HEK cells at different dosages of polymer/Cas9 compositions.

The invention provides a polymer comprising a structure of Formula 1:

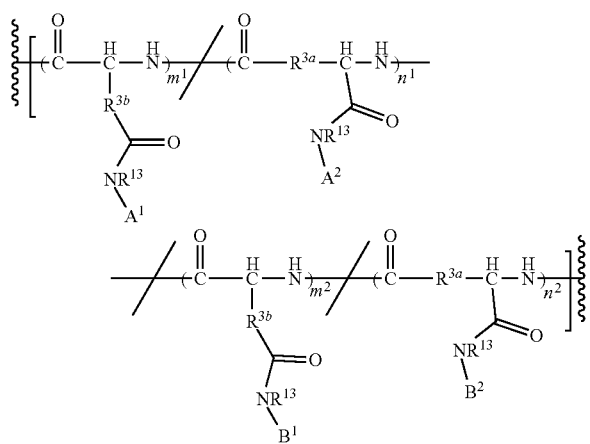

wherein:
  each of $m^1$ and $n^1$ is an integer from 0 to 1000;
  each of $m^2$ and $n^2$ is an integer from 0 to 1000, provided that the sum of $m^2+n^2$ is greater than 5;
  the symbol "/" indicates that the units separated thereby are linked randomly or in any order;
  $R^{3a}$ and $R^{3b}$ are each independently a methylene or ethylene group;
  each instance of $R^{13}$ is independently hydrogen or a $C_1$-$C_{12}$ alkyl group, alkenyl group, cycloalkyl group, or cycloalkenyl group;
  $A^1$ and $A^2$ are each independently a group of formula

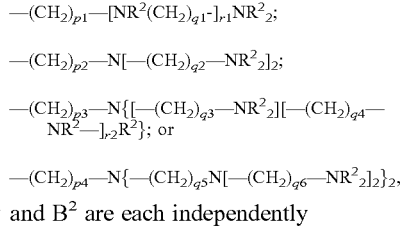

$B^1$ and $B^2$ are each independently

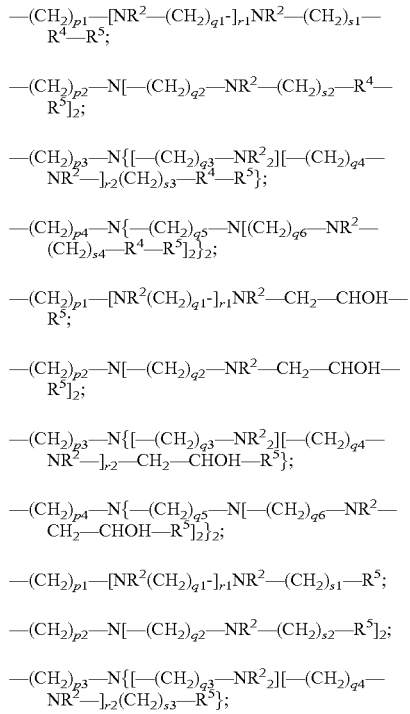

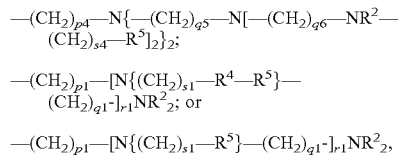

wherein
  p1 to p4, q1 to q6, r1 and r2, and s1 to s4 are each independently an integer of 1 to 5;
  each instance of $R^2$ is independently hydrogen or a $C_1$-$C_{12}$ alkyl group, alkenyl group, cycloalkyl group, or cycloalkenyl group;
  each instance of $R^4$ is independently —C(O)O—, —C(O)NH—, or —S(O)(O)—;
  and each instance of $R^5$ is independently an alkyl group, cycloalkyl group, alkenyl group, cycloalkenyl group, aryl group, heteroalkyl group, heterocyclic group, or combination thereof optionally comprising from 1 to 8 secondary or tertiary amines or a substituent comprising a tissue-specific or cell-specific targeting moiety.

As used herein, "alkyl" refers to a substituted or unsubstituted hydrocarbon chain. The alkyl group can have any number of carbon atoms (e.g., $C_1$-$C_{100}$ alkyl, $C_1$-$C_{50}$ alkyl, $C_1$-$C_{12}$ alkyl, $C_1$-$C_8$ alkyl, $C_1$-$C_6$ alkyl, $C_1$-$C_4$ alkyl, $C_1$-$C_2$ alkyl, etc.). The hydrocarbon chain can be saturated, or in some embodiments can be unsaturated to any degree (e.g., providing alkenyl or alkynyl groups), and can be linear, branched, straight-chained, cyclic (e.g., cycloalkyl or cycloalkenyl), or a combination thereof. Cyclic groups can be monocyclic, fused to form bicyclic or tricyclic groups, linked by a bond, or spirocyclic. Cyclic groups comprise at least three carbons (e.g., $C_3$-$C_{12}$, $C_3$-$C_{10}$, $C_3$-$C_8$, $C_3$-$C_6$, or $C_5$-$C_6$). In some embodiments, the hydrocarbon chain can be interrupted by one or more heteroatoms (e.g., 1, 2, 3, 4, or 5 or more atoms of oxygen, nitrogen, and/or sulfur), thereby providing a heteroalkyl, heteroalkenyl, heteroalkynyl, or heterocyclyl (i.e., a heterocyclic group). In some embodiments, the alkyl, alkenyl, alkynyl is substituted with one or more substituents.

The term "heterocyclyl," or "heterocyclic group" refers to a cyclic group, e.g., aromatic (e.g., heteroaryl) or non-aromatic where the cyclic group has one or more heteroatoms (e.g., 1, 2, 3, 4, or 5 or more atoms of oxygen, nitrogen, and/or sulfur). In some embodiments, the heterocyclyl or heterocyclic group (i.e., cyclic group, e.g., aromatic (e.g., heteroaryl) or non-aromatic where the cyclic group has one or more heteroatoms) is substituted with one or more substituents.

The term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. In some embodiments, the aryl group comprises an alkylene linking group so as to form an arylalkyl group (e.g., a benzyl group). Some aryl groups have from 6 to 12 ring members, such as phenyl, naphthyl or biphenyl. Other aryl groups have from 6 to 10 ring members, such as phenyl or naphthyl. In some embodiments, the aryl substituent comprise one or more heteroatoms (e.g., 1, 2, 3, 4, or 5 or more atoms of oxygen, nitrogen, and/or sulfur), thereby proving a heteroaryl group. In some embodiments, the aryl is substituted with one or more substituents.

It is understood that any of the foregoing groups may be univalent, bivalent, or multivalent (e.g., alkylene, alkenylene, alkynylene, arylene, heteroalkylene, heteroalkenylene, heteroalkynylene, heterocyclylene, heteroarylene, etc.).

As used herein, the term "substituted" can mean that one or more hydrogens on the designated atom or group (e.g., substituted alkyl group) are replaced with another group provided that the designated atom's normal valence is not exceeded. For example, when the substituent is oxo (i.e., =O), then two hydrogens on the atom are replaced. Substituent groups can include one or more of an aldehyde, an ester, an amide, a ketone, nitro, cyano, fluoroalkyl (e.g., trifluoromethane), halo (e.g., fluoro), aryl (e.g., phenyl), heterocyclyl or heterocyclic group (i.e., cyclic group, e.g., aromatic (e.g., heteroaryl) or non-aromatic where the cyclic group has one or more heteroatoms), oxo, or combinations thereof. Combinations of substituents and/or variables are permissible provided that the substitutions do not significantly adversely affect synthesis or use of the compound.

According to Formula 1, each of $m^1$ and $n^1$ is an integer from 0 to 1000, such as 0-500, 0-200, 0-100, or 0-50. Furthermore, each of $m^2$ and $n^2$ is an integer from 0 to 1000, such as 0-500, or 0-100, provided that the sum of $m^2+n^2$ is greater than 5 (e.g., 5-2000, 5-1000, 5-500, 5-200, 5-100, or 5-50). In other words, the polymer comprises at least some monomeric units of comprising groups $B^1$ and/or $B^2$, herein referred to collectively as the "B monomers." In some embodiments, $m^1$ and $n^1$ are zero, such that the polymer comprises no $A^1$ or $A^2$ groups. In other embodiments, the polymer comprises some $A^1$ and/or $A^2$ groups and some $B^1$ and/or $B^2$ groups. In such embodiments, the ratio of $(m+n^1)/(m^2+n^2)$ is about 20 or less (e.g., about 10 or less, about 5 or less, about 2 or less, or even about 1 or less). Also, in some embodiments, the ratio of $(m^1+n^1)/(m^2+n^2)$ is about 0.2 or more, such as about 0.5 or more.

The polymer can exist as any suitable structure type. For example, the polymer can exist as an alternating polymer, random polymer, block polymer, graft polymer, linear polymer, branched polymer, cyclic polymer, or a combination thereof. In certain embodiments, the polymer is a random polymer, block polymer, graft polymer, or a combination thereof.

Thus, in the structure of Formula 1, the monomers (which can be referred to by their respective side chains $A^1$, $A^2$, $B^1$, and $B^2$) can be arranged randomly or in any order. The integers $m^1$, $n^1$, $m^2$, and $n^2$ merely denote the number of the respective monomers that appear in the chain overall, and do not necessarily represent blocks of those monomers, although blocks or stretches of a given monomer might be present in some embodiments. For instance, the structure of Formula 1 can comprise the monomers in the order -$A^1$-$A^2$-$B^1$-$B^2$-, -$A^2$-$A^1$-$B^2$-$B^1$-, -$A^1$-$B^1$-$A^2$-$B^2$—, etc. In some embodiments, the polymer has a polypeptide (e.g., polyaspartamide) backbone arranged in an alpha/beta configuration, such that the "1" and "2" monomers alternate (e.g., -$A^1$-$A^2$-$B^1$-$B^2$-, -$A^2$-$A^1$-$B^2$-$B^1$-, -$A^1$-$B^2$-$B^1$-$A^2$-, -$A^2$-$B^1$-$B^2$-$A^1$-, —$B^1$-$A^2$-$B^1$-$A^2$-, etc.). However, the "A" and "B" monomers or sidechains (e.g., $A^1/A^2$ and $B^1/B^2$) can be dispersed randomly throughout the polymer backbone, or can be arranged in blocks, or some combination thereof.

By way of further illustration, the polymer could instead be described as Formula 1.1:

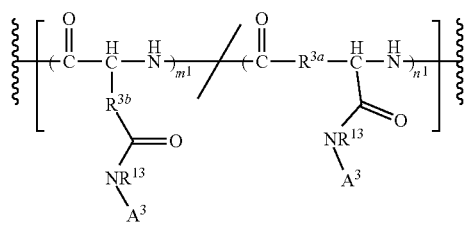

or, where the backbone is in an alpha, beta configuration, as Formula 1.2:

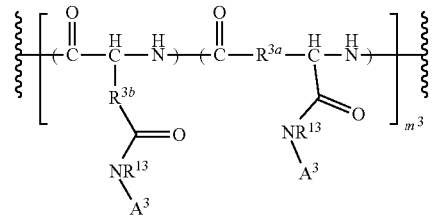

wherein, $m^1$ and $n^1$ are as previously described;

$m^3$ is an integer from 5-2000 (e.g., 5-1000, 5-500, 5-100, 25-2000, 25-500, 25-100, 50-2000, 50-1000, 50-500, or 50-100);

the symbol "/" indicates that the units separated thereby are linked randomly or in any order;

$R^{3a}$ and $R^{3b}$ are each independently a methylene or ethylene group;

each instance of $R^{13}$ is independently hydrogen or a $C_1$-$C_{12}$ alkyl group, alkenyl group, cycloalkyl group, or cycloalkenyl group;

each $A^3$ is independently a group of formula

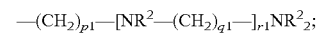

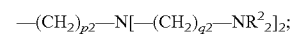

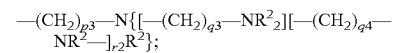

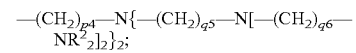

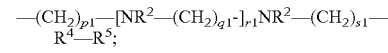

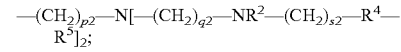

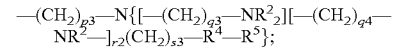

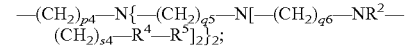

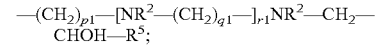

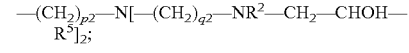

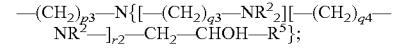

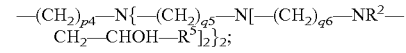

—(CH$_2$)$_{p1}$—[NR$^2$—(CH$_2$)$_{q1}$-]$_{r1}$NR$^2$—(CH$_2$)$_{s1}$—R$^5$;

—(CH$_2$)$_{p2}$—N[—(CH$_2$)$_{q2}$—NR$^2$—(CH$_2$)$_{s2}$—R$^5$]$_2$;

—(CH$_2$)$_{p3}$—N{[—(CH$_2$)$_{q3}$—NR$^2$]$_{r2}$(CH$_2$)$_{s3}$—R$^5$};

—(CH$_2$)$_{p4}$—N{—(CH$_2$)$_{q5}$—N[—(CH$_2$)$_{q6}$—NR$^2$—(CH$_2$)$_{s4}$—R$^5$]$_2$}$_2$;

—(CH$_2$)$_{p1}$—[N{(CH$_2$)$_{s1}$—R$^4$—R$^5$}—(CH$_2$)$_{q1}$-]$_{r1}$NR$^2$$_2$; or

—(CH$_2$)$_{p1}$—[N{(CH$_2$)$_{s1}$—R$^5$}—(CH$_2$)$_{q1}$-]$_{r1}$NR$^2$$_2$, wherein p1 to p4, q1 to q6, r1 and r2, and s1 to s4 are each independently an integer of 1 to 5;

each instance of R$^2$ is independently hydrogen or a C$_1$-C$_{12}$ alkyl group, alkenyl group, cycloalkyl group, or cycloalkenyl group;

each instance of R$^4$ is independently —C(O)O—, —C(O)NH—, or —S(O)(O)—; and each instance of R$^5$ is independently an alkyl group, cycloalkyl group, alkenyl group, cycloalkenyl group, aryl group, heteroalkyl group, heterocyclic group, or combination thereof optionally comprising from 1 to 8 or 2 to 8 secondary or tertiary amines or a substituent comprising a tissue-specific or cell-specific targeting moiety;

provided that at least about 5% (such as at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or even 100%) of the A$^3$ groups are selected from —(CH$_2$)$_{p1}$—[NR$^2$—(CH$_2$)$_{q1}$-]$_{r1}$NR$^2$—(CH$_2$)$_{s1}$—R$^4$—R$^5$;

—(CH$_2$)$_{p2}$—N[—(CH$_2$)$_{q2}$—NR$^2$—(CH$_2$)$_{s2}$—R$^4$—R$^5$]$_2$;

—(CH$_2$)$_{p3}$—N{[—(CH$_2$)$_{q3}$—NR$^2$]$_{r2}$(CH$_2$)$_{s3}$—R$^4$—R$^5$};

—(CH$_2$)$_{p4}$—N{—(CH$_2$)$_{q5}$—N[—(CH$_2$)$_{q6}$—NR$^2$—(CH$_2$)$_{s4}$—R$^4$—R$^5$]$_2$}$_2$;

—(CH$_2$)$_{p1}$—[NR$^2$—(CH$_2$)$_{q1}$-]$_{r1}$NR$^2$—CH$_2$—CHOH—R$^5$;

—(CH$_2$)$_{p2}$—N[—(CH$_2$)$_{q2}$—NR$^2$—CH$_2$—CHOH—R$^5$]$_2$;

—(CH$_2$)$_{p3}$—N{[—(CH$_2$)$_{q3}$—NR$^2$]$_{r2}$—CH$_2$—CHOH—R$^5$};

—(CH$_2$)$_{p4}$—N{—(CH$_2$)$_{q5}$—N[—(CH$_2$)$_{q6}$—NR$^2$—CH$_2$—CHOH—R$^5$]$_2$}$_2$;

—(CH$_2$)$_{p1}$—[NR$^2$(CH$_2$)$_{q1}$-]$_{r1}$NR$^2$—(CH$_2$)$_{s1}$—R$^5$;

—(CH$_2$)$_{p2}$—N[—(CH$_2$)$_{q2}$—NR$^2$—(CH$_2$)$_{s2}$—R$^5$]$_2$;

—(CH$_2$)$_{p3}$—N{[—(CH$_2$)$_{q3}$—NR$^2$]$_{r2}$(CH$_2$)$_{s3}$—R$^5$};

—(CH$_2$)$_{p4}$—N{(CH$_2$)$_{q5}$—N[—(CH$_2$)$_{q6}$—NR$^2$—(CH$_2$)$_{s4}$—R$^5$]$_2$}$_2$;

—(CH$_2$)$_{p1}$—[N{(CH$_2$)$_{s1}$—R$^4$—R$^5$}—(CH$_2$)$_{q1}$-]$_{r1}$NR$^2$$_2$; or

—(CH$_2$)$_{p1}$—[N{(CH$_2$)$_{s1}$—R$^5$}—(CH$_2$)$_{q1}$-]$_{r1}$NR$^2$$_2$,

In still other embodiments, the polymer has some or even a majority of A$^3$ groups (at least about 5%, at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%) that are selected from —(CH$_2$)$_{p1}$—[NR$^2$—(CH$_2$)$_{q1}$-]$_{r1}$NR$^2$$_2$;

—(CH$_2$)$_{p2}$—N[—(CH$_2$)$_{q2}$—NR$^2$$_2$]$_2$;

—(CH$_2$)$_{p3}$—N{[—(CH$_2$)$_{q3}$—NR$^2$$_2$][—(CH$_2$)$_{q4}$—NR$^2$—]$_{r2}$R$^2$}; or

—(CH$_2$)$_{p4}$—N{—(CH$_2$)$_{q5}$—N[—(CH$_2$)$_{q6}$—NR$^2$$_2$]$_2$}$_2$.

In any of the forgoing polymer structures, R$^{3a}$ and R$^{3b}$ are each independently a methylene or ethylene group. In some embodiments, R$^{3a}$ is an ethylene group and R$^{3b}$ is a methylene group; or R$^{3a}$ is a methylene group and R$^{3b}$ is an ethylene group. In certain embodiments, R$^{3a}$ and R$^{3b}$ are each an ethylene group. In preferred embodiments, R$^{3a}$ and R$^{3b}$ are each a methylene group.

Groups A$^1$ and A$^2$ are independently selected and, therefore, can be the same or different from one another. Similarly, groups B$^1$ and B$^2$ are independently selected and can be the same or different from one another. Furthermore, each instance of A$^3$ can be the same or different from other A$^3$ groups.

In groups A$^1$, A$^2$, A$^3$, B$^1$, and B$^2$, integers p1 to p4 (i.e., p1, p2, p3, and p4), q1 to q6 (i.e., q1, q2, q3, q4, q5, and q6), and r and r2 are each independently an integer of 1 to 5 (e.g., 1, 2, 3, 4, or 5). In some embodiments, p1 to p4 (i.e., p1, p2, p3, and p4), q1 to q6 (i.e., q1, q2, q3, q4, q5, and q6), and/or r and r2 are each independently an integer of 1 to 3 (e.g., 1, 2, or 3). In certain embodiments, p1 to p4 (i.e., p1, p2, p3, and p4) and/or q1 to q6 (i.e., q1, q2, q3, q4, q5, and q6) are each 2. In some embodiments, p1 to p4 (i.e., p1, p2, p3, and p4) and/or q1 to q6 (i.e., q1, q2, q3, q4, q5, and q6) are each 2, and r1 and r2 are each 1. In some embodiements, s1-s4 are each independently an integer of 1, 2, 3, 4, or 5, such as 1, 2, or 3, or 1-2.

In the polymer structures, each instance of R$^4$ is independently —C(O)O—, —C(O)NH—, or —S(O)(O)—. In some embodiments, each instance of R$^4$ is independently —C(O)O— or —C(O)NH—. In certain embodiments, each instance of R$^4$ is —C(O)O—. In certain embodiments, each instance of R$^4$ is —C(O)NH—.

In some embodiments of Formula 1, each of A$^1$ and A$^2$ is a group of formula —(CH$_2$)$_{p1}$—[NH—(CH$_2$)$_{q1}$—]$_{r1}$NH$_2$, such as a group —(CH$_2$)$_2$—NH—(CH$_2$)$_2$—NH$_2$. In addition, or alternatively, each of B$^1$ and B$^2$ is a group of formula —(CH$_2$)$_{p1}$—[NH—(CH$_2$)$_{q1}$—]$_{r1}$NH—(CH$_2$)$_2$—R$^4$—R$^5$, such as a group —(CH$_2$)$_2$—NH—(CH$_2$)$_2$—NH—(CH$_2$)$_2$—R$^4$—R$^5$, or a group —(CH$_2$)$_2$—NH—(CH$_2$)$_2$—NH—(CH$_2$)$_2$—C(O)—O—R$^5$. In some embodiments, each of B$^1$ and B$^2$ is a group of the formula —(CH$_2$)$_{p1}$—[NR$^2$—(CH$_2$)$_{q1}$—]$_{r1}$NR$^2$—(CH$_2$)$_{s1}$—R$^5$ or —(CH$_2$)$_2$—NR$^2$—(CH$_2$)$_2$—NR$^2$—(CH$_2$)$_2$—R$^5$, optionally wherein each R$^2$ is independently a C$_1$-C$_3$ alkyl (e.g., methyl), and optionally wherein $R^5$ is a $C_1$-$C_3$ alkyl amino or $C_1$-$C_3$ dialkylamino (e.g., $R^5$ is —$CH_2$—NH—$CH_3$ or —$CH_2$—N—$(CH_3)_2$).

In some embodiments of Formula 1.1, $A^3$ is a group of the formula —$(CH_2)_{p1}$—[NH—$(CH_2)_{q1}$—]$_{r1}$NH$_2$, such as a group —$(CH_2)_2$—NH—$(CH_2)_2$—NH$_2$; or a group of formula —$(CH_2)_{p1}$—[NH—$(CH_2)_{q1}$—]$_{r1}$NH—$(CH_2)_2$—$R^4$—$R^5$, such as a group —$(CH_2)_2$—NH—$(CH_2)_2$—NH—$(CH_2)_2$—$R^4$—$R^5$; —$(CH_2)_2$—NH—$(CH_2)_2$—NH—$(CH_2)_2$—C(O)—O—$R^5$; or a group —$(CH_2)_{p1}$—[NR$^2$—$(CH_2)_{q1}$—]$_{r1}$NR$^2$—$(CH_2)_2$—$R^5$, such as —$(CH_2)_2$—NR$^2$—$(CH_2)_2$—NR$^2$—$(CH_2)_2$—$R^5$, optionally wherein each $R^2$ is independently a $C_1$-$C_3$ alkyl (e.g., methyl), and optionally wherein $R^5$ is a $C_1$-$C_3$ alkyl amino or $C_1$-$C_3$ dialkylamino (e.g., $R^5$ is —$CH_2$—NH—$CH_3$ or —$CH_2$—N—$(CH_3)_2$); provided that at least about 5% (such as at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or even 100%) of the $A^3$ groups are —$(CH_2)_{p1}$—[NH—$(CH_2)_{q1}$—]$_{r1}$NH—$(CH_2)_2$—$R^4$—$R^5$, such as a group —$(CH_2)_2$—NH—$(CH_2)_2$—NH—$(CH_2)_2$—$R^4$—$R^5$, or a group —$(CH_2)_2$—NH—$(CH_2)_2$—NH—$(CH_2)_2$—C(O)—O—$R^5$; or a group —$(CH_2)_{p1}$—[NR$^2$—$(CH_2)_{q1}$—]$_{r1}$NR$^2$—$(CH_2)_{s1}$—$R^5$, such as —$(CH_2)_2$—NR$^2$—$(CH_2)_2$—NR$^2$—$(CH_2)_2$—$R^5$, optionally wherein each $R^2$ is independently a $C_1$-$C_3$ alkyl (e.g., methyl), and optionally wherein $R^5$ is a $C_1$-$C_3$ alkyl amino or $C_1$-$C_3$ dialkylamino (e.g., $R^5$ is —$CH_2$—NH—$CH_3$ or —$CH_2$—N—$(CH_3)_2$). Additionally, in some embodiments, the polymer has some or even a majority of $A^3$ groups (at least about 5%, at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%) that are —$(CH_2)_{p1}$—[NH—$(CH_2)_{q1}$—]$_{r1}$NH—$(CH_2)_2$—$R^4$—$R^5$, such as a group —$(CH_2)_2$—NH—$(CH_2)_2$—NH—$(CH_2)_2$—$R^4$—$R^5$, or a group —$(CH_2)_2$—NH—$(CH_2)_2$—NH—$(CH_2)_2$—C(O)—O—$R^5$; or a group —$(CH_2)_{p1}$—[NR$^2$—$(CH_2)_{q1}$—]$_{r1}$NR$^2$—$(CH_2)_{s1}$—$R^5$, such as —$(CH_2)_2$—NR$^2$—$(CH_2)_2$—NR$^2$—$(CH_2)_2$—$R^5$, optionally wherein each $R^2$ is independently a $C_1$-$C_3$ alkyl (e.g., methyl), and optionally wherein $R^5$ is a $C_1$-$C_3$ alkyl amino or $C_1$-$C_3$ dialkylamino (e.g., $R^5$ is —$CH_2$—NH—$CH_3$ or —$CH_2$—N—$(CH_3)_2$).

Furthermore, in the polymer structures, each instance of $R^5$ is independently an alkyl group, cycloalkyl group, alkenyl group, cycloalkenyl group, aryl group, heteroalkyl group, heterocyclic group, or combination thereof, optionally comprising from 1 to 8 (or 2 to 8) secondary or tertiary amines. Any of the foregoing groups of $R^5$ can be substituted or unsubstituted. $R^5$ also can be a substituent comprising a tissue-specific or cell-specific targeting moiety. In some embodiments, $R^5$ can comprise from about 1 to about 50 carbon atoms (e.g., from about 2 to about 50 carbon atoms, such as about 2 to about 40 carbon atoms, from about 2 to about 30 carbon atoms, from about 2 to about 20 carbon atoms, from about 1 to about 16 or about 2 to about 16 carbon atoms, from about 1 to about 12 or about 2 to about 12 carbon atoms, from about 1 to about 10 or about 2 to about 10 carbon atoms, or from about 1 to about 8 or about 2 to about 8 carbon atoms). In some embodiments, $R^5$ is a heteroalkyl group comprising from 1 to 8 or 2 to 8 (i.e., 1, 2, 3, 4, 5, 6, 7, or 8) secondary or tertiary amines. The secondary or tertiary amines can be part of the heteroalkyl backbone (i.e., the longest continuous chain of atoms in the heteroalkyl group, or a pendant substituent. Thus, for instance, the heteroalkyl group comprising the secondary or tertiary amines can be an alkylamino group, dialkylamino group, amino alkyl group, alkylaminoalkyl group, dialkylaminoalkyl group, aminoalkylamino group, or the like comprising 1 to 8 (or 2-8) secondary or tertiary amines.

In some embodiments, each $R^5$ is independently selected from:

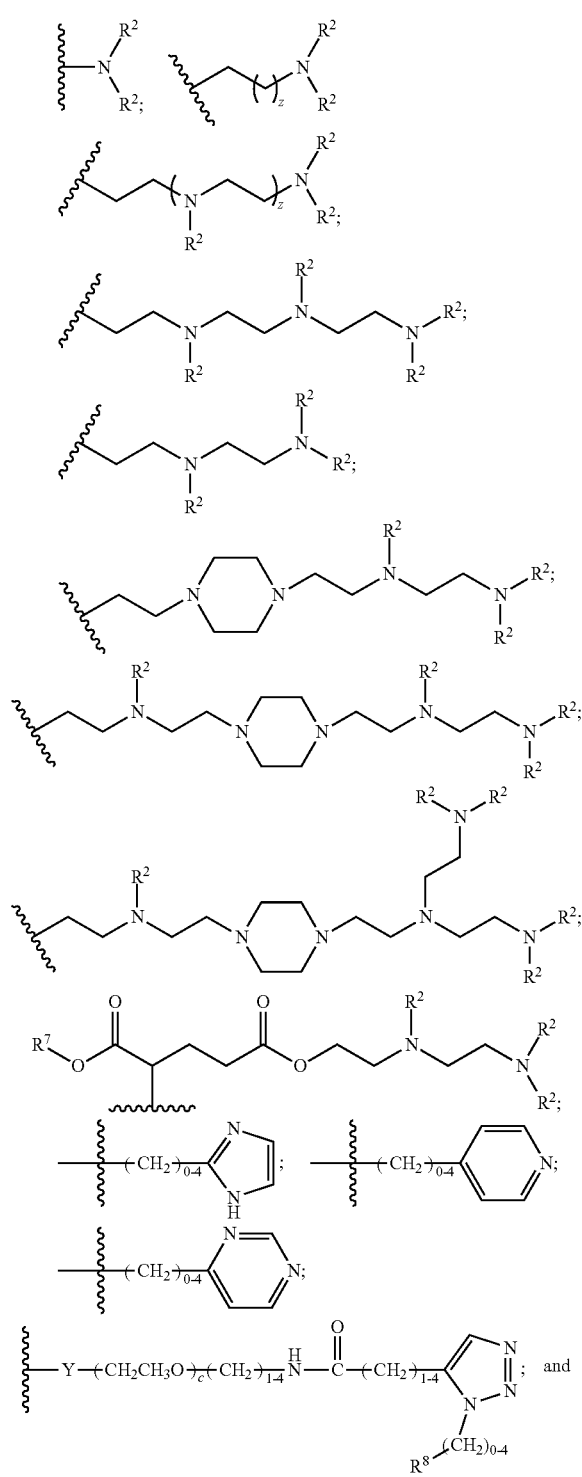

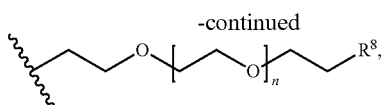

wherein
each instance of $R^2$ is independently hydrogen or a $C_1$-$C_{12}$ alkyl group, alkenyl group, cycloalkyl group, or cycloalkenyl group;
$R^7$ is a $C_1$-$C_{50}$ alkyl group, alkenyl group, cycloalkyl group, or cycloalkenyl group optionally substituted with one or more amines;
z is an integer from 1 to 5;
c is an integer from 0 to 50;
Y is optionally present and is a cleavable linker;
n is an integer from 0 to 50; and
$R^8$ is a tissue-specific or cell-specific targeting moiety, $C_1$-$C_{12}$ alkyl group, alkenyl group, cycloalkyl group, or cycloalkenyl group Each instance of $R^2$ can be hydrogen or a $C_1$-$C_{12}$ alkyl group, alkenyl group, cycloalkyl group, or cycloalkenyl group. In some embodiments, $R^2$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group. In certain embodiments, $R^2$ is methyl or hydrogen.

$R^7$ can be a $C_1$-$C_{50}$ (e.g., $C_1$-$C_{40}$, $C_1$-$C_{30}$, $C_1$-$C_{20}$, $C_1$-$C_{10}$, $C_4$-$C_{12}$, or $C_6$-$C_8$) alkyl group, alkenyl group, cycloalkyl group, or cycloalkenyl group optionally substituted with one or more amines. In some embodiments, $R^7$ is a $C_4$-$C_{12}$, such as a $C_6$-$C_8$, alkyl group, alkenyl group, cycloalkyl group, or cycloalkenyl group optionally substituted with one or more amines. In some embodiments, $R^7$ is substituted with one or more amines. In certain embodiments, $R^7$ is substituted with 1 to 8 or 2 to 8 (i.e., 1, 2, 3, 4, 5, 6, 7, or 8) secondary or tertiary amines. The amines can be a part of the alkyl group (i.e., encompassed in the alkyl group backbone) or a pendant substituent.

$R^{13}$ can be hydrogen or a $C_1$-$C_{12}$ alkyl group, alkenyl group, cycloalkyl group, or cycloalkenyl group. In some embodiments, $R^{13}$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group. In certain embodiments, $R^{13}$ is methyl. In other embodiments, $R^{13}$ can be hydrogen. Typically, within a given polymer, each $R^{13}$ is the same (e.g., all methyl or all hydrogen); however, each $R^{13}$ is independently chosen and can be the same or different.

Each instance of Y is optionally present. As used herein, the phrase "optionally present" means that a substituent designated as optionally present can be present or not present, and when that substituent is not present, the adjoining substituents are bound directly to each other. When Y is present, Y is a cleavable linker. As used herein, the phrase "cleavable linker" refers to any chemical element that connects two species that can be cleaved as to separate the two species. For example, the cleavable linker can be cleaved by a hydrolytic process, photochemical process, radical process, enzymatic process, electrochemical process, or a combination thereof. Exemplary cleavable linkers include, but are not limited to:

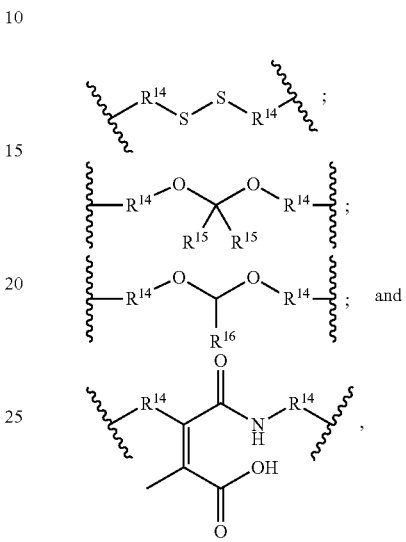

wherein each occasion of $R^{14}$ independently is a $C_1$-$C_4$ alkyl group, each occasion of $R^{15}$ independently is hydrogen, an aryl group, a heterocyclic group (e.g., aromatic or non-aromatic), a $C_1$-$C_{12}$ alkyl group, alkenyl group, cycloalkyl group, or cycloalkenyl group, and $R^{16}$ is a six-membered aromatic or heteroaromatic group optionally substituted with one or more —$OCH_3$, —$NHCH_3$, —$N(CH_3)_2$, —$SCH_3$, —OH, or a combination thereof.

The polymer can be any suitable polymer, provided the polymer comprises the foregoing polymer structure as part of the polymer. In some embodiments, the polymer is a block copolymer comprising a polymer block having the structure of Formula 1, 1.1, or 1.2, and one or more other polymer blocks (e.g., an ethylene oxide subunit, or a propylene oxide subunit). In other embodiments, the structure of Formula 1, 1.1, or 1.2 is the only polymeric unit of the polymer, which may be "capped" at either end with a suitable terminus. In certain embodiments, the polymer further comprises a substituent comprising a tissue-specific or cell-specific targeting moiety.

In some embodiments, the polymer has structure of Formula 1A:

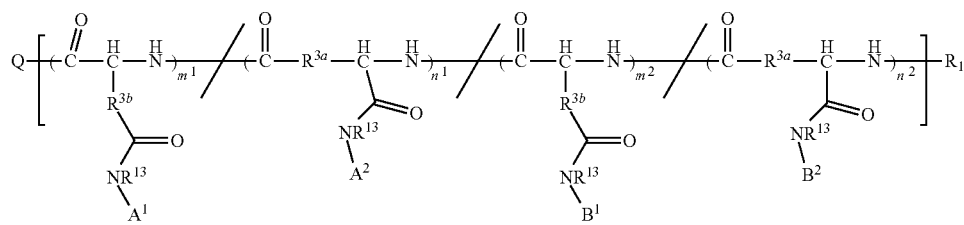

wherein Q is of the formula:

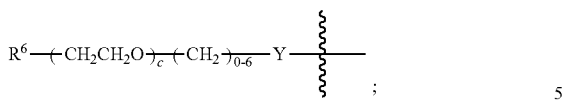

;

or Formula 1A¹:

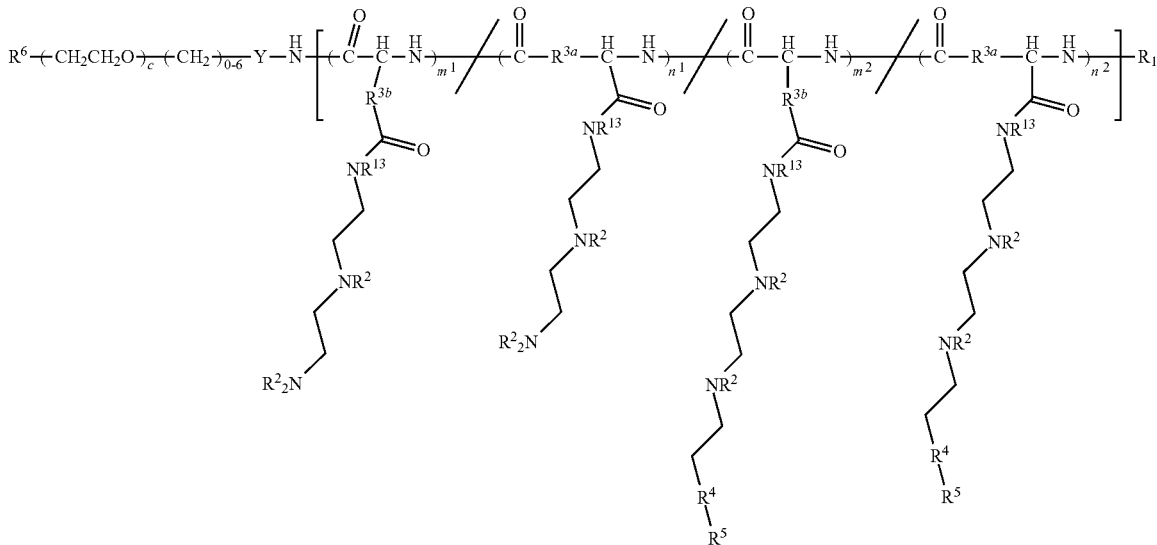

wherein
- c is an integer from 0 to 50;
- Y is optionally present and is a cleavable linker as previously described;
- $R^1$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents, such as one or more amines;
- $R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
- each instance of $R^{13}$ is independently hydrogen or a $C_1$-$C_{12}$ alkyl group, alkenyl group, cycloalkyl group, or cycloalkenyl group;
- and all other substituents (e.g., $m^1$, $n^1$, $m^2$, $n^2$, $R^2$, $R^{3a}$, $R^{3b}$, $R^4$, $R^5$, and $R^{13}$) are as previously described.

Similarly, the polymer can have the structure of Formula 1.1A:

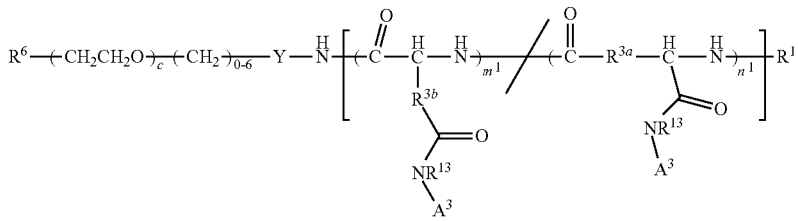

or, where the backbone is in an alpha, beta configuration, as Formula 1.2A:

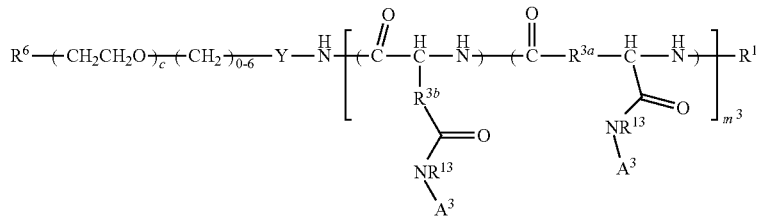

wherein,
c is an integer from 0 to 50;
Y is optionally present and is a cleavable linker as previously described;
$R^1$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents, such as one or more amines;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
each instance of $R^{13}$ is independently hydrogen or a $C_1$-$C_{12}$ alkyl group, alkenyl group, cycloalkyl group, or cycloalkenyl group;
and all other substituents (e.g., $m^3$, $R^{3a}$, $R^{3b}$, and $A^3$) are as previously described.

In some embodiments of the foregoing, $R^1$ and/or $R^6$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group substituted with one or more substituents. In certain embodiments, the heteroalkyl or alkyl group comprises or is substituted with one or more amines, for instance, from 1 to 8 or 2 to 8 (i.e., 1, 2, 3, 4, 5, 6, 7, or 8) secondary or tertiary amines. The amines can be a part of the heteroalkyl backbone chain or pendant substituents.

Non-limiting examples of the polymers provided herein include, for instance:

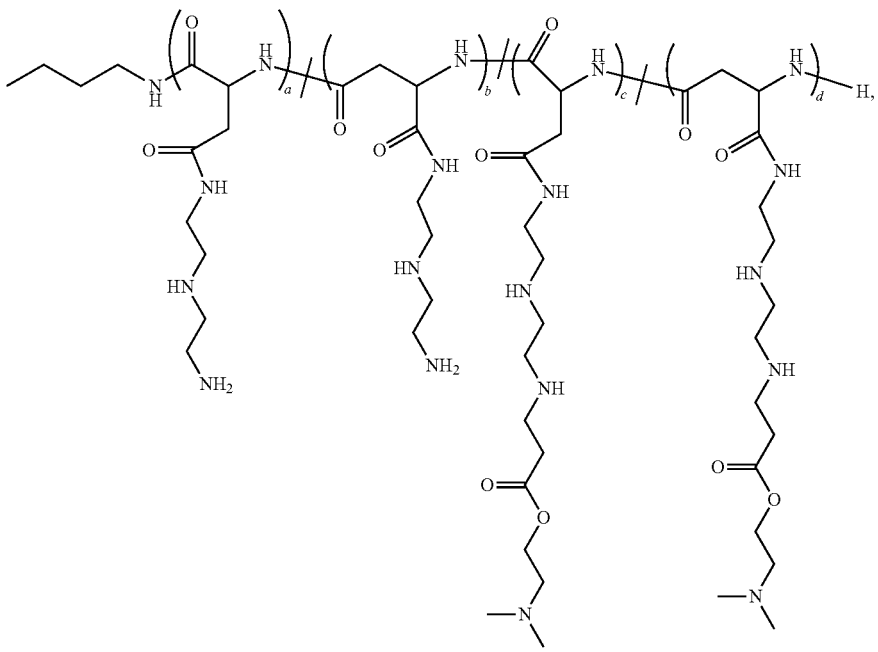

Polymer 1

Polymer 2
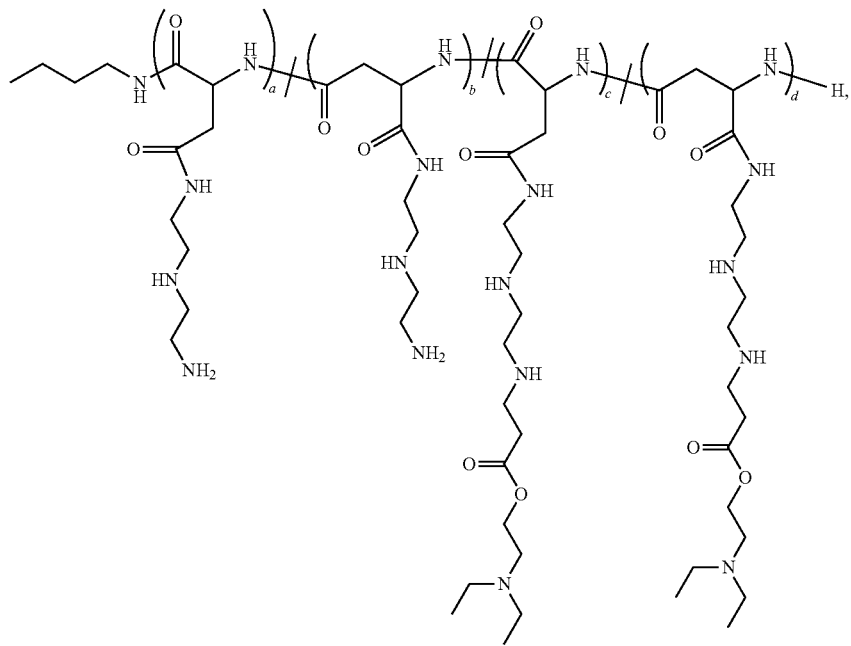
Polymer 3
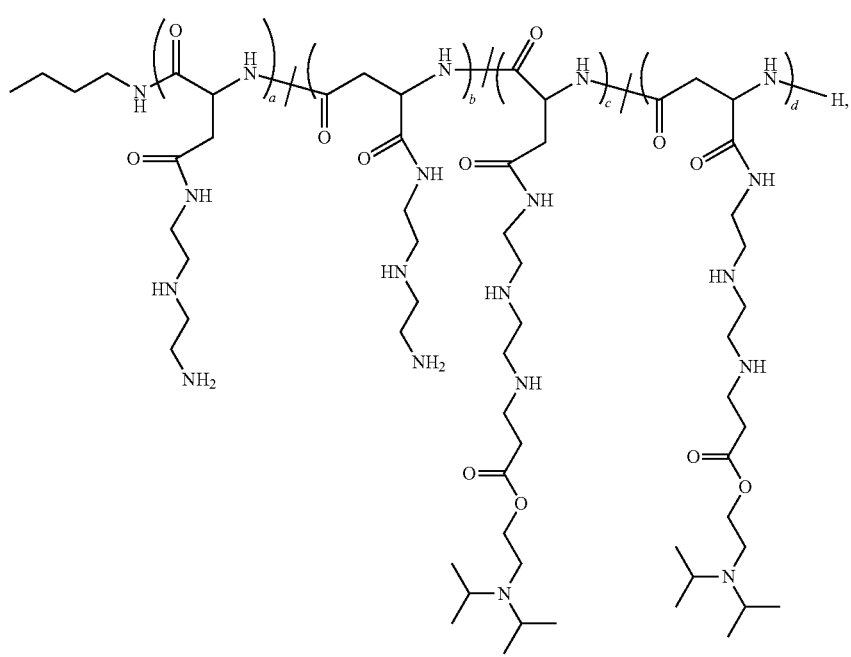

-continued
Polymer 4
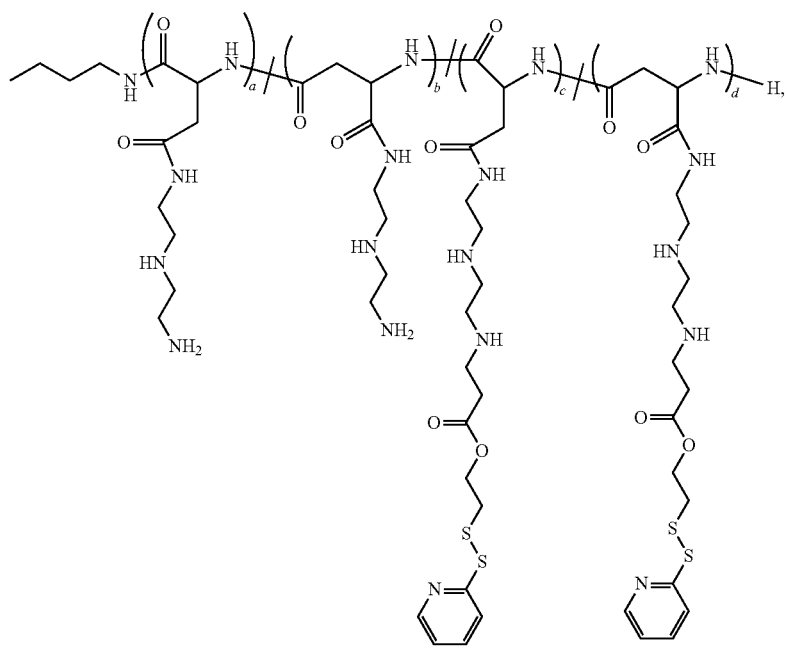
Polymer 5
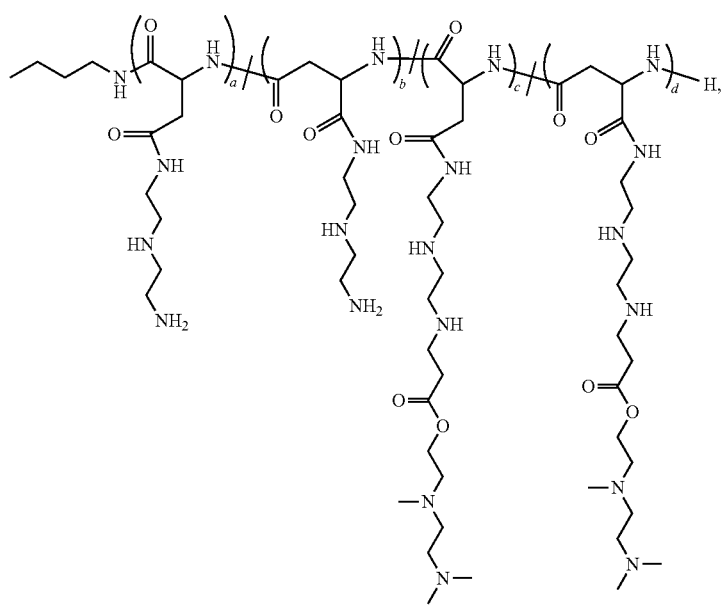

Polymer 6
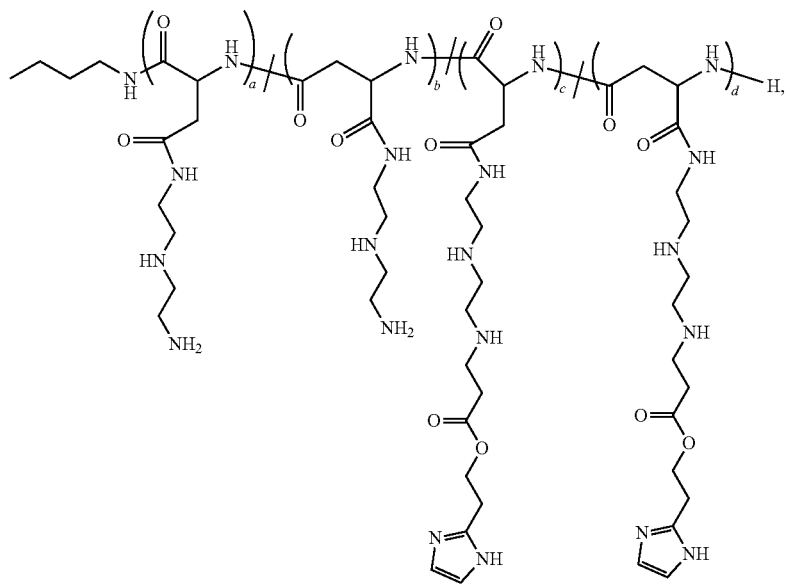
Polymer 7
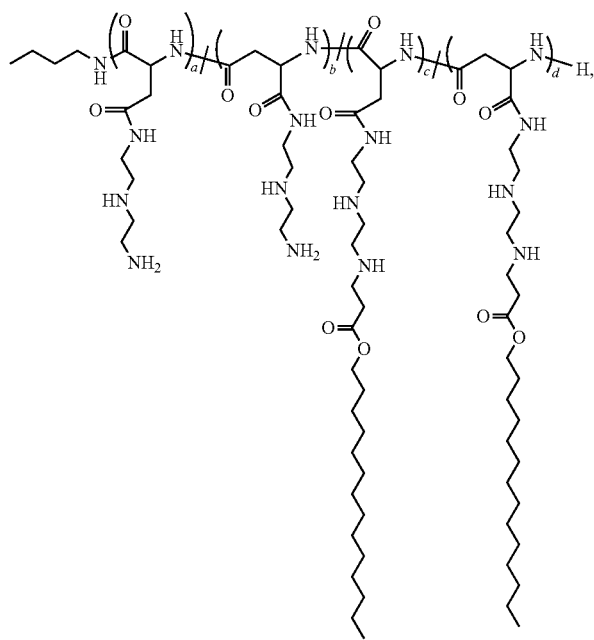

Polymer 8
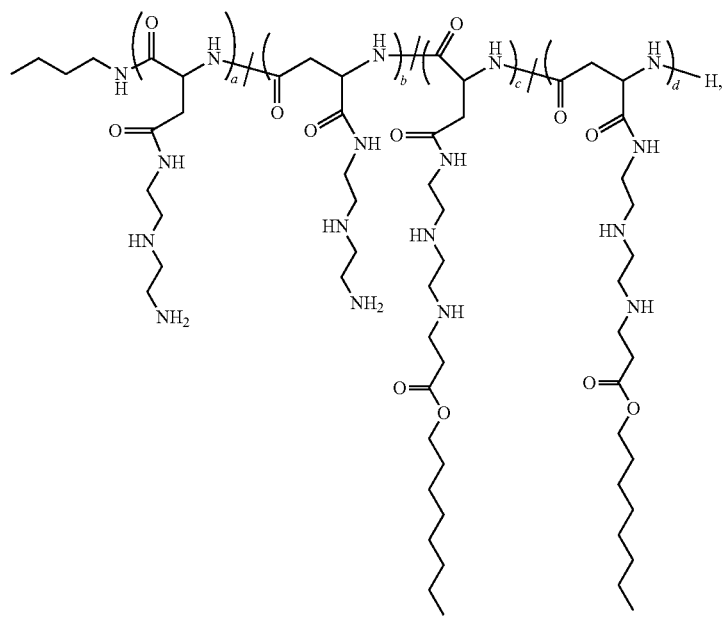
Polymer 9
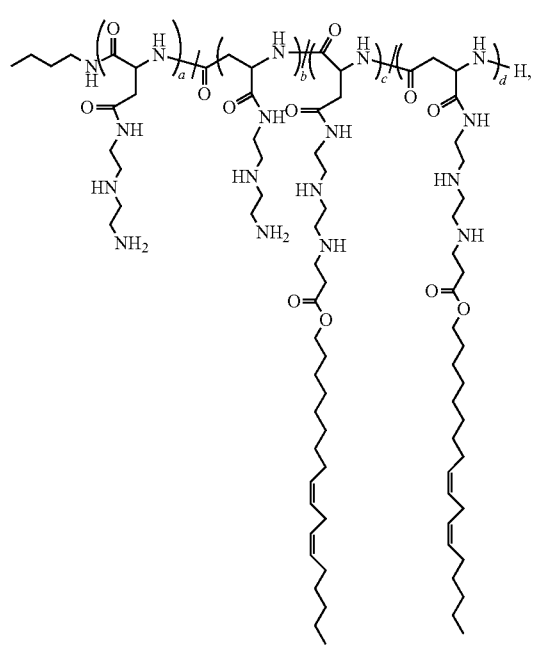

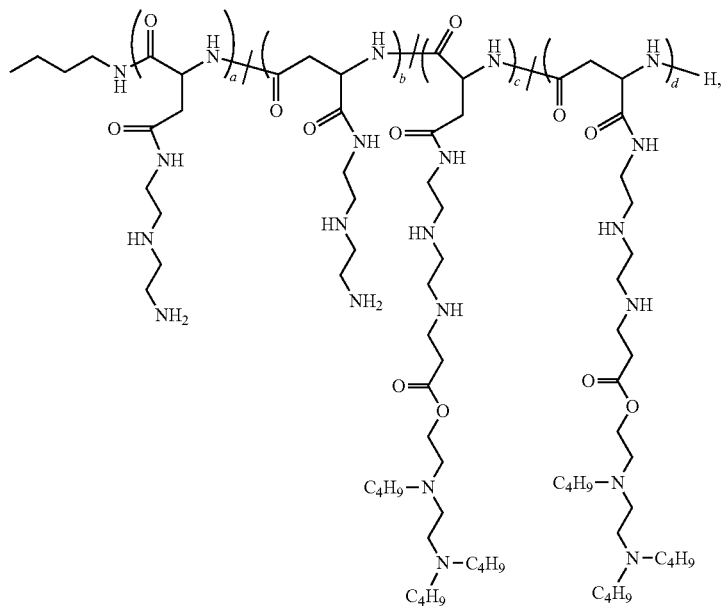
Polymer 10
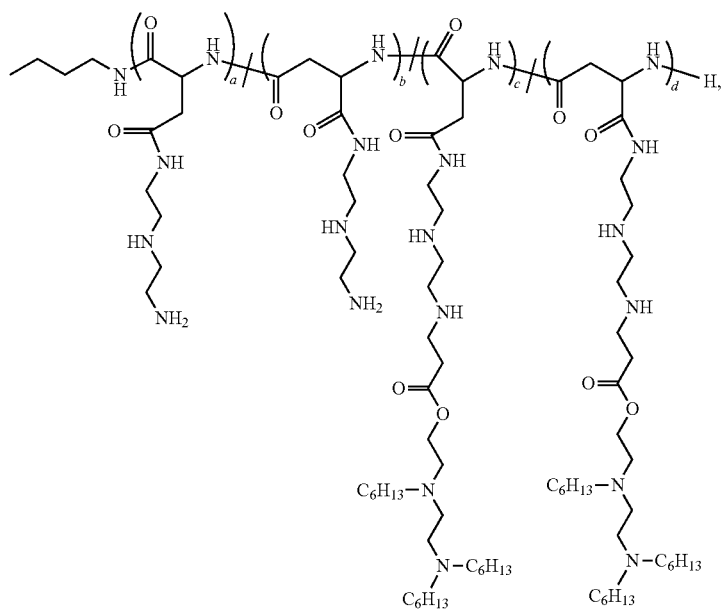
Polymer 11

Polymer 12
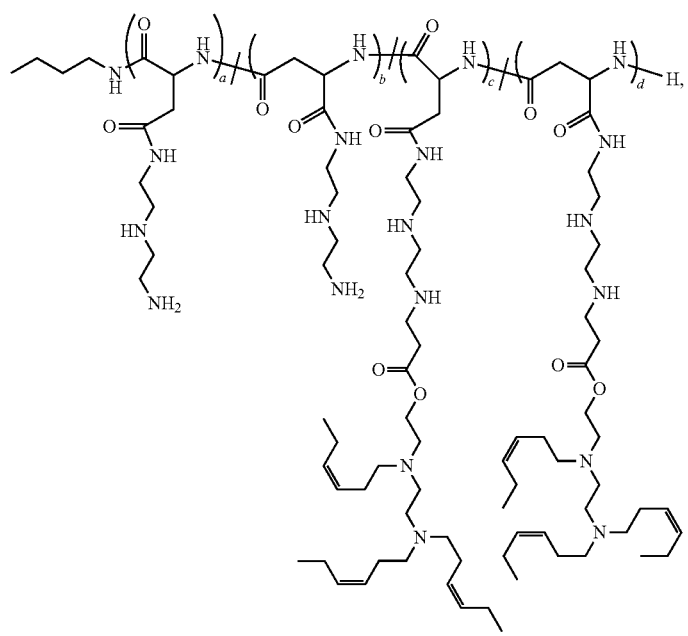
Polymer 13
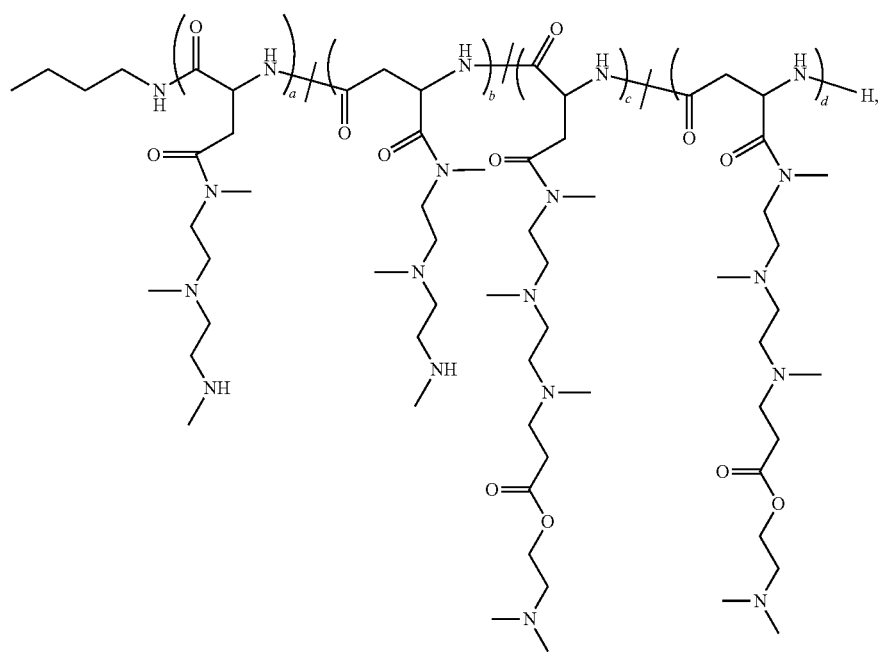

Polymer 14
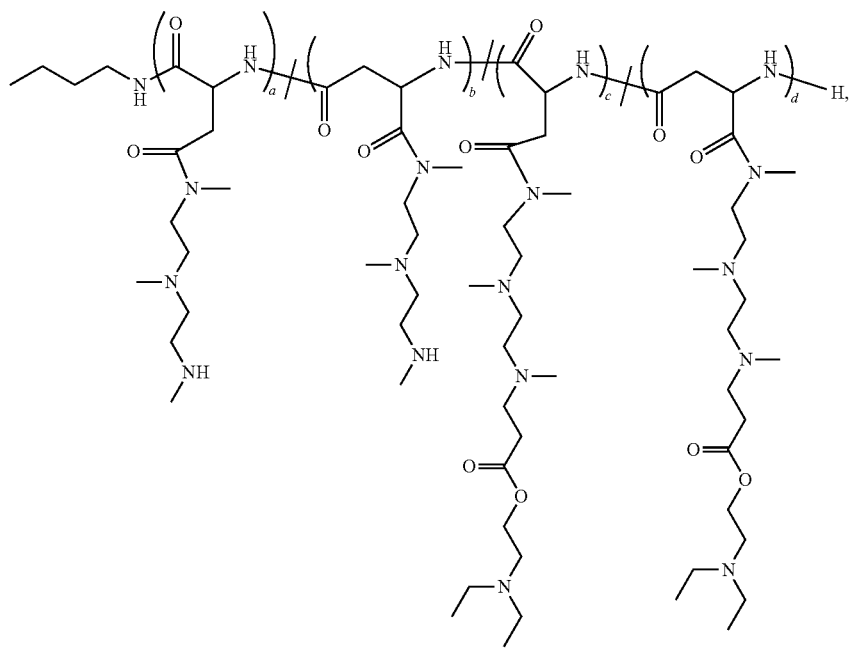
Polymer 15
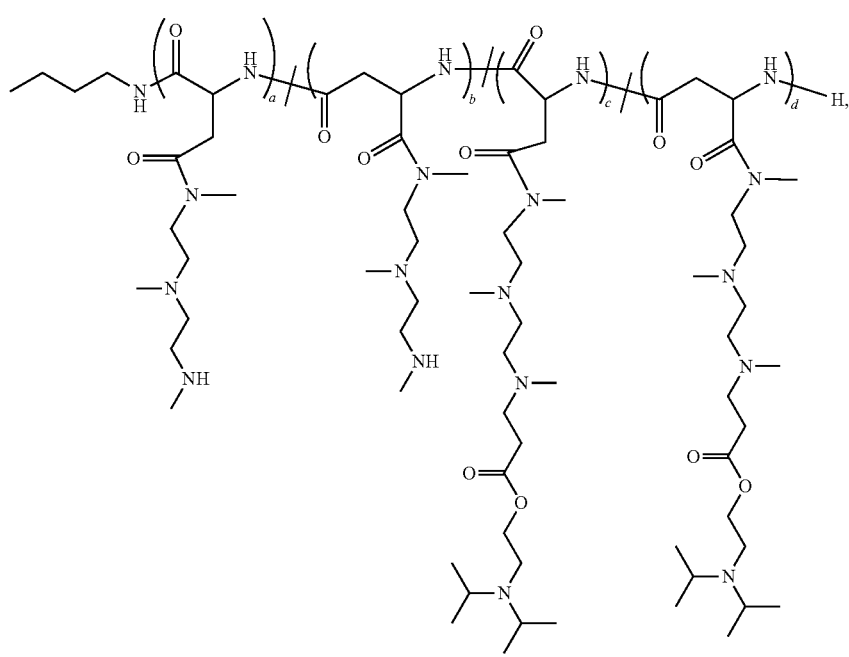

-continued
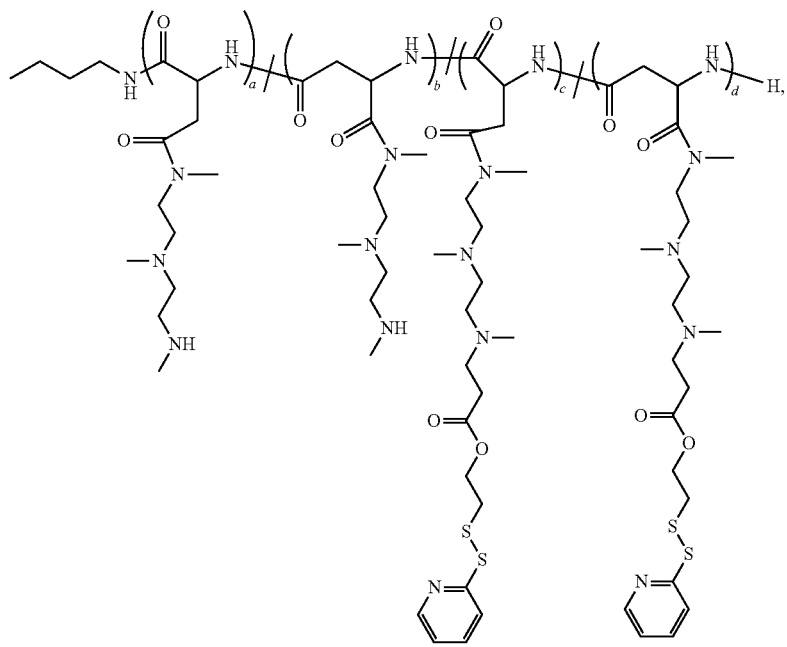
Polymer 16
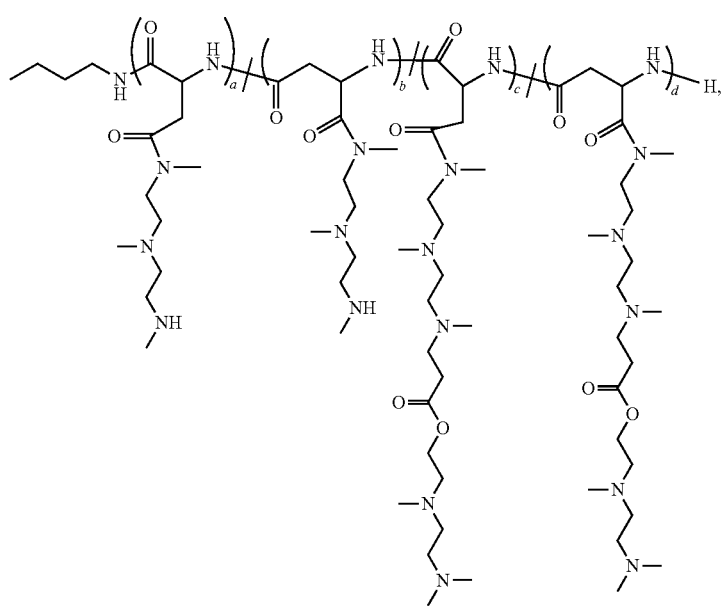
Polymer 17

Polymer 18
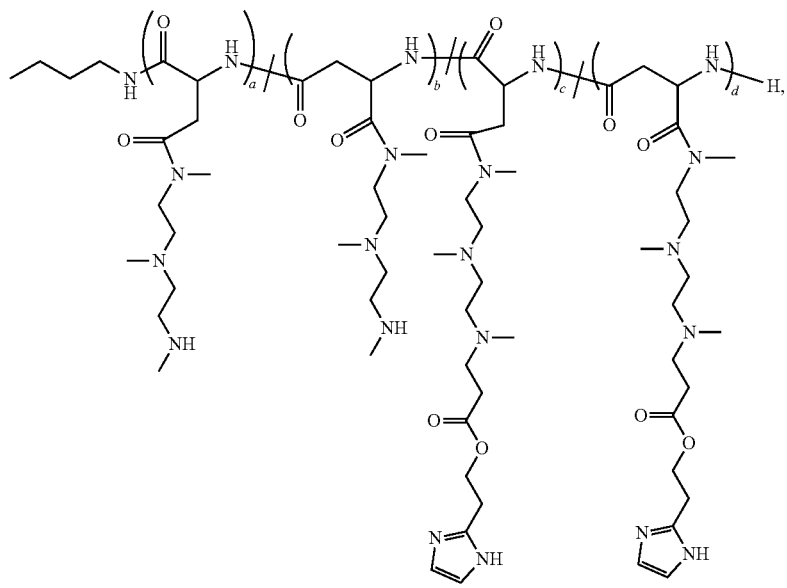
Polymer 19
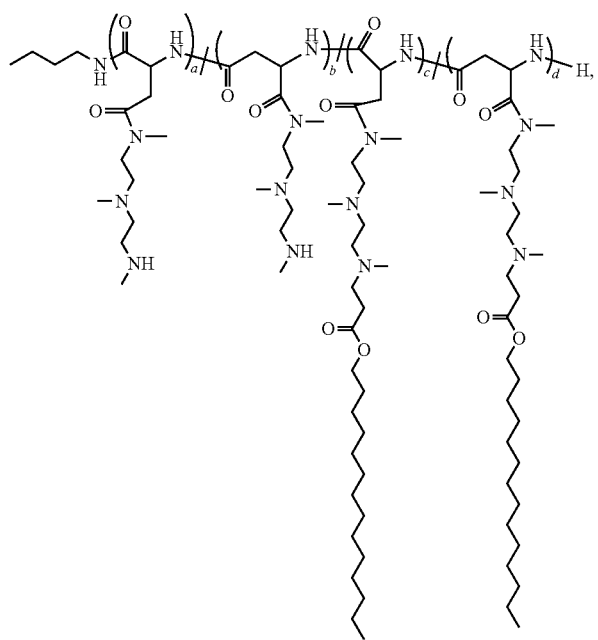

Polymer 20
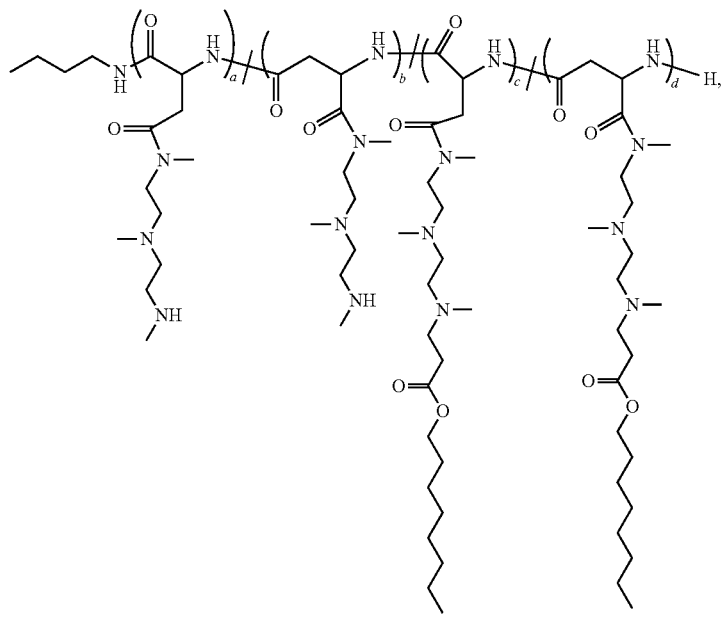
Polymer 21
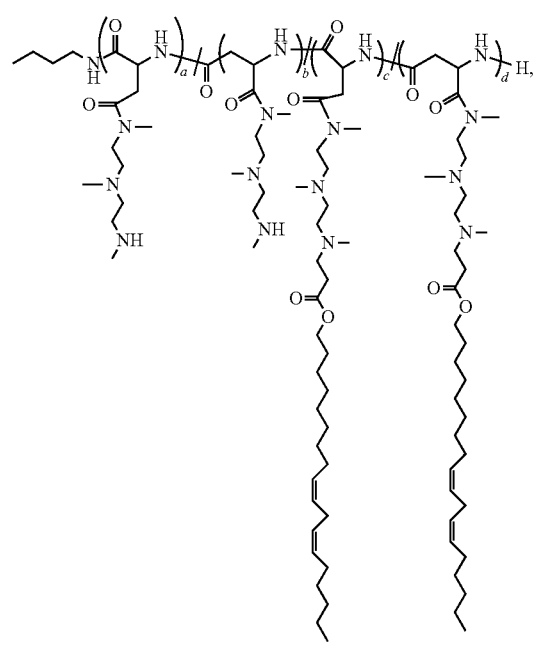

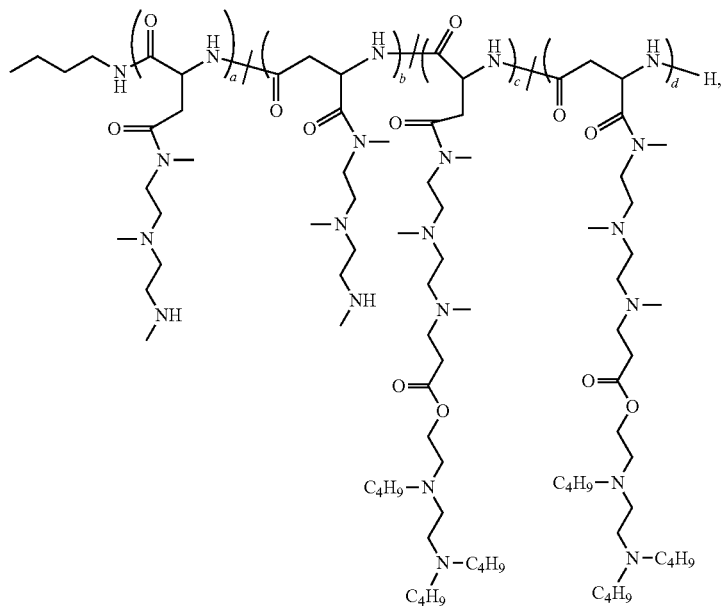
Polymer 22
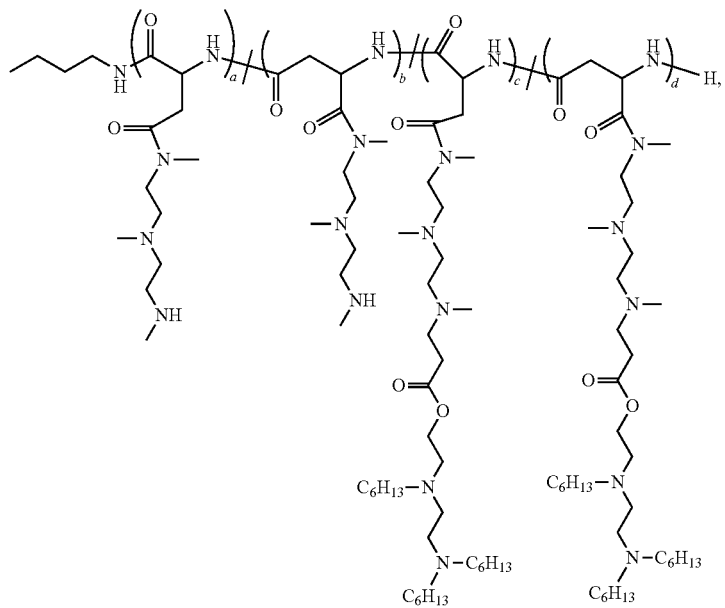
Polymer 23

Polymer 24
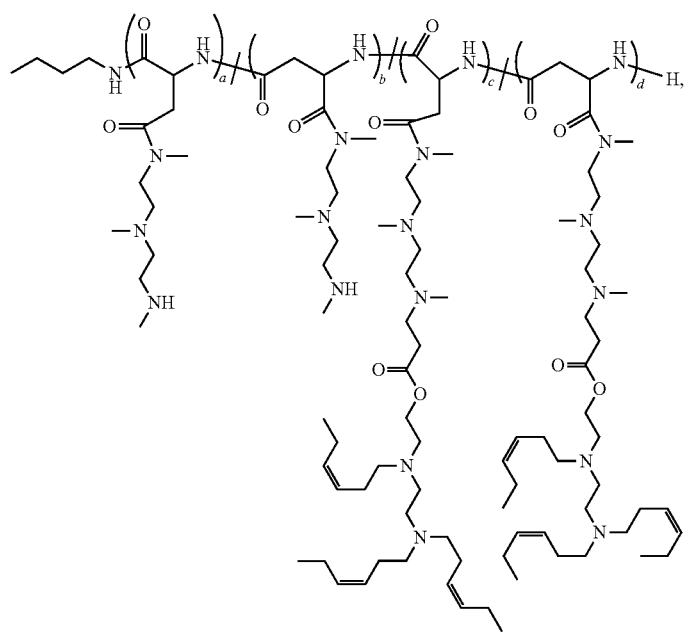
Polymer 28
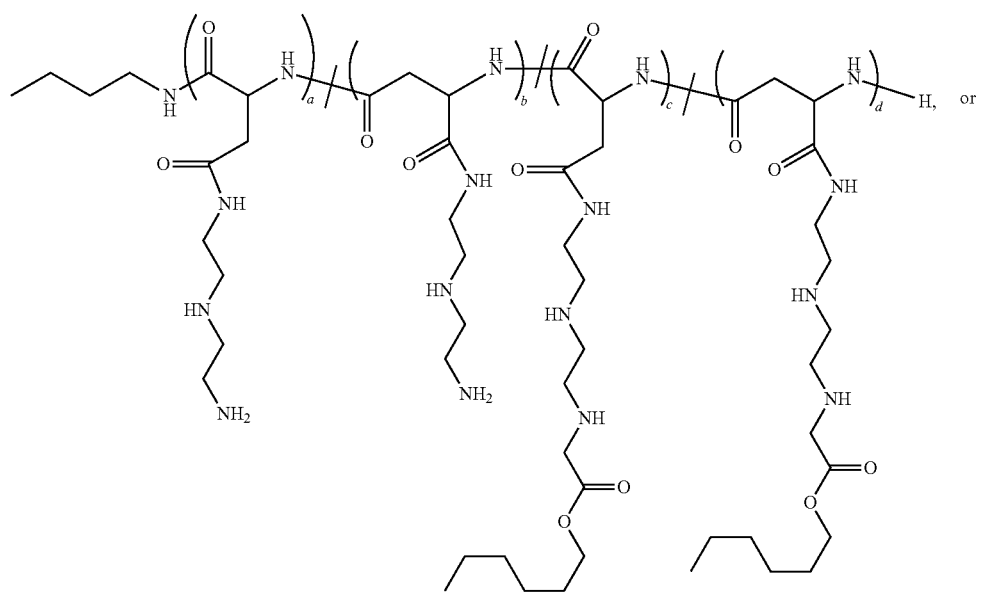
or

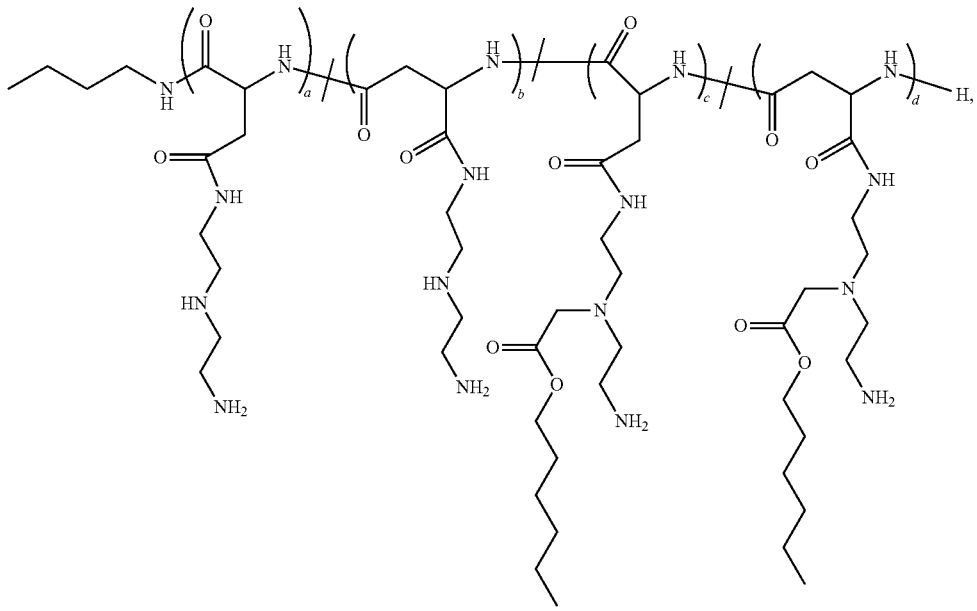

Polymer 29 wherein each of a, b, c, and d is independently an integer from 0 to 1000, such as 0-500, 0-200, 0-100, or 0-50, provided that (a+b+c+d)>about 5. In some embodiments, (a+b) is from about 0 to about 75 (e.g., about 5 to about 75, about 20 to about 75, about 40 to about 75, about 40 to about 60, about 50 to about 75, about 60 to about 75, or about 70 to about 75), and (c+d) is from about 5 to about 80 (e.g., about 5 to about 75, about 5 to about 60, about 5 to about 40, about 20 to about 40, about 5 to about 30, about 5 to about 20, or about 5 to about 10). In certain embodiments, (a+b) is greater than (c+d). For instance, in some embodiments, the ratio of (a+b)/(c+d) is from about 1 to about 3 (e.g., (a+b) is about 55 and (c+d) is about 25), or the ratio of (a+b)/(c+d) is from about 3 to about 10 (e.g., (a+b) is about 70 and (c+d) is about 10). In other embodiments, (a+b) is less than (c+d) such that the ratio of (a+b)/(c+d) is less than 1 (e.g., about 0.1 or more, but less than 1). Again, the indication of the number of units ("a", "b", "c", and "d") in these exemplary polymers does not imply a block co-polymer structure; rather, these numbers indicate the number of units overall, which units can be randomly arranged as indicated by the "/" symbols in the formulas.

The invention also provides a polymer comprising a structure of Formula 2:

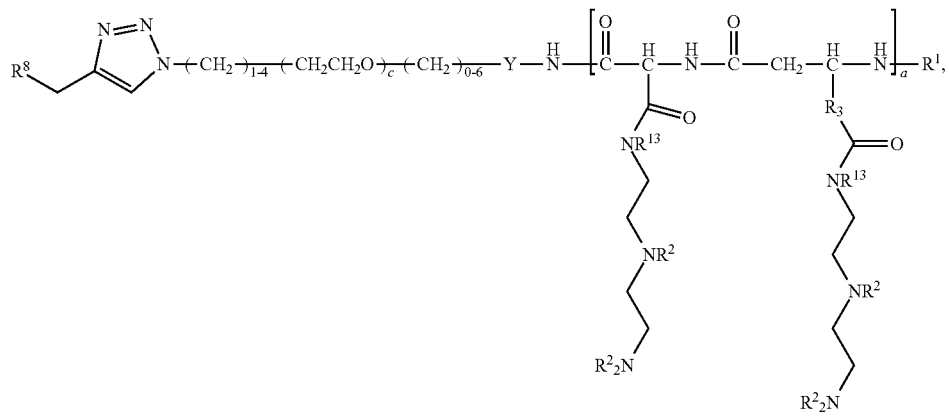

wherein:
 a is an integer from 10 to 2,000;
 c is an integer from 0 to 50;
 Y is optionally present and is a cleavable linker as previously described herein;
 $R^1$, $R^2$, and $R^{13}$ and all other substituent groups are as previously described herein with respect to the other polymer formulas (e.g., Formulas 1, 1A, 1A1, 1.1A, and 1.2A;
 and $R^8$ is a is a tissue-specific or cell-specific targeting moiety.

The invention also provides a polymer comprising a structure of Formula 4:

45

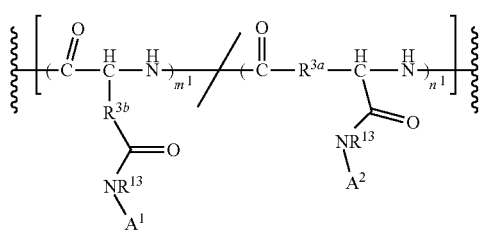

wherein,
each of $m^1$ and $n^1$ is an integer from 0 to 1000; provided that the sum of $m^1+n^1$ is greater than 2;
the symbol "/" indicates that the units separated thereby are linked randomly or in any order;
$A^1$ and $A^2$ are each independently a group of formula

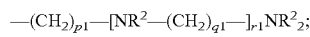

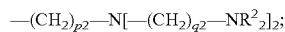

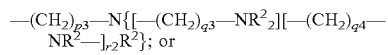

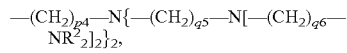

wherein p1 to p4, q1 to q6, and r1 and r2 are each independently an integer of 1 to 5;
each instance of $R^2$ is independently hydrogen, a $C_1$-$C_{12}$ alkyl group, $C_1$-$C_{12}$ alkenyl group, $C_3$-$C_{12}$ cycloalkyl group, or $C_3$-$C_{12}$ cycloalkenyl group, provided that $A^1$ and $A^2$ comprise at least one (e.g., at least two, at least three, at least four, or even at least five tertiary amines (e.g., at least some instances of $R^2$ are a $C_1$-$C_{12}$ alkyl group, alkenyl group, cycloalkyl group, or cycloalkenyl group);
$R^{3a}$ and $R^{3b}$ are each independently a methylene or ethylene group; and
each instance of $R^{13}$ is independently hydrogen or a $C_1$-$C_{12}$ alkyl group, alkenyl group, cycloalkyl group, or cycloalkenyl group.

The invention further provides a polymer having the structure of Formula 4A:

46

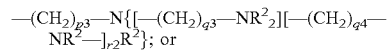

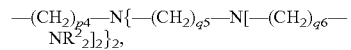

wherein p1 to p4, q1 to q6, and r1 and r2 are each independently an integer of 1 to 5;
$R^1$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents;
each instance of $R^2$ is independently hydrogen, a $C_1$-$C_{12}$ alkyl group, $C_1$-$C_{12}$ alkenyl group, $C_3$-$C_{12}$ cycloalkyl group, or $C_3$-$C_{12}$ cycloalkenyl group, provided that $A^1$ and $A^2$ comprise at least one (e.g., at least two, at least three, at least four, or even at least five tertiary amines (e.g., at least some instances of $R^2$ are a $C_1$-$C_{12}$ alkyl group, alkenyl group, cycloalkyl group, or cycloalkenyl group);
$R^{3a}$ and $R^{3a}$ are each independently a methylene or ethylene group;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety; and
each instance of $R^{13}$ is independently hydrogen or a $C_1$-$C_{12}$ alkyl group, alkenyl group, cycloalkyl group, or cycloalkenyl group.

In embodiments of polymers comprising a structure of Formula 4 and polymers having the structure of Formula 4A, each instance of $R^2$ is independently hydrogen or a $C_1$-$C_{12}$ alkyl group, $C_1$-$C_{12}$ alkenyl group, $C_3$-$C_{12}$ cycloalkyl group, or $C_3$-$C_{12}$ cycloalkenyl group, provided that $A^1$ and $A^2$ each comprise at least one tertiary amine (e.g., at least two, at least three, at least four, or even at least five tertiary amines). In some embodiments, each instance of $R^2$ is independently a $C_1$-$C_{12}$ alkyl group, alkenyl group, cycloalkyl group, or cycloalkenyl group. Accordingly, in embodiments of polymers comprising a structure of Formula 4 and polymers

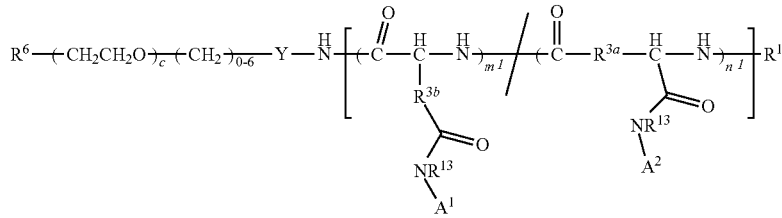

wherein,
c is an integer from 0 to 50;
Y is optionally present and is a cleavable linker;
each of $m^1$ and $n^1$ is an integer from 0 to 1000; provided that the sum of $m^1+n^1$ is greater than 2;
the symbol "/" indicates that the units separated thereby are linked randomly or in any order;
$A^1$ and $A^2$ are each independently a group of formula

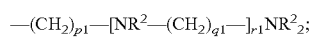

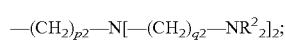

having the structure of Formula 4A, each nitrogen containing $R^2$ substituents is a tertiary amine, except that the terminal amine can be a primary, secondary, or tertiary amine, preferably a secondary or tertiary amine. In some embodiemnts of polymers comprising a structure of Formula 4 and polymers having the structure of Formula 4A, each of $A^1$ and $A^2$ is a group of formula —$(CH_2)_2$—$NR^2$—$(CH_2)_2$—$NR^2_2$, wherein each instance of $R^2$ is independently a $C_1$-$C_{12}$ alkyl group, alkenyl group, cycloalkyl group, or cycloalkenyl group, except that the terminal amine can be a primary, secondary, or tertiary amine, preferably a secondary or tertiary amine. In certain embodiments of polymers comprising a structure of Formula 4 and polymers having the structure of Formula 4A, each instance of $R^2$ is ethyl or methyl, optionally with the exception that the terminal amine can be a primary, secondary, or tertiary amine, preferably a secondary or tertiary amine.

In embodiments of polymers comprising a structure of Formula 4 and polymers having the structure of Formula 4A, each instance of $R^{13}$ is independently hydrogen or a $C_1$-$C_{12}$ alkyl group, alkenyl group, cycloalkyl group, or cycloalkenyl group. Generally, each instance of $R^{13}$ is independently hydrogen or a methyl substituent. In certain embodiments, each instance of $R^{13}$ is hydrogen.

According to any of the foregoing, examples of groups $A^1$ and $A^2$ include, for instance, —NH—$CH_2$—$CH_2$—N($CH_3$)—$CH_2$—$CH_2$—N($CH_3$)$_2$; —N($CH_3$)—$CH_2$—$CH_2$—N($CH_3$)—$CH_2$—$CH_2$—N($CH_3$)$_2$; —NH—$CH_2$—$CH_2$—N($CH_3$)—$CH_2$—$CH_2$—N($CH_3$)—$CH_2$—$CH_2$—N($CH_3$)$_2$; —N($CH_3$)—$CH_2$—$CH_2$—N($CH_3$)—$CH_2$—$CH_2$—N($CH_3$)—$CH_2$—$CH_2$—N($CH_3$)$_2$; —NH—$CH_2$—$CH_2$—N($CH_3$)—$CH_2$—$CH_2$—NH($CH_3$); —N($CH_3$)—$CH_2$—$CH_2$—N($CH_3$)—$CH_2$—$CH_2$—NH($CH_3$); —NH—$CH_2$—$CH_2$—N($CH_3$)—$CH_2$—$CH_2$—N($CH_3$)—$CH_2$—$CH_2$—NH($CH_3$); —N($CH_3$)—$CH_2$—$CH_2$—N($CH_3$)—$CH_2$—$CH_2$—N($CH_3$)—$CH_2$—$CH_2$—NH($CH_3$).

Non-limiting examples of the polymers provided herein, thus, include, for instance:

Polymer 30

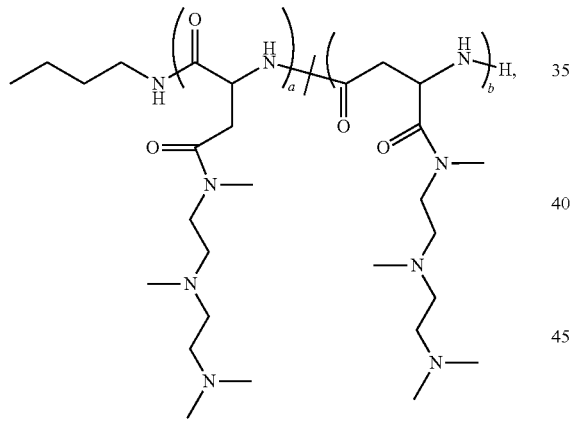

Polymer 31

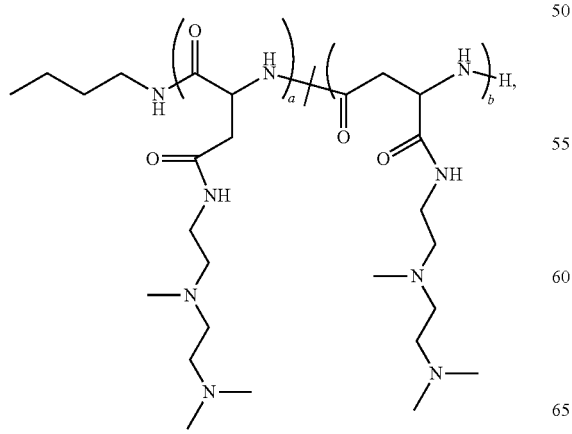

Polymer 32

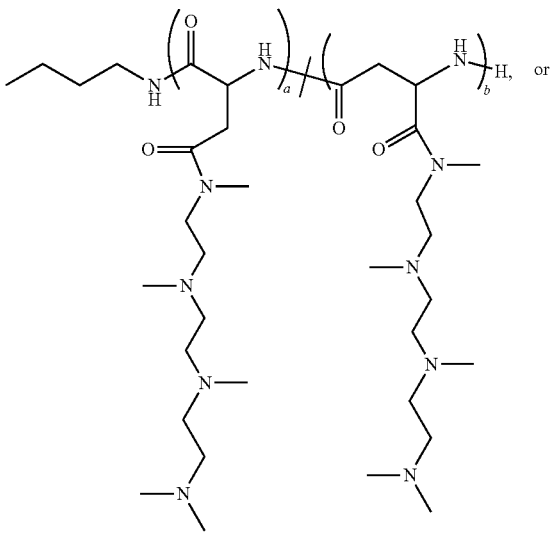

or

Polymer 33

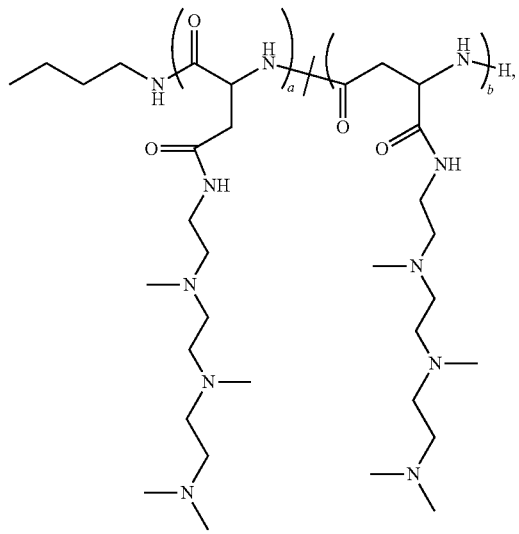

Polymer 37

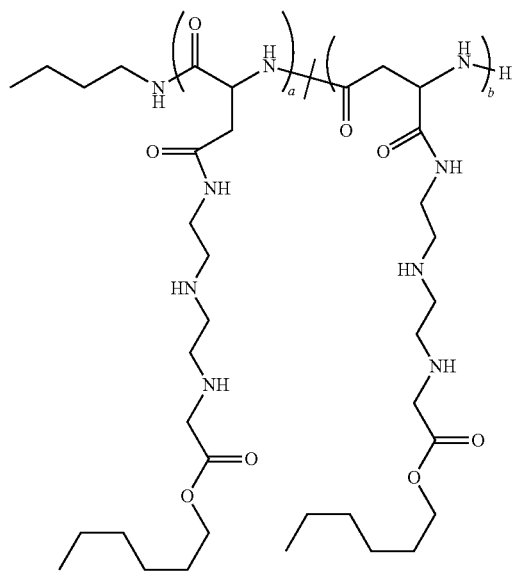

Polymer 38

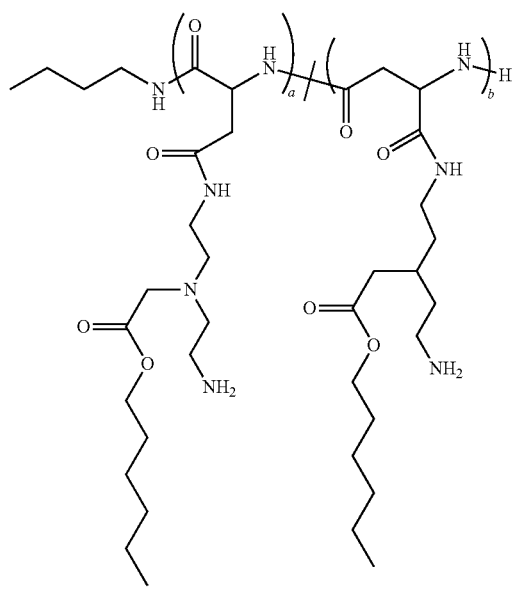

Polymer 39

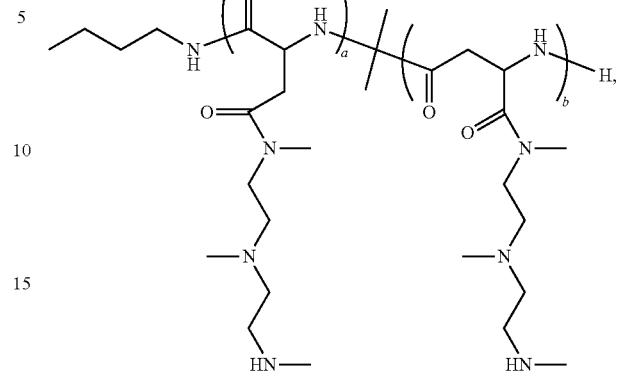

Polymer 40

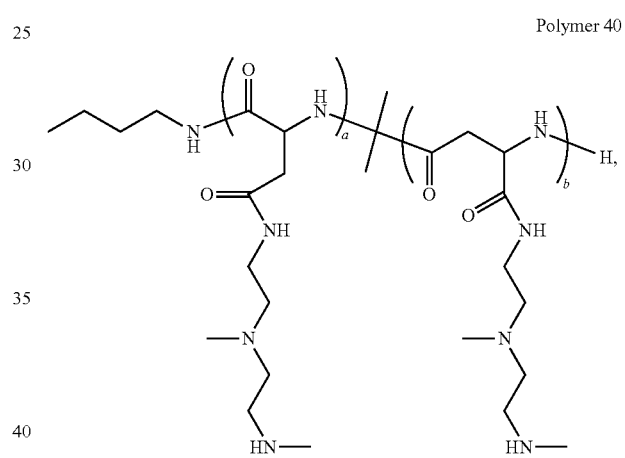

Polymer 41

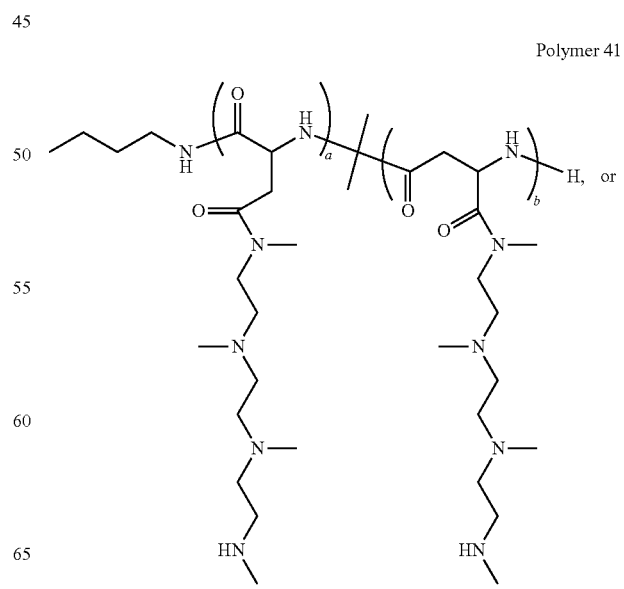

wherein each of a and b is independently an integer from 0 to 1000, such as 0-500, 0-200, 0-100, or 0-50. Thus, either a or b might be 0 in some embodiments, or the polymer might have some ratio of a and b. In some embodiments, (a+b) is about 5 or more (e.g., from about 5 to about 160, about 5 to about 140, about 5 to about 120, about 5 to about 100, about 5 to about 80, or about 5 to about 60) or about 25 or more (e.g., about 25 to about 160, about 25 to about 140, about 25 to about 120, about 25 to about 100, about 25 to about 80, or about 25 to about 60) or even about 50 or more (e.g., about 50 to about 160, about 50 to about 140, about 50 to about 120, about 50 to about 100, or about 50 to about 80). Further examples include polymers 30-33, wherein the terminal tertiary amine of one or both side chains is demethylated to provide a secondary amine (e.g., —NHCH$_3$):

-continued

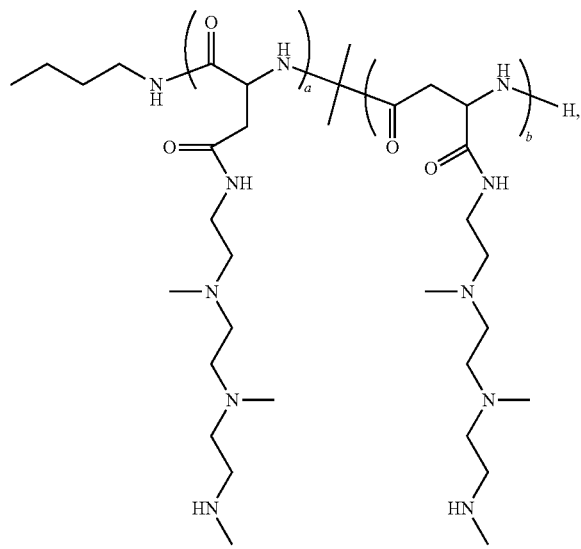

Polymer 42 wherein a and b are as described above.

Any of the forgoing polymers can comprise a tissue-specific or cell-specific targeting moiety at a position indicated in the described formulas, or the polymers can be otherwise modified to include a tissue-specific or cell-specific targeting moiety. Methods for attaching the tissue-specific or cell-specific targeting moiety are known in the art, some of which include Michael addition, epoxide ring opening, displacement reactions, or "click" chemistry (e.g., CuAAC, SPAAC, SPANC, or reaction of strained alkenes) using tissue-specific or cell-specific targeting moiety with appropriate functional groups. The tissue-specific or cell-specific targeting moiety can be any small molecule, protein (e.g., antibody or antigen), amino acid sequence, sugar, oligonucleotide, metal-based nanoparticle, or combination thereof, capable of recognizing (e.g., specifically binding) a given target tissue or cell (e.g., specifically binding a particular ligand, receptor, or other protein or molecule that allows the targeting moiety to discriminate between the target tissue or cell and other non-target tissues or cells). In some embodiments, the tissue-specific or cell-specific targeting moiety is a receptor for a ligand. In some embodiments, the tissue-specific or cell-specific targeting moiety is a ligand for a receptor.

The tissue-specific or cell-specific targeting moiety can be used to target any desired tissue or cell type. In some embodiments, the tissue-specific or cell-specific targeting moiety localizes the polymer to tissues of the peripheral nervous system, the central nervous system, liver, muscle (e.g., cardiac muscle), lung, bone (e.g., hematopoietic cells), or the eye of the subject. In certain embodiments, the tissue-specific or cell-specific targeting moiety localizes the polymer to tumor cells. For example, the tissue-specific or cell-specific targeting moiety can be a sugar that binds to a receptor on a specific tissue or cell.

In some embodiments, the tissue-specific or cell-specific targeting moiety is:

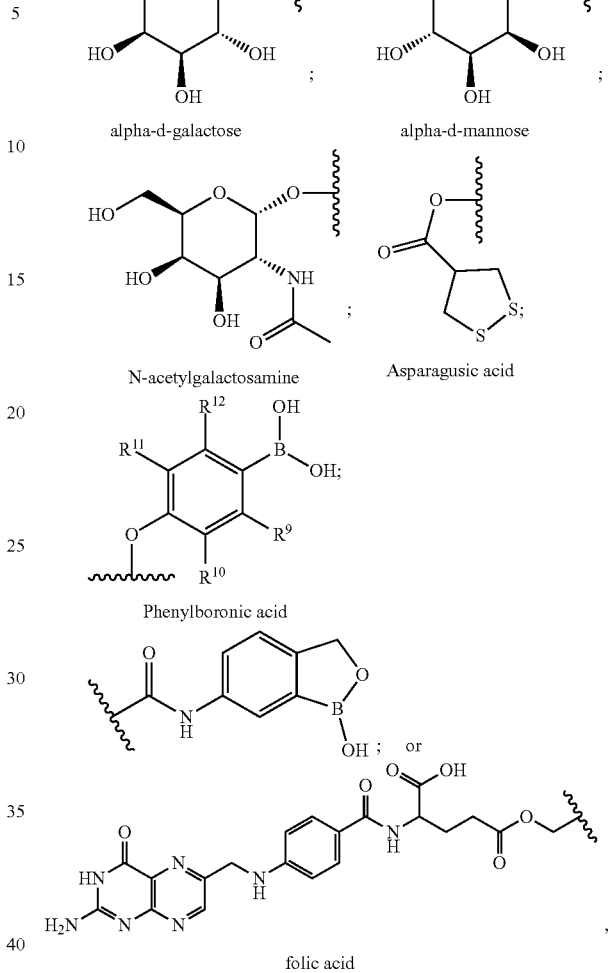

wherein each of $R^9$, $R^{10}$, $R^{11}$, and $R^{12}$ is independently hydrogen, halogen, $C_1$-$C_4$ alkyl, or $C_1$-$C_4$ alkoxy, optionally substituted with one or more amino groups. The specified tissue-specific or cell-specific targeting moieties can be chosen to localize the polymer to a tissue described herein. For example, alpha-d-mannose can be used to localize the polymer to the peripheral nervous system, the central nervous system, or immune cells, alpha-d-galactose and N-acetylgalactosamine can be used to localize the polymer to liver hepatocytes, and folic acid can be used to localize the polymer to tumor cells.

Typically, the polymer is cationic (i.e., positively charged at pH 7 and 23° C.). As used herein, "cationic" polymers refer to polymers having an overall net positive charge, whether the polymer comprises only cationic monomer units or a combination of cationic monomer units and non-ionic or anionic monomer units.

In certain embodiments, the polymer has a weight average molecular weight of from about 5 kDa to about 2000 kDa, such as about 10 kDa to about 2,000 kDa. The polymer can have a weight average molecular weight of about 2,000 kDa or less, for example, about 1,800 kDa or less, about 1,600 kDa or less, about 1,400 kDa or less, about 1,200 kDa or less, about 1,000 kDa or less, about 900 kDa, or less, about 800 kDa, or less, about 700 kDa or less, about 600 kDa or less, about 500 kDa or less, about 100 kDa or less, or about 50 kDa or less or even about 40 kDa or less, such as about 30 kDa or less or 25 kDa or less. Alternatively, or in addition, the polymer can have a weight average molecular weight of about 5 kDa or more or about 10 kDa or more, for example, about 50 kDa or more, about 100 kDa or more, about 200 kDa or more, about 300 kDa or more, or about 400 kDa or more. Thus, the polymer can have a weight average molecular weight bounded by any two of the aforementioned endpoints. For example, the polymer can have a weight average molecular weight of from about 5 kDa to about 50 kDa, about 10 kDa to about 50 kDa, from about, from about 10 kDa to about 100 kDa, from about 10 kDa to about 500 kDa, from about 50 kDa to about 500 kDa, from about 100 kDa to about 500 kDa, from about 200 kDa to about 500 kDa, from about 300 kDa to about 500 kDa, from about 400 kDa to about 500 kDa, from about 400 kDa to about 600 kDa, from about 400 kDa to about 700 kDa, from about 400 kDa to about 800 kDa, from about 400 kDa to about 900 kDa, from about 400 kDa to about 1,000 kDa, from about 400 kDa to about 1,200 kDa, from about 400 kDa to about 1,400 kDa, from about 400 kDa to about 1,600 kDa, from about 400 kDa to about 1,800 kDa, from about 400 kDa to about 2,000 kDa, from about 200 kDa to about 2,000 kDa, from about 500 kDa to about 2,000 kDa, or from about 800 kDa to about 2,000 kDa.

The weight average molecular weight can be determined by any suitable technique. Generally, the weight average molecular weight is determined using size exclusion chromatography equipped with a column, selected from TSKgel Guard, GMPW, GMPW, G1000PW, and a Waters 2414 (Waters Corporation, Milford, Mass.) refractive index detector. Moreover, the weight average molecular weight is determined from calibration with polyethylene oxide/polyethylene glycol standards ranging from 150-875,000 Daltons.

Methods of Preparation

The polymers provided herein can be provided by any suitable method. In some embodiments, the polymers can be prepared by a method that comprises modifying at least a portion of groups $A^1$ and/or $A^2$ of a polymer comprising a structure of Formula 3:

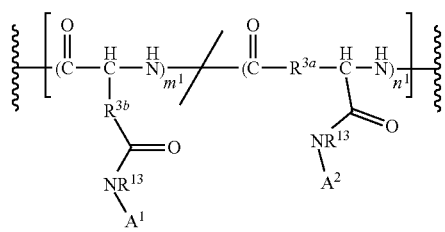

wherein:
each of $m^1$ and $n^1$ is an integer from 0 to 1000, provided that $m^1+n^1$ is greater than 5;
the symbol "/" indicates that the units separated thereby are linked randomly or in any order;
$R^{3a}$ and $R^{3b}$ are each independently a methylene or ethylene group;
each instance of $R^{13}$ is independently hydrogen or a $C_1$-$C_{12}$ alkyl group, alkenyl group, cycloalkyl group, or cycloalkenyl group;

$A^1$ and $A^2$ are each independently a group of formula

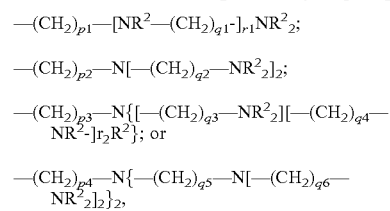

wherein p1 to p4, q1 to q6, and r1 and r2 are each independently an integer of 1 to 5;
and each instance of $R^2$ is independently hydrogen or a $C_1$-$C_{12}$ alkyl group, alkenyl group, cycloalkyl group, or cycloalkenyl group,
to produce a polymer comprising a structure of Formula 1:

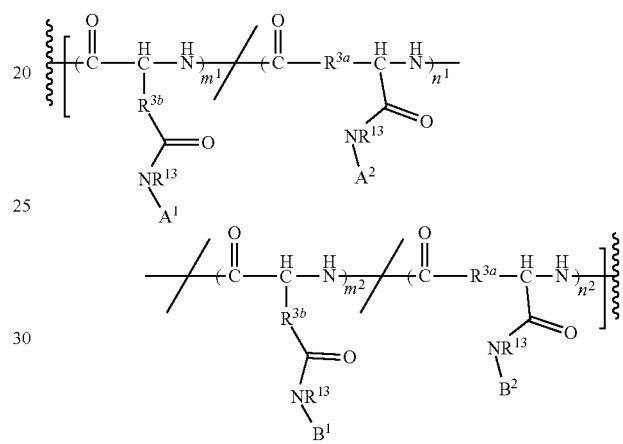

wherein $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
$R^{3a}$ and $R^{3b}$ are each independently a methylene or ethylene group;
each instance of $R^{13}$ is independently hydrogen or a $C_1$-$C_{12}$ alkyl group, alkenyl group, cycloalkyl group, or cycloalkenyl group;
$A^1$ and $A^2$ are each independently a group of formula

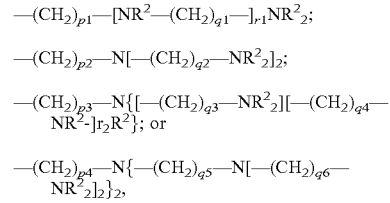

$B^1$ and $B^2$ are each independently

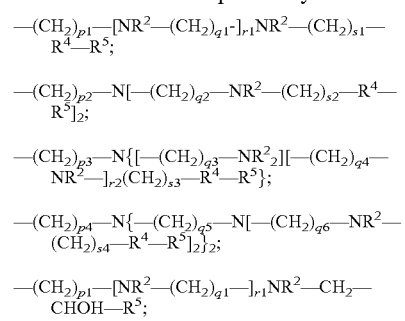

—$(CH_2)_{p2}$—$N[$—$(CH_2)_{q2}$—$NR^2$—$CH_2$—$CHOH$—$R^5]_2$;

—$(CH_2)_{p3}$—$N\{[$—$(CH_2)_{q3}$—$NR^2_2][$—$(CH_2)_{q4}$—$NR^2$—$]_{r2}$—$CH_2$—$CHOH$—$R^5\}$;

—$(CH_2)_{p4}$—$N\{$—$(CH_2)_{q5}$—$N[$—$(CH_2)_{q6}$—$NR^2$—$CH_2$—$CHOH$—$R^5]_2\}_2$;

—$(CH_2)_{p1}$—$[NR^2$—$(CH_2)_{q1}$-$]_{r1}NR^2$—$(CH_2)_{s1}$—$R^5$;

—$(CH_2)_{p2}$—$N[$—$(CH_2)_{q2}$—$NR^2$—$(CH_2)_{s2}$—$R^5]_2$;

—$(CH_2)_{p3}$—$N\{[$—$(CH_2)_{q3}$—$NR^2_2][$—$(CH_2)_{q4}$—$NR^2$—$]_{r2}(CH_2)_{s3}$—$R^5\}$;

—$(CH_2)_{p4}$—$N\{$—$(CH_2)_{q5}$—$N[$—$(CH_2)_{q6}$—$NR^2$—$(CH_2)_{s4}$—$R^5]_2\}_2$;

—$(CH_2)_{p1}$—$[N\{(CH_2)_{s1}$—$R^4$—$R^5\}$—$(CH_2)_{q1}$-$]_{r1}NR^2_2$; or

—$(CH_2)_{p1}$—$[N\{(CH_2)_{s1}$—$R^5\}$—$(CH_2)_{q1}$-$]_{r1}NR^2_2$, wherein p1 to p4, q1 to q6, r1 and r2, and s1 to s4 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O) NH—, or —S(O)(O)—; and each instance of $R^5$ is independently an alkyl group, cycloalkyl group, alkenyl group, cycloalkenyl group, aryl group, heteroalkyl group, heterocyclic group, or combination thereof optionally comprising from 1 to 8 or 2 to 8 secondary or tertiary amines or a substituent comprising a tissue-specific or cell-specific targeting moiety.

The polymer comprising a structure of Formula 1 produced by the method can be any polymer of Formula 1, including Formulas 1.1, 1.2, 1A1, 1A, 1.1A, 1.2A, 4, or 4A as well as any and all embodiments thereof as described with respect to the polymer of the invention.

The polymer comprising a structure of Formula 3 can be any suitable polymer meeting this criteria. In some embodiments, the polymer could instead be described as Formula 3.1:

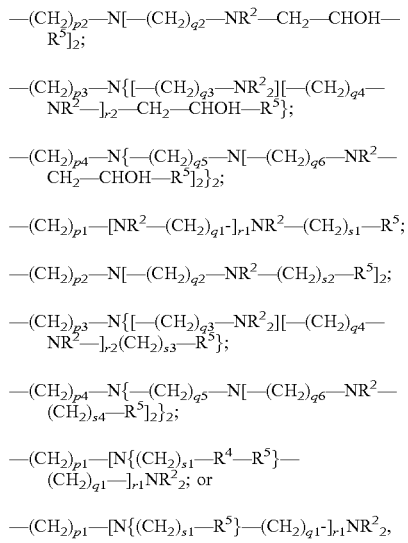

or, where the backbone is in an alpha, beta configuration, as Formula 3.2:

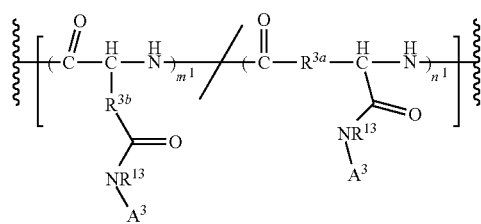

wherein,
$m^3$ is an integer from 5-2000 (e.g., 5-1000, 5-500, 5-100, 25-2000, 25-500, 25-100, 50-2000, 50-1000, 50-500, or 50-100);
the symbol "/" indicates that the units separated thereby are linked randomly or in any order;
$R^{3a}$ and $R^{3b}$ are each independently a methylene or ethylene group;
each instance of $R^{13}$ is independently hydrogen or a $C_1$-$C_{12}$ alkyl group, alkenyl group, cycloalkyl group, or cycloalkenyl group;
each $A^3$ is independently a group of formula —$(CH_2)_{p1}$—$[NR^2$—$(CH_2)_{q1}$—$]_{r1}NR^2_2$;

—$(CH_2)_{p2}$—$N[$—$(CH_2)_{q2}$—$NR^2_2]_2$;

—$(CH_2)_{p3}$—$N\{[$—$(CH_2)_{q3}$—$NR^2_2][$—$(CH_2)_{q4}$—$NR^2$—$]_{r2}R^2\}$; or

—$(CH_2)_{p4}$—$N\{$—$(CH_2)_{q5}$—$N[$—$(CH_2)_{q6}$—$NR^2_2]_2\}_2$, wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group. In this case, the method can comprise modifying at least a portion of the $A^3$ groups sufficient to provide a polymer with a structure of Formula 1.1 or 1.2, as described herein. An example of a polymer comprising one of the following structures is pAsp(DET) (poly (2-[(2-aminoethyl)amino] ethyl aspartamide)) or PEG-pAsp(DET) (polyethylene glycol-b-poly{N'—[N-(2-aminoethyl)-2-aminoethyl] aspartamide}).

The groups designated $A^1$ and/or $A^2$ (or group $A^3$ of the polymer of Formula 3.1 or 3.2) can be modified by any suitable means to produce groups designated $B^1$ and/or $B^2$ (or group $A^3$ of the polymer of Formula 1.1 or 1.2). For example, the groups designated $A^1$ and/or $A^2$ (or group $A^3$ of the polymer of Formula 3.1 or 3.2) can be modified by a Michael addition reaction, an epoxide opening, or a displacement reaction. In preferred embodiments, the groups designated $A^1$ and/or $A^2$ (or group $A^3$ of the polymer of Formula 3.1 or 3.2) are modified by a Michael addition reaction.

In one embodiment, groups $A^1$ and/or $A^2$ of the polymer comprising a structure of Formula 3, or group $A^3$ of the polymer of Formula 3.1 or 3.2, are modified by a Michael addition reaction between the polymer comprising the structure of Formula 3 and α,β-unsaturated carbonyl compound. As used herein, the term "Michael addition" refers to a nucleophilic addition of a nucleophile of the polymer (e.g., a carbanion, an oxygen anion, a nitrogen anion, an oxygen atom, a nitrogen atom, or a combination thereof) to an α,β-unsaturated carbonyl compound. Accordingly, the Michael addition reaction is between the polymer comprising the structure of Formula 3 and an α,β-unsaturated carbonyl compound. In some embodiments, the nucleophile of the polymer is a nitrogen anion, a nitrogen atom, or a combination thereof.

The α,β-unsaturated carbonyl compound can be any α,β-unsaturated carbonyl compound capable of accepting a Michael addition from a nucleophile. In some embodiments, the α,β-unsaturated carbonyl compound is an acrylate, an acrylamide, a vinyl sulfone, or a combination thereof. Accordingly, the Michael addition reaction can be between the polymer comprising the structure of Formula 3 and an acrylate, an acrylamide, a vinyl sulfone, or a combination thereof. Thus, in some embodiments, the method comprises contacting the polymer comprising the structure of Formula 3 and an acrylate; contacting the polymer comprising the structure of Formula 3 and an acrylamide; or contacting the polymer comprising the structure of Formula 3 and a vinyl sulfone.

In embodiments where the groups designated $A^1$ and/or $A^2$ (or group $A^3$ of the polymer of Formula 3.1 or 3.2) are modified by a Michael addition reaction, they produce groups designated $B^1$ and/or $B^2$ as described herein with respect to Formula 1, 1.1., 1.2, 1A, $1A^1$, etc. (or group $A^3$ of the polymer of Formula 1.1 or 1.2). For instance, $B^1$ and/or $B^2$ can be of the formula:

—$(CH_2)_{p1}$—[$NR^2$—$(CH_2)_{q1}$—]$_{r1}NR^2$—$(CH_2)_{s1}$—$R^4$—$R^5$;

—$(CH_2)_{p2}$—N[—$(CH_2)_{q2}$—$NR^2$—$(CH_2)_{s2}$—$R^4$—$R^5$]$_2$;

—$(CH_2)_{p3}$—N{[—$(CH_2)_{q3}$—$NR^2_2$][—$(CH_2)_{q4}$—$NR^2$—]$_{r2}(CH_2)_{s3}$—$R^4$—$R^5$};

—$(CH_2)_{p4}$—N{—$(CH_2)_{q5}$—N[—$(CH_2)_{q6}$—$NR^2$—$(CH_2)_{s4}$—$R^4$—$R^5$]$_2$}$_2$, wherein p1 to p4, q1 to q6, r1 and r2, and s1 to s4 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, heterocyclic group, or combination thereof optionally comprising from 1 to 8 or 2 to 8 secondary or tertiary amines or a substituent comprising a tissue-specific or cell-specific targeting moiety; or the groups and substituents can be otherwise as described herein with respect to the polymers of the invention.

Examples of acrylates, acrylamides, and vinyl sulfones suitable for use include an Acrylate of the formula:

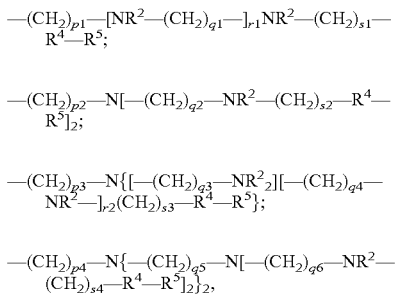

wherein $R^5$ is as described with respect to any of Formulas 1, 1.1, 1.2, 1A, 1.1A, or 1.2A.

In some embodiments, the Michael addition reaction is facilitated by an acid and/or base. The acid and/or base can be any suitable acid and/or base with any suitable pKa. The acid and/or base can be an organic acid (e.g., p-toluenesulfonic acid), organic base (e.g., triethylamine), inorganic acid (e.g., titanium tetrachloride), inorganic base (e.g., potassium carbonate), or a combination thereof.

In some embodiments, the Michael addition reaction is facilitated by an acid. The acid can be a Brønsted acid or a Lewis acid. In embodiments where the acid is a Brønsted acid, the acid can be a weak acid (i.e., a pKa of from about 4 to about 7) or a strong acid (i.e., a pKa of from about −2 to about 4). Typically, the acid is a weak acid. In certain embodiments, the acid is a Lewis acid. For example, the acid can be bis(trifluoromethanesulfon)imide or p-toluenesulfonic acid.

In some embodiments, the Michael addition reaction is facilitated by a base. The base can be a weak base (i.e., a pKa of from about 7 to about 12) or a strong base (i.e., a pKa of from about 12 to about 50). Typically, the base is a weak base. For example, the base can be triethylamine, diisopropylethylamine, pyridine, N-methyl morpholine, or N,N-dimethyl-piperazine, or derivatives thereof.

In some embodiments, the Michael addition reaction is performed in a solvent. The solvent can be any suitable solvent, or mixture of solvents, capable of solubilizing the polymer and the α,β-unsaturated carbonyl compound to be reacted. For example, the solvent can include water, protic organic solvents, and/or aprotic organic solvents. An exemplary list of solvents includes water, dichloromethane, diethyl ether, dimethyl sulfoxide, acetonitrile, methanol, and ethanol.

In one embodiment, groups $A^1$ and/or $A^2$ (or group $A^3$ of the polymer of Formula 3.1 or 3.2) of the polymer are modified by an epoxide opening reaction between the polymer and an epoxide compound. As used herein, the term "epoxide opening" refers to a nucleophilic addition of a nucleophile of the polymer (e.g., a carbanion, an oxygen anion, a nitrogen anion, an oxygen atom, a nitrogen atom, or a combination thereof) to an epoxide compound, thereby opening the epoxide. Accordingly, the epoxide opening reaction is between the polymer and an epoxide compound. In some embodiments, the nucleophile of the polymer is a nitrogen anion, a nitrogen atom, or a combination thereof.

In embodiments where the groups designated $A^1$ and/or $A^2$ (or group $A^3$ of the polymer of Formula 3.1 or 3.2) are modified by an epoxide opening reaction, they produce groups designated $B^1$ and/or $B^2$ (or group $A^3$ of the polymer of Formula 1.1 or 1.2) of the formula:

—$(CH_2)_{p1}$—[$NR^2(CH_2)_{q1}$—]$_{r1}NR^2$—$CH_2$—CHOH—$R^5$;

—$(CH_2)_{p2}$—N[—$(CH_2)_{q2}$—$NR^2$—$CH_2$—CHOH—$R^5$]$_2$;

—$(CH_2)_{p3}$—N{[—$(CH_2)_{q3}$—$NR^2_2$][—$(CH_2)_{q4}$—$NR^2$—]$_{r2}$—$CH_2$—CHOH—$R^5$};

—$(CH_2)_{p4}$—N{—$(CH_2)_{q5}$—N[—$(CH_2)_{q6}$—$NR^2$—$CH_2$—CHOH—$R^5$]$_2$}$_2$, wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; and each instance of $R^5$ is independently an alkyl group, cycloalkyl group, alkenyl group, cycloalkenyl group, aryl group, heteroalkyl group, heterocyclic group, or combination thereof optionally comprising from 1 to 8 or 2 to 8 secondary or tertiary amines or a substituent comprising a tissue-specific or cell-specific targeting moiety.

Examples of epoxides suitable for use include epoxides of the formula:

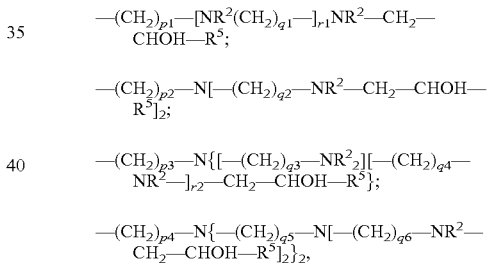

wherein $R^5$ is as described with respect to any of the polymers of the invention (e.g., Formulas 1, 1.1, 1.2, 1A, 1.1A, or 1.2A).

In some embodiments, the epoxide opening reaction is facilitated by an acid and/or base. The acid and/or base can be any suitable acid and/or base with any suitable pKa. The acid and/or base can be an organic acid (e.g., p-toluenesulfonic acid), organic base (e.g., triethylamine), inorganic acid (e.g., titanium tetrachloride), inorganic base (e.g., potassium carbonate), or a combination thereof.

In some embodiments, the epoxide opening reaction is facilitated by an acid. The acid can be a Brønsted acid or a Lewis acid. In embodiments where the acid is a Brønsted acid, the acid can be a weak acid (i.e., a pKa of from about 4 to about 7) or a strong acid (i.e., a pKa of from about −2 to about 4). Typically, the acid is a weak acid. In certain embodiments, the acid is a Lewis acid. For example, the acid can be bis(trifluoromethanesulfon)imide or p-toluenesulfonic acid.

In some embodiments, the epoxide opening reaction is facilitated by a base. The base can be a weak base (i.e., a pKa of from about 7 to about 12) or a strong base (i.e., a pKa of from about 12 to about 50). Typically, the base is a weak base. For example, the base can be triethylamine, diisopropylethylamine, pyridine, N-methyl morpholine, or N,N-dimethyl-piperazine, or derivatives thereof.

In some embodiments, the epoxide opening reaction is performed in a solvent. The solvent can be any suitable solvent, or mixture of solvents, capable of solubilizing the polymer and the epoxide compound to be reacted. For example, the solvent can include water, protic organic solvents, and/or aprotic organic solvents. An exemplary list of solvents includes water, dichloromethane, diethyl ether, dimethyl sulfoxide, acetonitrile, methanol, and ethanol.

In one embodiment, groups $A^1$ and/or $A^2$ (or group $A^3$ of the polymer of Formula 3.1 or 3.2) of the polymer are modified by a displacement reaction between the polymer and a compound comprising a leaving group (e.g., chloride atom, bromide atom, iodide atom, tosylate, triflate, mesylate, etc.). As used herein, the term "displacement" refers to a nucleophilic addition of a nucleophile of the polymer (e.g., a carbanion, an oxygen anion, a nitrogen anion, an oxygen atom, a nitrogen atom, or a combination thereof) to a compound comprising a leaving group. Accordingly, the displacement reaction is between the polymer and a compound comprising a leaving group. In some embodiments, the nucleophile of the polymer is a nitrogen anion, a nitrogen atom, or a combination thereof.

In embodiments where the groups designated $A^1$ and/or $A^2$ (or group $A^3$ of the polymer of Formula 3.1 or 3.2) are modified by a displacement reaction, they produce groups designated $B^1$ and/or $B^2$ (or group $A^3$ of the polymer of Formula 1.1 or 1.2) of the formula:

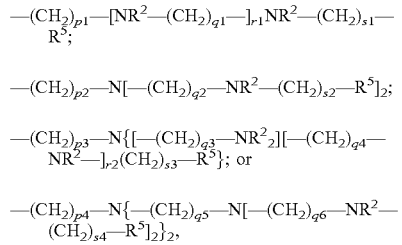

wherein p1 to p4, q1 to q6, r1 and r2, and s to s4 are each independently an integer of 1 to 5; each instance of $R^2$ is independently hydrogen or a $C_1$-$C_{12}$ alkyl group, alkenyl group, cycloalkyl group, or cycloalkenyl group; and each instance of $R^5$ is independently an alkyl group, cycloalkyl group, alkenyl group, cycloalkenyl group, aryl group, heteroalkyl group, heterocyclic group, or combination thereof optionally comprising from 1 to 8 or 2 to 8 secondary or tertiary amines or a substituent comprising a tissue-specific or cell-specific targeting moiety.

In some embodiments, the method comprises preparing a polymer comprising a structure of Formula 5 from a compound of Formula A:

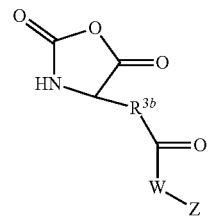

wherein,
$R^{3b}$ is a methylene or ethylene group;
W is —$NR^{14}$— or —O—, wherein $R^{14}$ is hydrogen or a $C_1$-$C_{12}$ alkyl group, alkenyl group, cycloalkyl group, or cycloalkenyl group;
Z is $A^1$, or an alkyl group, cycloalkyl group, alkenyl group, cycloalkenyl group, aryl group, arylalkyl group, heteroalkyl group, heterocyclic group, or combination thereof optionally comprising from 1 to 8 or 2 to 8 secondary or tertiary amines or a substituent comprising a tissue-specific or cell-specific targeting moiety;
$A^1$ is a group of formula

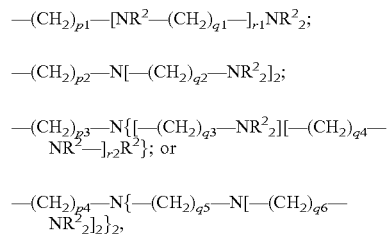

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

Generally, the method comprising forming a polymer comprising a structure of Formula 5 from a compound of Formula A includes a ring-opening polymerization of the compound Formula A. The ring-opening polymerization of the compound of Formula A can be initiated by any suitable method (e.g., temperature, light, catalyst, compound, etc.). In some embodiments, the ring-opening polymerization of the compound of Formula A is initiated with an amine-containing compound.

In certain embodiments, the ring-opening polymerization of the compound of Formula A is initiated with an amine-containing compound of the formula:

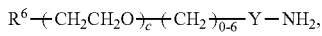

$$R^6\!-\!(\!CH_2CH_2O\!)_{\!c}\!-\!(\!CH_2\!)_{0\text{-}6}\!-\!Y\!-\!NH_2,$$

wherein,
c is an integer from 0 to 50;
Y is optionally present and is a cleavable linker; and
$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety. In preferred embodiments, the amine-containing compound is

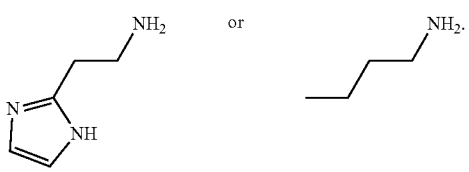

In some embodiments, in the compound of Formula A, Y is —O—, and Z is an alkyl group, cycloalkyl group, alkenyl group, cycloalkenyl group, aryl group, arylalkyl group, heteroalkyl group, heterocyclic group, or combination thereof optionally comprising from 1 to 8 or 2 to 8 secondary or tertiary amines. In some embodiments, Z is an arylalkyl group, such as a benzyl. The method of producing a polymer of Formula 5, then, further comprises, after ring opening polymerization, treating the resulting intermediate polymer with a compound of the formula $NHR^{17}$-$A^1$, wherein $A^1$ is as defined with respect to Formula 1. The compound of the formula $NHR^{17}$-$A^1$ is optionally diethyleneamine triamine. In some embodiments, the compound of formula $NHR^{17}$-$A^1$ is not diethyleneamine triamine.

$R^{17}$ can be hydrogen or a $C_1$-$C_{12}$ alkyl group, alkenyl group, cycloalkyl group, or cycloalkenyl group. In some embodiments, $R^{17}$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group. In certain embodiments, $R^{17}$ is methyl. In other embodiments, $R^{17}$ can be hydrogen. Typically, within a given polymer, each $R^{17}$ is the same (e.g., all methyl or all hydrogen); however, each $R^{17}$ is independently chosen and can be the same or different.

Examples of compounds containing a leaving group suitable for use include compound of formula:

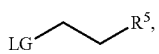

wherein LG is a leaving group (e.g., chloride atom, bromide atom, iodide atom, tosylate, triflate, mesylate, etc.) and $R^5$ is as described with respect to any of Formulas 1, 1.1, 1.2, 1A, 1.1A, or 1.2A.

In some embodiments, the displacement reaction is facilitated by an acid and/or base. The acid and/or base can be any suitable acid and/or base with any suitable pKa. The acid and/or base can be an organic acid (e.g., p-toluenesulfonic acid), organic base (e.g., triethylamine), inorganic acid (e.g., titanium tetrachloride), inorganic base (e.g., potassium carbonate), or a combination thereof.

In some embodiments, the displacement reaction is facilitated by an acid. The acid can be a Brønsted acid or a Lewis acid. In embodiments where the acid is a Brønsted acid, the acid can be a weak acid (i.e., a pKa of from about 4 to about 7) or a strong acid (i.e., a pKa of from about −2 to about 4). Typically, the acid is a weak acid. In certain embodiments, the acid is a Lewis acid. For example, the acid can be bis(trifluoromethanesulfon)imide or p-toluenesulfonic acid.

In some embodiments, the displacement reaction is facilitated by a base. The base can be a weak base (i.e., a pKa of from about 7 to about 12) or a strong base (i.e., a pKa of from about 12 to about 50). Typically, the base is a weak base. For example, the base can be triethylamine, diisopropylethylamine, pyridine, N-methyl morpholine, or N,N-dimethyl-piperazine, or derivatives thereof.

In some embodiments, the displacement reaction is performed in a solvent. The solvent can be any suitable solvent, or mixture of solvents, capable of solubilizing the polymer and the compound comprising a leaving group to be reacted. For example, the solvent can include water, protic organic solvents, and/or aprotic organic solvents. An exemplary list of solvents includes water, dichloromethane, diethyl ether, dimethyl sulfoxide, acetonitrile, methanol, and ethanol.

In some embodiments, the method further comprises isolating the polymer comprising the structure of Formula 1. The polymer comprising the structure of Formula 1 can be isolated by any suitable means. For example, the polymer comprising the structure of Formula 1 can be isolated by extraction, crystallization, recrystallization, column chromatography, filtration, or any combination thereof.

Compositions

The polymers provided herein can be used for any purpose. However, it is believed the polymers are particularly useful for delivering nucleic acids and/or polypeptides (e.g., protein) to cells. Thus, provided herein is a composition comprising a polymer as described herein and a nucleic acid and/or polypeptide (e.g., protein).

In some embodiments, the composition comprises a nucleic acid. Any nucleic acid can be used. An exemplary list of nucleic acids includes guide and/or donor nucleic acids of CRISPR systems, siRNA, microRNA, interfering RNA or RNAi, dsRNA, mRNA, DNA vector, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to a gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited. The polynucleotide also can be a sequence that serves as a "barcode" for purposes such as tracking delivery in vitro or in vivo.

The composition also can comprise any protein for delivery, in addition to or instead of a nucleic acid. The polypeptide can be any suitable polypeptide. For example, the polypeptide can be a zinc finger nuclease, a transcription activator-like effector nuclease ("TALEN"), a recombinase, a deaminase, an endonuclease, or a combination thereof. In some embodiments, the polypeptide is an RNA-guided endonuclease (e.g., a Cas9 polypeptide, a Cpf1 polypeptide, or variants thereof) or a DNA recombinase (e.g., a Cre polypeptide).

It is believed the polymers provided herein are particularly useful for delivering one or more components of a CRISPR system. Thus, in some embodiments, the composition comprises a guide RNA, an RNA-guided endonuclease or nucleic acid encoding same, and/or a donor nucleic acid. The composition can comprise one, two, or all three components together with the polymer described herein. Furthermore, the composition can comprise a plurality of guide RNAs, RNA-guided endonucleases or nucleic acids encoding same, and/or donor nucleic acids. For instance, multiple different guide RNAs for different target sites could be included, optionally with multiple different donor nucleic acids and even multiple different RNA guided endonucleases or nucleic acids encoding same.

Furthermore, the components of the CRISPR system can be combined with one another (when multiple components are present) and the polymer in any particular manner or order. In some embodiments, the guide RNA is complexed with an RNA endonuclease prior to combining with the polymer. In addition, or instead, the guide RNA can be linked (covalently or non-covalently) to a donor nucleic acid prior to combining with the polymer.

The compositions are not limited with respect to any particular CRISPR system (i.e., any particular guide RNA, RNA-guided endonuclease, or donor nucleic acid), many of which are known. Nevertheless, for the sake of further illustration, the components of some such systems are described below.

Donor Nucleic Acid

The donor nucleic acid (or "donor sequence" or "donor polynucleotide" or "donor DNA") is a nucleic acid sequence to be inserted at the cleavage site induced by an RNA-directed endonuclease (e.g., a Cas9 polypeptide or a Cpf1 polypeptide). The donor polynucleotide will contain sufficient homology to a target genomic sequence at the cleavage site, e.g. 70%, 80%, 85%, 90%, 95%, or 100% homology with the nucleotide sequences flanking the cleavage site, e.g. within about 50 bases or less of the cleavage site, e.g. within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some embodiments may be used for other purposes (e.g., to signify expression at the targeted genomic locus). In some embodiments, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad Sci USA 84:4959-4963; Nehls et al. (1996) Science 272:886-889. Amplification procedures such as rolling circle amplification can also be advantageously employed, as exemplified herein. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or polymer, or can be delivered by viruses (e.g., adenovirus, AAV), as described herein for nucleic acids encoding a Cas9 guide RNA and/or a Cas9 fusion polypeptide and/or donor polynucleotide.

Guide Nucleic Acid

In some embodiments, the composition comprises guide nucleic acid. Guide nucleic acids suitable for inclusion in a composition of the present disclosure include single-molecule guide RNAs ("single-guide RNA"/"sgRNA") and dual-molecule guide nucleic acids ("dual-guide RNA"/ "dgRNA").

A guide nucleic acid (e.g., guide RNA) suitable for inclusion in a complex of the present disclosure directs the activities of an RNA-guided endonuclease (e.g., a Cas9 or Cpf1 polypeptide) to a specific target sequence within a target nucleic acid. A guide nucleic acid (e.g., guide RNA) comprises: a first segment (also referred to herein as a "nucleic acid targeting segment", or simply a "targeting segment"); and a second segment (also referred to herein as a "protein-binding segment"). The terms "first" and "second" do not imply the order in which the segments occur in the guide RNA. The order of the elements relative to one another depends upon the particular RNA-guided polypeptide to be used. For instance, guide RNA for Cas9 typically has the protein-binding segment located 3' of the targeting segment, whereas guide RNA for Cpf1 typically has the protein-binding segment located 5' of the targeting segment.

The guide RNA may be introduced into a cell in linear or circular form. If introduced in linear form, the ends of the guide RNA may be protected (e.g., from exonucleolytic degradation) by methods known to those of skill in the art. Amplification procedures such as rolling circle amplification can also be advantageously employed, as exemplified herein.

First Segment: Targeting Segment

The first segment of a guide nucleic acid (e.g., guide RNA) includes a nucleotide sequence that is complementary to a sequence (a target site) in a target nucleic acid. In other words, the targeting segment of a guide nucleic acid (e.g., guide RNA) can interact with a target nucleic acid (e.g., an RNA, a DNA, a double-stranded DNA) in a sequence-specific manner via hybridization (i.e., base pairing). As such, the nucleotide sequence of the targeting segment may vary and can determine the location within the target nucleic acid that the guide nucleic acid (e.g., guide RNA) and the target nucleic acid will interact. The targeting segment of a guide nucleic acid (e.g., guide RNA) can be modified (e.g., by genetic engineering) to hybridize to any desired sequence (target site) within a target nucleic acid.

The targeting segment can have a length of from 12 nucleotides to 100 nucleotides. The nucleotide sequence (the targeting sequence, also referred to as a guide sequence) of the targeting segment that is complementary to a nucleotide sequence (target site) of the target nucleic acid can have a length of 12 nt or more. For example, the targeting sequence of the targeting segment that is complementary to a target site of the target nucleic acid can have a length of 12 nt or more, 15 nt or more, 17 nt or more, 18 nt or more, 19 nt or more, 20 nt or more, 25 nt or more, 30 nt or more, 35 nt or more or 40 nt.

The percent complementarity between the targeting sequence (i.e., guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some embodiments, the percent complementarity between the targeting sequence of the targeting segment and the target site of the target nucleic acid is 100% over the seven contiguous 5'-most nucleotides of the target site of the target nucleic acid. In some embodiments, the percent complementarity between the targeting sequence of the targeting segment and the target site of the target nucleic acid is 60% or more over 20 contiguous nucleotides. In some embodiments, the percent complementarity between the targeting sequence of the targeting segment and the target site of the target nucleic acid is 100% over the seventeen, eighteen, nineteen or twenty contiguous 5'-most nucleotides of the target site of the target nucleic acid and as low as 0% or more over the remainder. In such a case, the targeting sequence can be considered to be 17, 18, 19 or 20 nucleotides in length, respectively.

Second Segment: Protein-Binding Segment

The protein-binding segment of a guide nucleic acid (e.g., guide RNA) interacts with (binds) an RNA-guided endonuclease. The guide nucleic acid (e.g., guide RNA) guides the bound endonuclease to a specific nucleotide sequence within target nucleic acid (the target site) via the above mentioned targeting segment/targeting sequence/guide sequence. The protein-binding segment of a guide nucleic acid (e.g., guide RNA) comprises two stretches of nucleotides that are complementary to one another. The complementary nucleotides of the protein-binding segment hybridize to form a double stranded RNA duplex (dsRNA).

Single and Dual Guide Nucleic Acids

A dual guide nucleic acid (e.g., guide RNA) comprises two separate nucleic acid molecules. Each of the two molecules of a subject dual guide nucleic acid (e.g., guide RNA) comprises a stretch of nucleotides that are complementary to one another such that the complementary nucleotides of the two molecules hybridize to form the double stranded RNA duplex of the protein-binding segment.

In some embodiments, the duplex-forming segment of the activator is 60%, 65%, 70%, 75%, 80%, 85%, 90%, 95%, 98%, 99% or more identical or 100% identical to one of the activator (tracrRNA) molecules set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, the duplex-forming segment of the targeter is 60%, 65%, 70%, 75%, 80%, 85%, 90%, 95%, 98%, 99% or more identical or 100% identical to one of the targeter (crRNA) sequences set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

A dual guide nucleic acid (e.g., guide RNA) can be designed to allow for controlled (i.e., conditional) binding of a targeter with an activator. Because a dual guide nucleic acid (e.g., guide RNA) is not functional unless both the activator and the targeter are bound in a functional complex with Cas9, a dual guide nucleic acid (e.g., guide RNA) can be inducible (e.g., drug inducible) by rendering the binding between the activator and the targeter to be inducible. As one non-limiting example, RNA aptamers can be used to regulate (i.e., control) the binding of the activator with the targeter. Accordingly, the activator and/or the targeter can include an RNA aptamer sequence.

Aptamers (e.g., RNA aptamers) are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin), which specifically binds a particular drug (e.g., a small molecule). Binding of the drug causes a structural change in the folding of the RNA, which changes a feature of the nucleic acid of which the aptamer is a part. As non-limiting examples: (i) an activator with an aptamer may not be able to bind to the cognate targeter unless the aptamer is bound by the appropriate drug; (ii) a targeter with an aptamer may not be able to bind to the cognate activator unless the aptamer is bound by the appropriate drug; and (iii) a targeter and an activator, each comprising a different aptamer that binds a different drug, may not be able to bind to each other unless both drugs are present. As illustrated by these examples, a dual guide nucleic acid (e.g., guide RNA) can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley Interdiscip Rev RNA. 2012 May-June; 3(3):369-84; all of which are herein incorporated by reference in their entirety.

Non-limiting examples of nucleotide sequences that can be included in a dual guide nucleic acid (e.g., guide RNA) included in International Patent Application Nos. PCT/US2016/052690 and PCT/US2017/062617, or complements thereof that can hybridize to form a protein binding segment.

A subject single guide nucleic acid (e.g., guide RNA) comprises two stretches of nucleotides (much like a "targeter" and an "activator" of a dual guide nucleic acid) that are complementary to one another, hybridize to form the double stranded RNA duplex (dsRNA duplex) of the protein-binding segment (thus resulting in a stem-loop structure), and are covalently linked by intervening nucleotides ("linkers" or "linker nucleotides"). Thus, a subject single guide nucleic acid (e.g., a single guide RNA) can comprise a targeter and an activator, each having a duplex-forming segment, where the duplex-forming segments of the targeter and the activator hybridize with one another to form a dsRNA duplex. The targeter and the activator can be covalently linked via the 3' end of the targeter and the 5' end of the activator. Alternatively, targeter and the activator can be covalently linked via the 5' end of the targeter and the 3' end of the activator.

The linker of a single guide nucleic acid can have a length of from 3 nucleotides to 100 nucleotides. In some embodiments, the linker of a single guide nucleic acid (e.g., guide RNA) is 4 nt.

An exemplary single guide nucleic acid (e.g., guide RNA) comprises two complementary stretches of nucleotides that hybridize to form a dsRNA duplex. In some embodiments, one of the two complementary stretches of nucleotides of the single guide nucleic acid (e.g., guide RNA) (or the DNA encoding the stretch) is 60%, 65%, 70%, 75%, 80%, 85%, 90%, 95%, 98%, 99% or more identical or 100% identical to one of the activator (tracrRNA) molecules set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (e.g., guide RNA) (or the DNA encoding the stretch) is 60%, 65%, 70%, 75%, 80%, 85%, 90%, 95%, 98%, 99% or more identical or 100% identical to one of the targeter (crRNA) sequences set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (e.g., guide RNA) (or the DNA encoding the stretch) is 60%, 65%, 70%, 75%, 80%, 85%, 90%, 95%, 98%, 99% or more identical or 100% identical to one of the targeter (crRNA) sequences or activator (tracrRNA) sequences set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

Appropriate cognate pairs of targeters and activators can be routinely determined by taking into account the species name and base-pairing (for the dsRNA duplex of the protein-binding domain) Any activator/targeter pair can be used as part of dual guide nucleic acid (e.g., guide RNA) or as part of a single guide nucleic acid (e.g., guide RNA).

In some embodiments, an activator (e.g., a trRNA, trRNA-like molecule, etc.) of a dual guide nucleic acid (e.g., guide RNA) (e.g., a dual guide RNA) or a single guide nucleic acid (e.g., guide RNA) (e.g., a single guide RNA) includes a stretch of nucleotides with 60%, 65%, 70%, 75%, 80%, 85%, 90%, 95%, 98%, 99% or more, or 100% sequence identity with an activator (tracrRNA) molecule set forth in International Patent Application Nos. PCT/US2016/052690 and PCT/US2017/062617, or a complement thereof.

In some embodiments, an activator (e.g., a trRNA, trRNA-like molecule, etc.) of a dual guide nucleic acid (e.g., a dual guide RNA) or a single guide nucleic acid (e.g., a single guide RNA) includes 30 or more nucleotides (nt) (e.g., 40 or more, 50 or more, 60 or more, 70 or more, 75 or more nt). In some embodiments, an activator (e.g., a trRNA, trRNA-like molecule, etc.) of a dual guide nucleic acid (e.g., a dual guide RNA) or a single guide nucleic acid (e.g., a single guide RNA) has a length in a range of from 30 to 200 nucleotides (nt).

The protein-binding segment can have a length of from 10 nucleotides to 100 nucleotides.

Also with regard to both a subject single guide nucleic acid (e.g., single guide RNA) and to a subject dual guide nucleic acid (e.g., dual guide RNA), the dsRNA duplex of the protein-binding segment can have a length from 6 base pairs (bp) to 50 bp. The percent complementarity between the nucleotide sequences that hybridize to form the dsRNA duplex of the protein-binding segment can be 60% or more. For example, the percent complementarity between the nucleotide sequences that hybridize to form the dsRNA duplex of the protein-binding segment can be 65% or more, 70% or more, 75% or more, 80% or more, 85% or more, 90% or more, 95% or more, 98% or more, or 99% or more (e.g., in some embodiments, there are some nucleotides that do not hybridize and therefore create a bulge within the dsRNA duplex. In some embodiments, the percent complementarity between the nucleotide sequences that hybridize to form the dsRNA duplex of the protein-binding segment is 100%.

Hybrid Guide Nucleic Acids

In some embodiments, a guide nucleic acid is two RNA molecules (dual guide RNA). In some embodiments, a guide nucleic acid is one RNA molecule (single guide RNA). In some embodiments, a guide nucleic acid is a DNA/RNA hybrid molecule. In such embodiments, the protein-binding segment of the guide nucleic acid is RNA and forms an RNA duplex. Thus, the duplex-forming segments of the activator and the targeter is RNA. However, the targeting segment of a guide nucleic acid can be DNA. Thus, if a DNA/RNA hybrid guide nucleic acid is a dual guide nucleic acid, the "targeter" molecule and be a hybrid molecule (e.g., the targeting segment can be DNA and the duplex-forming segment can be RNA). In such embodiments, the duplex-forming segment of the "activator" molecule can be RNA (e.g., in order to form an RNA-duplex with the duplex-forming segment of the targeter molecule), while nucleotides of the "activator" molecule that are outside of the duplex-forming segment can be DNA (in which case the activator molecule is a hybrid DNA/RNA molecule) or can be RNA (in which case the activator molecule is RNA). If a DNA/RNA hybrid guide nucleic acid is a single guide nucleic acid, then the targeting segment can be DNA, the duplex-forming segments (which make up the protein-binding segment of the single guide nucleic acid) can be RNA, and nucleotides outside of the targeting and duplex-forming segments can be RNA or DNA.

A DNA/RNA hybrid guide nucleic can be useful in some embodiments, for example, when a target nucleic acid is an RNA. Cas9 normally associates with a guide RNA that hybridizes with a target DNA, thus forming a DNA-RNA duplex at the target site. Therefore, when the target nucleic acid is an RNA, it is sometimes advantageous to recapitulate a DNA-RNA duplex at the target site by using a targeting segment (of the guide nucleic acid) that is DNA instead of RNA. However, because the protein-binding segment of a guide nucleic acid is an RNA-duplex, the targeter molecule is DNA in the targeting segment and RNA in the duplex-forming segment. Hybrid guide nucleic acids can bias Cas9 binding to single stranded target nucleic acids relative to double stranded target nucleic acids.

Exemplary Guide Nucleic Acids

Any guide nucleic acid can be used. Many different types of guide nucleic acids are known in the art. The guide nucleic selected will be appropriately paired to the particular CRISPR system being used (e.g., the particular RNA guided endonuclease being used). Thus, the guide nucleic acid can be, for instance, a guide nucleic acid corresponding to any RNA guided endonuclease described herein or known in the art. Guide nucleic acids and RNA guided endonucleases are described, for example, in International Patent Application Nos. PCT/US2016/052690 and PCT/US2017/062617

In some embodiments, a suitable guide nucleic acid includes two separate RNA polynucleotide molecules. In some embodiments, the first of the two separate RNA polynucleotide molecules (the activator) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in International Patent Application Nos. PCT/US2016/052690 and PCT/US2017/062617, or a complement thereof. In some embodiments, the second of the two separate RNA polynucleotide molecules (the targeter) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in International Patent Application Nos. PCT/US2016/052690 and PCT/US2017/062617, or a complement thereof.

In some embodiments, a suitable guide nucleic acid is a single RNA polynucleotide and comprises first and second nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in International Patent Application Nos. PCT/US2016/052690 and PCT/US2017/062617, or complements thereof.

In some embodiments, the guide RNA is a Cpf1 and/or Cas9 guide RNA. A Cpf1 and/or Cas9 guide RNA can have a total length of from 30 nucleotides (nt) to 100 nt, e.g., from 30 nt to 40 nt, from 40 nt to 45 nt, from 45 nt to 50 nt, from 50 nt to 60 nt, from 60 nt to 70 nt, from 70 nt to 80 nt, from 80 nt to 90 nt, or from 90 nt to 100 nt. In some embodiments, a Cpf1 and/or Cas9 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt. A Cpf1 and/or Cas9 guide RNA can include a target nucleic acid-binding segment and a duplex-forming segment.

The target nucleic acid-binding segment of a Cpf1 and/or Cas9 guide RNA can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some embodiments, the target nucleic acid-binding segment has a length of 23 nt. In some embodiments, the target nucleic acid-binding segment has a length of 24 nt. In some embodiments, the target nucleic acid-binding segment has a length of 25 nt.

The target nucleic acid-binding segment of a Cpf1 and/or Cas9 guide RNA can have 100% complementarity with a corresponding length of target nucleic acid sequence. The targeting segment can have less than 100% complementarity with a corresponding length of target nucleic acid sequence. For example, the target nucleic acid binding segment of a Cpf1 and/or Cas9 guide RNA can have 1, 2, 3, 4, or 5 nucleotides that are not complementary to the target nucleic acid sequence. For example, in some embodiments, where a target nucleic acid-binding segment has a length of 25 nucleotides, and the target nucleic acid sequence has a length of 25 nucleotides, in some embodiments, the target nucleic acid-binding segment has 100% complementarity to the target nucleic acid sequence. As another example, in some embodiments, where a target nucleic acid-binding segment has a length of 25 nucleotides, and the target nucleic acid sequence has a length of 25 nucleotides, in some embodiments, the target nucleic acid-binding segment has 1 non-complementary nucleotide and 24 complementary nucleotides with the target nucleic acid sequence.

The duplex-forming segment of a Cpf1 and/or Cas9 guide RNA can have a length of from 15 nt to 25 nt, e.g., 15 nt, 16 nt, 17 nt, 18 nt, 19 nt, 20 nt, 21 nt, 22 nt, 23 nt, 24 nt, or 25 nt.

In some embodiments, the duplex-forming segment of a Cpf1 guide RNA can comprise the nucleotide sequence 5'-AAUUUCUACUGUUGUAGAU-3'.

Additional Elements

In some embodiments, a guide nucleic acid (e.g., guide RNA) includes an additional segment or segments (in some embodiments at the 5' end, in some embodiments the 3' end, in some embodiments at either the 5' or 3' end, in some embodiments embedded within the sequence (i.e., not at the 5' and/or 3' end), in some embodiments at both the 5' end and the 3' end, in some embodiments embedded and at the 5' end and/or the 3' end, etc.). For example, a suitable additional segment can include a 5' cap (e.g., a 7-methylguanylate cap ($m^7G$)); a 3' polyadenylated tail (i.e., a 3' poly(A) tail); a ribozyme sequence (e.g. to allow for self-cleavage of a guide nucleic acid or component of a guide nucleic acid, e.g., a targeter, an activator, etc.); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., a label such as a fluorescent molecule (i.e., fluorescent dye), a sequence or other moiety that facilitates fluorescent detection; a sequence or other modification that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptamers), labeled proteins, fluorescently labeled proteins, and the like); a modification or sequence that provides for increased, decreased, and/or controllable stability; and combinations thereof.

RNA-Guided Endonuclease

In addition to, or instead of, a guide nucleic acid, the composition can comprise an RNA-guided endonuclease protein or nucleic acid (e.g., mRNA or vector) encoding same. Any RNA-guided endonuclease can be used. The selection of the RNA guided endonuclease used will depend, at least in part, to the intended end-use of the CRISPR system employed.

In some embodiments, the polypeptide is a Cas 9 polypeptide. Suitable Cas9 polypeptides for inclusion in a composition of the present disclosure include a naturally-occurring Cas9 polypeptide (e.g., naturally occurs in bacterial and/or archaeal cells), or a non-naturally-occurring Cas9 polypeptide (e.g., the Cas9 polypeptide is a variant Cas9 polypeptide, a chimeric polypeptide as discussed below, and the like), as described below. In some embodiments, one skilled in the art can appreciate that the Cas9 polypeptide disclosed herein can be any variant derived or isolated from any source. In other embodiments, the Cas9 peptide of the present disclosure can include one or more of the mutations described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M. et al. Science. 2012 337:816-21; and Jinek M. et al. Science. 2014 Mar. 14; 343(6176); see also U.S. patent application Ser. No. 13/842,859, filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild type Cas9 protein having double-stranded nuclease activity, Cas9 mutants that act as single stranded nickases, or other mutants with modified nuclease activity. As such, a Cas9 polypeptide that is suitable for inclusion in a composition of the present disclosure can be an enzymatically active Cas9 polypeptide, e.g., can make single- or double-stranded breaks in a target nucleic acid, or alternatively can have reduced enzymatic activity compared to a wild-type Cas9 polypeptide.

Naturally occurring Cas9 polypeptides bind a guide nucleic acid, are thereby directed to a specific sequence within a target nucleic acid (a target site), and cleave the target nucleic acid (e.g., cleave dsDNA to generate a double strand break, cleave ssDNA, cleave ssRNA, etc.). A subject Cas9 polypeptide comprises two portions, an RNA-binding portion and an activity portion. The RNA-binding portion interacts with a subject guide nucleic acid, and an activity portion exhibits site-directed enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc. In some embodiments the activity portion exhibits reduced nuclease activity relative to the corresponding portion of a wild type Cas9 polypeptide. In some embodiments, the activity portion is enzymatically inactive.

Assays to determine whether a protein has an RNA-binding portion that interacts with a subject guide nucleic acid can be any convenient binding assay that tests for binding between a protein and a nucleic acid. Exemplary binding assays include binding assays (e.g., gel shift assays) that involve adding a guide nucleic acid and a Cas9 polypeptide to a target nucleic acid.

Assays to determine whether a protein has an activity portion (e.g., to determine if the polypeptide has nuclease activity that cleave a target nucleic acid) can be any convenient nucleic acid cleavage assay that tests for nucleic acid cleavage. Exemplary cleavage assays that include adding a guide nucleic acid and a Cas9 polypeptide to a target nucleic acid.

In some embodiments, a suitable Cas9 polypeptide for inclusion in a composition of the present disclosure has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other embodiments, a suitable Cas9 polypeptide for inclusion in a composition of the present disclosure has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologues from a wide variety of species have been identified and in some embodiments, the proteins share only a few identical amino acids. All identified Cas9 orthologues have the same domain architecture with a central HNH endonuclease domain and a split RuvC/RNaseH domain. Cas9 proteins share 4 key motifs with a conserved architecture. Motifs 1, 2, and 4 are RuvC like motifs while motif 3 is an HNH-motif.

Figure 1:
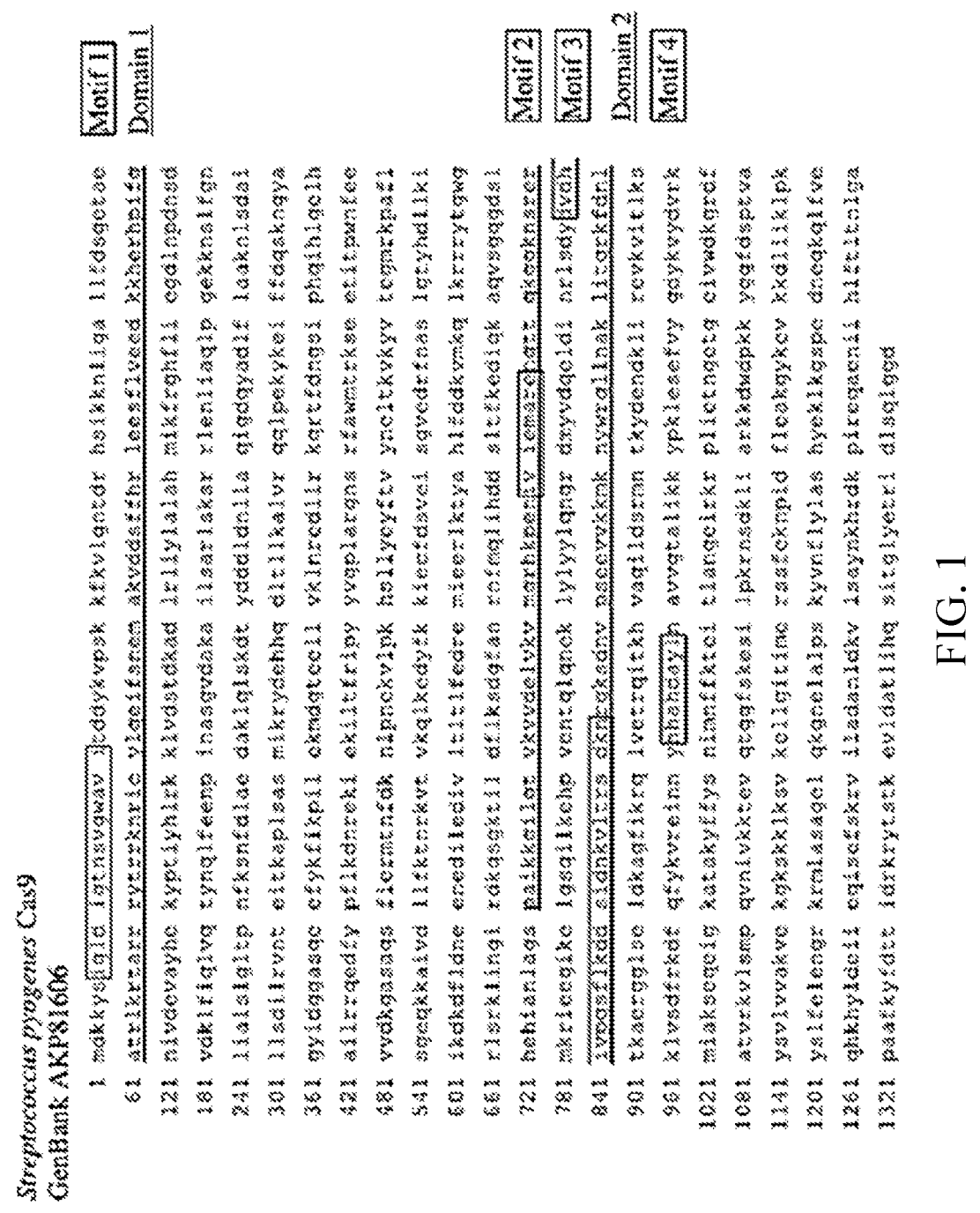

In some embodiments, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to the Cas9 amino acid sequence depicted in FIG. 1 (SEQ ID NO:1); or alternatively to motifs 1-4 of the Cas9 amino acid sequence depicted in Table 1 below (motifs 1-4 of SEQ ID NO:1 are SEQ ID NOs:3-6, respectively, as depicted in Table 1 below); or alternatively to amino acids 7-166 or 731-1003 of the Cas9 amino acid sequence depicted in FIG. 1 (SEQ ID NO:1)

In some embodiments, a Cas9 polypeptide comprises an amino acid sequence having 75% or more, 80% or more, 85% or more, 90% or more, 95% or more, or 98%, amino acid sequence identity to the amino acid sequence depicted in FIG. 1 and set forth in SEQ ID NO:1; and comprises amino acid substitutions of N497, R661, Q695, and Q926 relative to the amino acid sequence set forth in SEQ ID NO:1; or comprises an amino acid substitution of K855 relative to the amino acid sequence set forth in SEQ ID NO:1; or comprises amino acid substitutions of K810, K1003, and R1060 relative to the amino acid sequence set forth in SEQ ID NO:1; or comprises amino acid substitutions of K848, K1003, and R1060 relative to the amino acid sequence set forth in SEQ ID NO:1.

As used herein, the term "Cas9 polypeptide" encompasses the term "variant Cas9 polypeptide"; and the term "variant Cas9 polypeptide" encompasses the term "chimeric Cas9 polypeptide."

Variant Cas9 Polypeptides

A suitable Cas9 polypeptides for inclusion in a composition of the present disclosure includes a variant Cas9 polypeptide. A variant Cas9 polypeptide has an amino acid sequence that is different by one amino acid (e.g., has a deletion, insertion, substitution, fusion) (i.e., different by at least one amino acid) when compared to the amino acid sequence of a wild type Cas9 polypeptide (e.g., a naturally occurring Cas9 polypeptide, as described above). In some instances, the variant Cas9 polypeptide has an amino acid change (e.g., deletion, insertion, or substitution) that reduces the nuclease activity of the Cas9 polypeptide. For example, in some instances, the variant Cas9 polypeptide has less than 50%, less than 40%, less than 30%, less than 20%, less than 10%, less than 5%, or less than 1% of the nuclease activity of the corresponding wild-type Cas9 polypeptide. In some embodiments, the variant Cas9 polypeptide has no substantial nuclease activity. When a Cas9 polypeptide is a variant Cas9 polypeptide that has no substantial nuclease activity, it can be referred to as "dCas9."

In some embodiments, a variant Cas9 polypeptide has reduced nuclease activity. For example, a variant Cas9 polypeptide suitable for use in a binding method of the present disclosure exhibits less than about 20%, less than about 15%, less than about 10%, less than about 5%, less than about 1%, or less than about 0.1%, of the endonuclease activity of a wild-type Cas9 polypeptide, e.g., a wild-type Cas9 polypeptide comprising an amino acid sequence as depicted in FIG. 1 (SEQ ID NO:1).

In some embodiments, a variant Cas9 polypeptide can cleave the complementary strand of a target nucleic acid but has reduced ability to cleave the non-complementary strand of a double stranded target nucleic acid. For example, the variant Cas9 polypeptide can have a mutation (amino acid substitution) that reduces the function of the RuvC domain (e.g., "domain 1" of FIG. 1). As a non-limiting example, in some embodiments, a variant Cas9 polypeptide has a D10A mutation (e.g., aspartate to alanine at an amino acid position corresponding to position 10 of SEQ ID NO:1) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 polypeptide cleaves a double stranded target nucleic acid) (see, for example, Jinek et al., Science. 2012 Aug. 17; 337(6096):816-21).

In some embodiments, a variant Cas9 polypeptide can cleave the non-complementary strand of a double stranded target nucleic acid but has reduced ability to cleave the complementary strand of the target nucleic acid. For example, the variant Cas9 polypeptide can have a mutation (amino acid substitution) that reduces the function of the HNH domain (RuvC/HNH/RuvC domain motifs, "domain 2" of FIG. 1). As a non-limiting example, in some embodiments, the variant Cas9 polypeptide can have an H840A mutation (e.g., histidine to alanine at an amino acid position corresponding to position 840 of SEQ ID NO:1) (FIG. 1) and can therefore cleave the non-complementary strand of the target nucleic acid but has reduced ability to cleave the complementary strand of the target nucleic acid (thus resulting in a SSB instead of a DSB when the variant Cas9 polypeptide cleaves a double stranded target nucleic acid). Such a Cas9 polypeptide has a reduced ability to cleave a target nucleic acid (e.g., a single stranded target nucleic acid) but retains the ability to bind a target nucleic acid (e.g., a single-stranded or a double-stranded target nucleic acid).

In some embodiments, a variant Cas9 polypeptide has a reduced ability to cleave both the complementary and the non-complementary strands of a double stranded target nucleic acid. As a non-limiting example, in some embodiments, the variant Cas9 polypeptide harbors both the D10A and the H840A mutations (e.g., mutations in both the RuvC domain and the HNH domain) such that the polypeptide has a reduced ability to cleave both the complementary and the non-complementary strands of a double stranded target nucleic acid. Such a Cas9 polypeptide has a reduced ability to cleave a target nucleic acid (e.g., a single-stranded target nucleic acid or a double-stranded target nucleic acid) but retains the ability to bind a target nucleic acid (e.g., a single stranded target nucleic acid or a double-stranded target nucleic acid).

As another non-limiting example, in some embodiments, the variant Cas9 polypeptide harbors W476A and W1126A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors H840A, W476A, and W1126A, mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors H840A, D10A, W476A, and W1126A, mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors, H840A, P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors D10A, H840A, P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

Other residues can be mutated to achieve the above effects (i.e. inactivate one or the other nuclease portions). As non-limiting examples, residues D10, G12, G17, E762, H840, N854, N863, H982, H983, A984, D986, and/or A987 can be altered (i.e., substituted) (see Table 1 for more information regarding the conservation of Cas9 amino acid residues). Also, mutations other than alanine substitutions are suitable.

In some embodiments, a variant Cas9 polypeptide that has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A1, A984A, and/or D986A), the variant Cas9 polypeptide can still bind to target nucleic acid in a site-specific manner (because it is still guided to a target nucleic acid sequence by a guide nucleic acid) as long as it retains the ability to interact with the guide nucleic acid.

TABLE 1

Table 1 lists 4 motifs that are present in Cas9 sequences from various species The amino acids listed here are from the Cas9 from *S. pyogenes* (SEQ ID NO: 1).

| Motif | Motif | Amino acids (residue #s) | Highly conserved |
|---|---|---|---|
| 1 | RuvC | IGLDIGTNSVGWAVI (7-21) (SEQ ID NO: 3) | D10, G12, G17 |
| 2 | RuvC | IVIEMARE (759-766) (SEQ ID NO: 4) | E762 |
| 3 | HNH-motif | DVDHIVPQSFLKDDSIDNKVLTRSDKN (837-863) (SEQ ID NO: 5) | H840, N854, N863 |
| 4 | RuvC | HHAHDAYL (982-989) (SEQ ID NO: 6) | H982, H983, A984, D986, A987 |

In addition to the above, a variant Cas9 protein can have the same parameters for sequence identity as described above for Cas9 polypeptides. Thus, in some embodiments, a suitable variant Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity of the Cas9 amino acid sequence depicted in FIG. 1 (SEQ ID NO:1), or alternatively to motifs 1-4 (motifs 1-4 of SEQ ID NO:1 are SEQ ID NOs:3-6, respectively, as depicted in Table 1); or alternatively to amino acids 7-166 or 731-1003 of the Cas9 amino acid sequence depicted in FIG. 1 (SEQ ID NO:1. Any Cas9 protein as defined above can be used as a Cas9 polypeptide, or as part of a chimeric Cas9 polypeptide, in a composition of the present disclosure, including those specifically referenced in International Patent Application Nos. PCT/US2016/052690 and PCT/US2017/062617.

In some embodiments, a suitable variant Cas9 polypeptide comprises an amino acid sequence having 60% or more, 70% or more, 75% or more, 80% or more, 85% or more, 90% or more, 95% or more, 99% or more, or 100% amino acid sequence identity to the Cas9 amino acid sequence depicted in FIG. 1 (SEQ ID NO:1). Any Cas9 protein as defined above can be used as a variant Cas9 polypeptide or as part of a chimeric variant Cas9 polypeptide in a composition of the present disclosure, including those specifically referenced in International Patent Application Nos. PCT/US2016/052690 and PCT/US2017/062617.

Chimeric Polypeptides (Fusion Polypeptides)

In some embodiments, a variant Cas9 polypeptide is a chimeric Cas9 polypeptide (also referred to herein as a fusion polypeptide, e.g., a "Cas9 fusion polypeptide"). A Cas9 fusion polypeptide can bind and/or modify a target nucleic acid (e.g., cleave, methylate, demethylate, etc.) and/or a polypeptide associated with target nucleic acid (e.g., methylation, acetylation, etc., of, for example, a histone tail).

A Cas9 fusion polypeptide is a variant Cas9 polypeptide by virtue of differing in sequence from a wild type Cas9 polypeptide (e.g., a naturally occurring Cas9 polypeptide). A Cas9 fusion polypeptide is a Cas9 polypeptide (e.g., a wild type Cas9 polypeptide, a variant Cas9 polypeptide, a variant Cas9 polypeptide with reduced nuclease activity (as described above), and the like) fused to a covalently linked heterologous polypeptide (also referred to as a "fusion partner"). In some embodiments, a Cas9 fusion polypeptide is a variant Cas9 polypeptide with reduced nuclease activity (e.g., dCas9) fused to a covalently linked heterologous polypeptide. In some embodiments, the heterologous polypeptide exhibits (and therefore provides for) an activity (e.g., an enzymatic activity) that will also be exhibited by the Cas9 fusion polypeptide (e.g., methyltransferase activity, acetyltransferase activity, kinase activity, ubiquitinating activity, etc.). In some such embodiments, a method of binding, e.g., where the Cas9 polypeptide is a variant Cas9 polypeptide having a fusion partner (i.e., having a heterologous polypeptide) with an activity (e.g., an enzymatic activity) that modifies the target nucleic acid, the method can also be considered to be a method of modifying the target nucleic acid. In some embodiments, a method of binding a target nucleic acid (e.g., a single stranded target nucleic acid) can result in modification of the target nucleic acid. Thus, in some embodiments, a method of binding a target nucleic acid (e.g., a single stranded target nucleic acid) can be a method of modifying the target nucleic acid.

In some embodiments, the heterologous sequence provides for subcellular localization, i.e., the heterologous sequence is a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an endoplasmic reticulum (ER) retention signal, and the like). In some embodiments, a variant Cas9 does not include a NLS so that the protein is not targeted to the nucleus (which can be advantageous, e.g., when the target nucleic acid is an RNA that is present in the cytosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some embodiments is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

A subject Cas9 fusion polypeptide (Cas9 fusion protein) can have multiple (1 or more, 2 or more, 3 or more, etc.) fusion partners in any combination of the above. As an illustrative example, a Cas9 fusion protein can have a heterologous sequence that provides an activity (e.g., for transcription modulation, target modification, modification of a protein associated with a target nucleic acid, etc.) and can also have a subcellular localization sequence. In some embodiments, such a Cas9 fusion protein might also have a tag for ease of tracking and/or purification (e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). As another illustrative example, a Cas9 protein can have one or more NLSs (e.g., two or more, three or more, four or more, five or more, 1, 2, 3, 4, or 5 NLSs). In some embodiments a fusion partner (or multiple fusion partners) (e.g., an NLS, a tag, a fusion partner providing an activity, etc.) is located at or near the C-terminus of Cas9. In some embodiments a fusion partner (or multiple fusion partners) (e.g., an NLS, a tag, a fusion partner providing an activity, etc.) is located at the N-terminus of Cas9. In some embodiments a Cas9 has a fusion partner (or multiple fusion partners)(e.g., an NLS, a tag, a fusion partner providing an activity, etc.) at both the N-terminus and C-terminus.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some embodiments, a suitable degron is constitutive such that the degron exerts its influence on protein stability independent of experimental control (i.e., the degron is not drug inducible, temperature inducible, etc.) In some embodiments, the degron provides the variant Cas9 polypeptide with controllable stability such that the variant Cas9 polypeptide can be turned "on" (i.e., stable) or "off" (i.e., unstable, degraded) depending on the desired conditions. For example, if the degron is a temperature sensitive degron, the variant Cas9 polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1): Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals. Thus, fusing Cas9 (e.g., wild type Cas9; variant Cas9; variant Cas9 with reduced nuclease activity, e.g., dCas9; and the like) to a degron sequence produces a "tunable" and "inducible" Cas9 polypeptide. Any of the fusion partners described herein can be used in any desirable combination. As one non-limiting example to illustrate this point, a Cas9 fusion protein (i.e., a chimeric Cas9 polypeptide) can comprise a YFP sequence for detection, a degron sequence for stability, and transcription activator sequence to increase transcription of the target nucleic acid. A suitable reporter protein for use as a fusion partner for a Cas9 polypeptide (e.g., wild type Cas9, variant Cas9, variant Cas9 with reduced nuclease function, etc.), includes, but is not limited to, the following exemplary proteins (or functional fragment thereof): his3, β-galactosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a Cas9 fusion protein is unlimited. In some embodiments, a Cas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Examples of various additional suitable fusion partners (or fragments thereof) for a subject variant Cas9 polypeptide include, but are not limited to those described in the PCT patent applications: WO2010/075303, WO2012/068627, and WO2013/155555 which are hereby incorporated by reference in their entirety.

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription include transcription activator and transcription repressor domains (e.g., the Krüppel associated box (KRAB or SKD); the Mad mSIN3 interaction domain (SID); the ERF repressor domain (ERD), etc.). In some such embodiments, a Cas9 fusion protein is targeted by the guide nucleic acid to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some embodiments, the changes are transient (e.g., transcription repression or activation). In some embodiments, the changes are inheritable (e.g., when epigenetic modifications are made to the target nucleic acid or to proteins associated with the target nucleic acid, e.g., nucleosomal histones).

Non-limiting examples of fusion partners for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); heliembodiments; RNA-binding proteins; and the like. It is understood that a fusion partner can include the entire protein or in some embodiments can include a fragment of the protein (e.g., a functional domain).

In some embodiments, the heterologous sequence can be fused to the C-terminus of the Cas9 polypeptide. In some embodiments, the heterologous sequence can be fused to the N-terminus of the Cas9 polypeptide. In some embodiments, the heterologous sequence can be fused to an internal portion (i.e., a portion other than the N- or C-terminus) of the Cas9 polypeptide.

In addition the fusion partner of a chimeric Cas9 polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase I, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAPI, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable fusion partner is a PUF RNA-binding domain, which is described in more detail in WO2012068627.

Some RNA splicing factors that can be used (in whole or as fragments thereof) as fusion partners for a Cas9 polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cis-elements that are located in either the core exon region or the exon extension region (i.e., between the two alternative 5' splice sites). For more examples, see W2010075303.

In some embodiments, a Cas9 polypeptide (e.g., a wild type Cas9, a variant Cas9, a variant Cas9 with reduced nuclease activity, etc.) can be linked to a fusion partner via a peptide spacer.

In some embodiments, a Cas9 polypeptide comprises a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD attached to another molecule facilitates entry of the molecule into the nucleus (e.g., in some embodiments, a PTD includes a nuclear localization signal (NLS)). In some embodiments, a Cas9 polypeptide comprises two or more NLSs, e.g., two or more NLSs in tandem. In some embodiments, a PTD is covalently linked to the amino terminus of a Cas9 polypeptide. In some embodiments, a PTD is covalently linked to the carboxyl terminus of a Cas9 polypeptide. In some embodiments, a PTD is covalently linked to the amino terminus and to the carboxyl terminus of a Cas9 polypeptide. In some embodiments, a PTD is covalently linked to a nucleic acid (e.g., a guide nucleic acid, a polynucleotide encoding a guide nucleic acid, a polynucleotide encoding a Cas9 polypeptide, etc.). Exemplary PTDs include but are not limited to a minimal undecapeptide protein transduction domain (corresponding to residues 47-57 of HIV-1 TAT comprising YGRKKRRQRRR; SEQ ID NO:7); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Nat. Acad. Sci. USA* 97:13003-13008); RRQRRTSKLMKR (SEQ ID NO:8); Transportan GWTLNSAGYLLGKINLKALAALAKKIL (SEQ ID NO:9); KALAWEAKLAKALAKALAKHLAKA-LAKALKCEA (SEQ ID NO:10); and RQIKIWFQNRRMKWKK (SEQ ID NO:11). Exemplary PTDs include but are not limited to, YGRKKRRQRRR (SEQ ID NO:12), RKKRRQRRR (SEQ ID NO:13); an arginine homopolymer of from 3 arginine residues to 50 arginine residues; Exemplary PTD domain amino acid sequences include, but are not limited to, any of the following: YGRKKRRQRRR (SEQ ID NO:14); RKKRRQRR (SEQ ID NO:15); YARAAARQARA (SEQ ID NO:16); THRLPRRRRRR (SEQ ID NO:17); and GGRRARRRRRR (SEQ ID NO:18). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R$^9$") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some embodiments, the composition can comprise a Cpf1 RNA-guided endonuclease, an example of which is provided in FIG. 2, 16, or 17. Another name for the Cpf1 RNA-guided endonuclease is Cas12a. The Cpf1 CRISPR systems of the present disclosure comprise i) a single endonuclease protein, and ii) a crRNA, wherein a portion of the 3' end of crRNA contains the guide sequence complementary to a target nucleic acid. In this system, the Cpf1 nuclease is directly recruited to the target DNA by the crRNA. In some embodiments, guide sequences for Cpf1 must be at least 12nt, 13nt, 14nt, 15nt, or 16nt in order to achieve detectable DNA cleavage, and a minimum of 14nt, 15nt, 16nt, 17nt, or 18nt to achieve efficient DNA cleavage.

The Cpf1 systems of the present disclosure differ from Cas9 in a variety of ways. First, unlike Cas9, Cpf1 does not require a separate tracrRNA for cleavage. In some embodiments, Cpf1 crRNAs can be as short as about 42-44 bases long—of which 23-25 nt is guide sequence and 19 nt is the constitutive direct repeat sequence. In contrast, the combined Cas9 tracrRNA and crRNA synthetic sequences can be about 100 bases long.

Second, Cpf1 prefers a "TTN" PAM motif that is located 5' upstream of its target. This is in contrast to the "NGG" PAM motifs located on the 3' of the target DNA for Cas9 systems. In some embodiments, the uracil base immediately preceding the guide sequence cannot be substituted (Zetsche, B. et al. 2015. "Cpf1 Is a Single RNA-Guided Endonuclease of a Class 2 CRISPR-Cas System" Cell 163, 759-771, which is hereby incorporated by reference in its entirety for all purposes).

Third, the cut sites for Cpf1 are staggered by about 3-5 bases, which create "sticky ends" (Kim et al., 2016. "Genome-wide analysis reveals specificities of Cpf1 endonucleases in human cells" published online Jun. 6, 2016). These sticky ends with 3-5 bp overhangs are thought to facilitate NHEJ-mediated-ligation, and improve gene editing of DNA fragments with matching ends. The cut sites are in the 3' end of the target DNA, distal to the 5' end where the PAM is. The cut positions usually follow the 18th base on the non-hybridized strand and the corresponding 23rd base on the complementary strand hybridized to the crRNA.

Fourth, in Cpf1 complexes, the "seed" region is located within the first 5 nt of the guide sequence. Cpf1 crRNA seed regions are highly sensitive to mutations, and even single base substitutions in this region can drastically reduce cleavage activity (see Zetsche B. et al. 2015 "Cpf1 Is a Single RNA-Guided Endonuclease of a Class 2 CRISPR-Cas System" Cell 163, 759-771). Critically, unlike the Cas9 CRISPR target, the cleavage sites and the seed region of Cpf1 systems do not overlap. Additional guidance on designing Cpf1 crRNA targeting oligos is available on (Zetsche B. et al. 2015. "Cpf1 Is a Single RNA-Guided Endonuclease of a Class 2 CRISPR-Cas System" Cell 163, 759-771).

Persons skilled in the art will appreciate that the Cpf1 disclosed herein can be any variant derived or isolated from any source, many of which are known in the art. For example, in some embodiments, the Cpf1 peptide of the present disclosure can include FnCPF1 (e.g., SEQ ID NO: 2) set forth in FIG. 2, AsCpf1 (e.g., FIG. 16), LbCpf1 (e.g., FIG. 17) or any other of the many known Cpf1 proteins from various other microorganism species, and synthetic variants thereof.

In some embodiments, the composition comprises a Cpf1 polypeptide. In some embodiments, the Cpf1 polypeptide is enzymatically active, e.g., the Cpf1 polypeptide, when bound to a guide RNA, cleaves a target nucleic acid. In some embodiments, the Cpf1 polypeptide exhibits reduced enzymatic activity relative to a wild-type Cpf1 polypeptide (e.g., relative to a Cpf1 polypeptide comprising the amino acid sequence depicted in FIG. 2, 16, or 17), and retains DNA binding activity.

In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 16, or 17. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the amino acid sequence depicted in FIG. 2, 16, or 17.

In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of a Cpf1 polypeptide of the amino acid sequence depicted in FIG. 2, 16, or 17. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of a Cpf1 polypeptide of the amino acid sequence depicted in FIG. 2, 16, or 17. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of a Cpf1 polypeptide of the amino acid sequence depicted in FIG. 2, 16, or 17.

In some embodiments, the Cpf1 polypeptide exhibits reduced enzymatic activity relative to a wild-type Cpf1 polypeptide (e.g., relative to a Cpf1 polypeptide comprising the amino acid sequence depicted in FIG. 2, 16, or 17), and retains DNA binding activity. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 16, or 17; and comprises an amino acid substitution (e.g., a D-A substitution) at an amino acid residue corresponding to amino acid 917 of the amino acid sequence depicted in FIG. 2, 16, or 17. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 16, or 17; and comprises an amino acid substitution (e.g., an E→A substitution) at an amino acid residue corresponding to amino acid 1006 of the amino acid sequence depicted in FIG. 2, 16, or 17. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 16, or 17; and comprises an amino acid substitution (e.g., a D→A substitution) at an amino acid residue corresponding to amino acid 1255 of the amino acid sequence depicted in FIG. 2, 16, or 17.

In some embodiments, the Cpf1 polypeptide is a fusion polypeptide, e.g., where a Cpf1 fusion polypeptide comprises: a) a Cpf1 polypeptide; and b) a heterologous fusion partner. In some embodiments, the heterologous fusion partner is fused to the N-terminus of the Cpf1 polypeptide. In some embodiments, the heterologous fusion partner is fused to the C-terminus of the Cpf1 polypeptide. In some embodiments, the heterologous fusion partner is fused to both the N-terminus and the C-terminus of the Cpf1 polypeptide. In some embodiments, the heterologous fusion partner is inserted internally within the Cpf1 polypeptide.

Suitable heterologous fusion partners include NLS, epitope tags, fluorescent polypeptides, and the like.

Linked Guide RNA and Donor Nucleic Acid

In one aspect, the invention provides a complex comprising a CRISPR system comprising an RNA-guided endonuclease (e.g. a Cas9 or Cpf1 polypeptide), a guide RNA and a donor polynucleotide, wherein the guide RNA and the donor polynucleotide are linked. As exemplified herein, the guide RNA and donor polynucleotide can be either covalently or non-covalently linked. In one embodiment, the guide RNA and donor polynucleotide are chemically ligated. In another embodiment, the guide RNA and donor polynucleotide are enzymatically ligated. In one embodiment, the guide RNA and donor polynucleotide hybridize to each other. In another embodiment, the guide RNA and donor polynucleotide both hybridize to a bridge sequence. Any number of such hybridization schemes are possible.

Deaminase

In some embodiments, the complex or composition further comprises a deaminase (e.g., an adenine base editor). As used herein, the term "deaminase" or "deaminase domain" refers to an enzyme that catalyzes the removal of an amine group from a molecule, or deamination. In some embodiments, the deaminase is a cytidine deaminase, catalyzing the hydrolytic deamination of cytidine or deoxycytidine to uridine or deoxyuridine, respectively. In some embodiments, the deaminase is a cytosine deaminase, catalyzing the hydrolytic deamination of cytosine to uracil (e.g., in RNA) or thymine (e.g., in DNA).

In some embodiments, the deaminase is an adenosine deaminase, which catalyzes the hydrolytic deamination of adenine or adenosine. In some embodiments, the deaminase or deaminase domain is an adenosine deaminase, catalyzing the hydrolytic deamination of adenosine or deoxyadenosine to inosine or deoxyinosine, respectively. In some embodiments, the adenosine deaminase catalyzes the hydrolytic deamination of adenine or adenosine in deoxyribonucleic acid (DNA) The adenosine deaminases (e.g. engineered adenosine deaminases, evolved adenosine deaminases) provided herein may be from any organism, such as a bacterium. In some embodiments, the deaminase or deaminase domain is a variant of a naturally-occurring deaminase from an organism, such as a human, chimpanzee, gorilla, monkey, cow, dog, rat, or mouse.

In some embodiments, the deaminase or deaminase domain does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99% or at least 99.5% identical to a naturally-occurring deaminase. In some embodiments, the adenosine deaminase is from a bacterium, such as, *E. coli, S. aureus, S. typhi, S. putrefaciens, H. influenzae*, or *C. crescentus*. In some embodiments, the adenosine deaminase is a TadA deaminase. In some embodiments, the TadA deaminase is an *E. coli* TadA deaminase (ecTadA). In some embodiments, the TadA deaminase is a truncated *E. coli* TadA deaminase. For example, the truncated ecTadA may be missing one or more N-terminal amino acids relative to a full-length ecTadA. In some embodiments, the truncated ecTadA may be missing 1, 2, 3, 4, 5, 6, 7, 8, 9, 10, 11, 12, 13, 14, 15, 6, 17, 18, 19, or 20 N-terminal amino acid residues relative to the full length ecTadA. In some embodiments, the truncated ecTadA may be missing 1, 2, 3, 4, 5, 6, 7, 8, 9, 10, 11, 12, 13, 14, 15, 6, 17, 18, 19, or 20 C-terminal amino acid residues relative to the full length ecTadA. In some embodiments, the ecTadA deaminase does not comprise an N-terminal methionine. In some embodiments, the deaminase is APOBEC1 or a variant thereof.

The deaminase can be used in conjugation with any of the other CRISPR elements described herein (i.e., as a composition), or the deaminase can be fused to any of the other CRISPR elements (e.g., Cas9 or Cpf1) described herein (i.e., as a complex). In certain embodiments, the deaminase is fused to Cas9, Cpf1, or a variant thereof.

Other Components

The composition can further comprise any other components typically used in nucleic acid or protein delivery formulations. For instance, the composition can further comprise lipids, lipoproteins (e.g., cholesterol and derivatives), phospholipids, polymers or other components of liposomal or micellar delivery vehicles. The composition also can comprise solvent or carrier suitable for administration to cells or hosts, such as a mammal or human.

In some embodiments, the composition comprises a second polymer that comprises polyethylene oxide (PEG). For example, the composition can comprise PEG-pAsp(DET), PEG-pAsp, derivatives of PEG-pAsp(DET), derivatives of PEG-pAsp, or a combination thereof. Without wishing to be bound by any particular theory, it is believed that these PEGylated polymers can control the size of nanoparticles and their interaction with serum proteins and target cells. The polyethylene oxide polymer can be combined with the other components in any manner and any order.

In some embodiments, the composition further comprises one or more surfactants. The surfactant can be a non-ionic surfactant and/or a zwitterionic surfactant. A list of exemplary surfactants includes, but is not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradenane, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG-EPAL CA-6301NP-40); phospholipids such as phosphatidylcholine (lecithin) polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether, and sorbitan esters (commonly known as the Spans), such as sorbitan trioleate (Span 85) and sorbitan monolaurate. In some embodiments, the surfactant is an anticoagulant (e.g., heparin or the like). In some embodiments, the composition further comprises one or more pharmaceutically acceptable carriers and/or excipients.

In some instances, a component (e.g., a nucleic acid component (e.g., a guide nucleic acid, etc.); a protein component (e.g., a Cas9 or Cpf1 polypeptide, a variant Cas9 or Cpf1 polypeptide); and the like) includes a label moiety.

The terms "label", "detectable label", or "label moiety" as used herein refer to any moiety that provides for signal detection and may vary widely depending on the particular nature of the assay. Label moieties of interest include both directly detectable labels (direct labels)(e.g., a fluorescent label) and indirectly detectable labels (indirect labels)(e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some embodiments, when two or more components are labeled, they can be labeled with label moieties that are distinguishable from one another.

Encapsulation and Nanoparticles

In some embodiments of the composition, the polymer combines with the nucleic acid and/or polypeptide and partially or completely encapsulates the nucleic acid and/or polypeptide. The composition can, in some formulations, provide a nanoparticle comprising the polymer and nucleic acid and/or polypeptide.

In some embodiments, the composition can comprise a core nanoparticle in addition to the polymer described herein and the nucleic acid or polypeptide. Any suitable nanoparticle can be used, including metal (e.g., gold) nanoparticles or polymer nanoparticles.

The polymer described herein and the nucleic acid (e.g., guide RNA, donor polynucleotide, or both) or polypeptide can be conjugated directly or indirectly to a nanoparticle surface. For example, the polymer described herein and the nucleic acid (e.g., guide RNA, donor polynucleotide, or both) or polypeptide can be conjugated directly to the surface of a nanoparticle or indirectly through an intervening linker.

Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide functionalities. In embodiments where the nanoparticle includes gold, a linker can be any thiol-containing molecule. Reaction of a thiol group with the gold results in a covalent sulfide (—S—) bond. Linker design and synthesis are well known in the art.

In some embodiments, the nucleic acid conjugated to the nanoparticle is a linker nucleic acid that serves to non-covalently bind one or more elements described herein (e.g., a Cas9 polypeptide, and a guide RNA, a donor polynucleotide, and a Cpf1 polypeptide) to the nanoparticle-nucleic acid conjugate. For instance, the linker nucleic acid can have a sequence that hybridizes to the guide RNA or donor polynucleotide.

The nucleic acid conjugated to the nanoparticle (e.g., a colloidal metal (e.g., gold) nanoparticle; a nanoparticle comprising a biocompatible polymer) can have any suitable length. When the nucleic acid is a guide RNA or donor polynucleotide, the length will be as suitable for such molecules, as discussed herein and known in the art. If the nucleic acid is a linker nucleic acid, it can have any suitable length for a linker, for instance, a length of from 10 nucleotides (nt) to 1000 nt, e.g., from about 1 nt to about 25 nt, from about 25 nt to about 50 nt, from about 50 nt to about 100 nt, from about 100 nt to about 250 nt, from about 250 nt to about 500 nt, or from about 500 nt to about 1000 nt. In some instances, the nucleic acid conjugated to the nanoparticle (e.g., a colloidal metal (e.g., gold) nanoparticle; a nanoparticle comprising a biocompatible polymer) nanoparticle can have a length of greater than 1000 nt.

When the nucleic acid linked (e.g., covalently linked; non-covalently linked) to a nanoparticle comprises a nucleotide sequence that hybridizes to at least a portion of the guide RNA or donor polynucleotide present in a complex of the present disclosure, it has a region with sequence identity to a region of the complement of the guide RNA or donor polynucleotide sequence sufficient to facilitate hybridization. In some embodiments, a nucleic acid linked to a nanoparticle in a complex of the present disclosure has at least 50%, at least 60%, at least 70%, at least 80%, at least 90%, at least 95%, at least 98%, at least 99%, or 100%, nucleotide sequence identity to a complement of from 10 to 50 nucleotides (e.g., from 10 nucleotides (nt) to 15 nt, from 15 nt to 20 nt, from 20 nt to 25 nt, from 25 nt to 30 nt, from 30 nt to 40 nt, or from 40 nt to 50 nt) of a guide RNA or donor polynucleotide present in the complex.

In some embodiments, a nucleic acid linked (e.g., covalently linked; non-covalently linked) to a nanoparticle is a donor polynucleotide, or has the same or substantially the same nucleotide sequence as a donor polynucleotide. In some embodiments, a nucleic acid linked (e.g., covalently linked; non-covalently linked) to a nanoparticle comprises a nucleotide sequence that is complementary to a donor DNA template.

Method of Use

The polymers provided herein can be used for any purpose, but are believed to be particularly useful for combining with and, in some embodiments, encapsulating biological molecules (e.g., nucleic acids and polypeptides) for various purposes. In one aspect, there is provided a method of encapsulating a biological molecule, such as a polypeptide or nucleic acid, by combining a polymer of the invention as described herein with the biological molecule, whereby the polymer partially or completely encapsulates the biomolecule. The biomolecule partially or completely encapsulated by the polymer is sometime referred to a as a nanoparticle.

Also provided herein is a method of delivering a nucleic acid and/or polypeptide to a cell, wherein the cell can be in vitro or in vivo. The method comprises administering a composition comprising the polymer and nucleic acid and/or polypeptide, as described herein, to the cell or to a subject containing the cell. The method can be used with respect to any type of cell or subject, but is particularly useful for mammalian cells (e.g., human cells). In some embodiments, the polymer comprises a targeting agent, such that nucleic acid and/or polypeptide is delivered predominantly or exclusively to target cells or tissues (e.g., cells or tissues of the peripheral nervous system, the central nervous system, the eye of the subject, liver, muscle, lung, bone (e.g., hematopoietic cells), or tumor cells or tissues).

When used with a composition comprising one or more components of a CRISPR system, the method may be employed to induce edit a target nucleic acid or gene. In some embodiments, a method of modifying a target nucleic acid comprises homology-directed repair (HDR). In some embodiments, use of a complex of the present disclosure to carry out HDR provides an efficiency of HDR of at least 1%, at least 2%, at least 3%, at least 4%, at least 5%, at least 10%, at least 15%, at least 20%, at least 25%, or more than 25%. In some embodiments, a method of modifying a target nucleic acid comprises non-homologous end joining (NHEJ). In some embodiments, use of a complex of the present disclosure to carry out HDR provides an efficiency of NHEJ of at least 1%, at least 2%, at least 3%, at least 4%, at least 5%, at least 10%, at least 15%, at least 20%, at least 25%, or more than 25%.

The following examples further illustrate the invention but, of course, should not be construed as in any way limiting its scope.

Example 1

This example provides guidance for the synthesis of a polymer described herein. The synthesis includes a Michael Addition with an acrylate. An exemplary procedure is as follows.

Scheme 1.

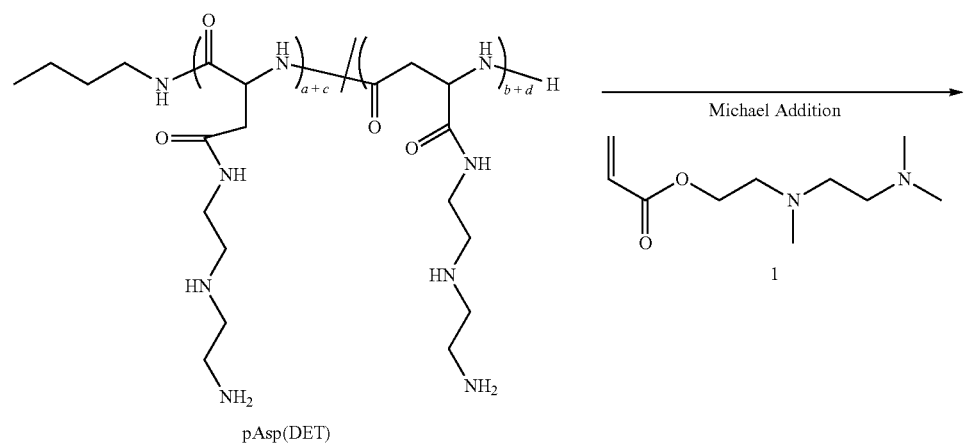

-continued

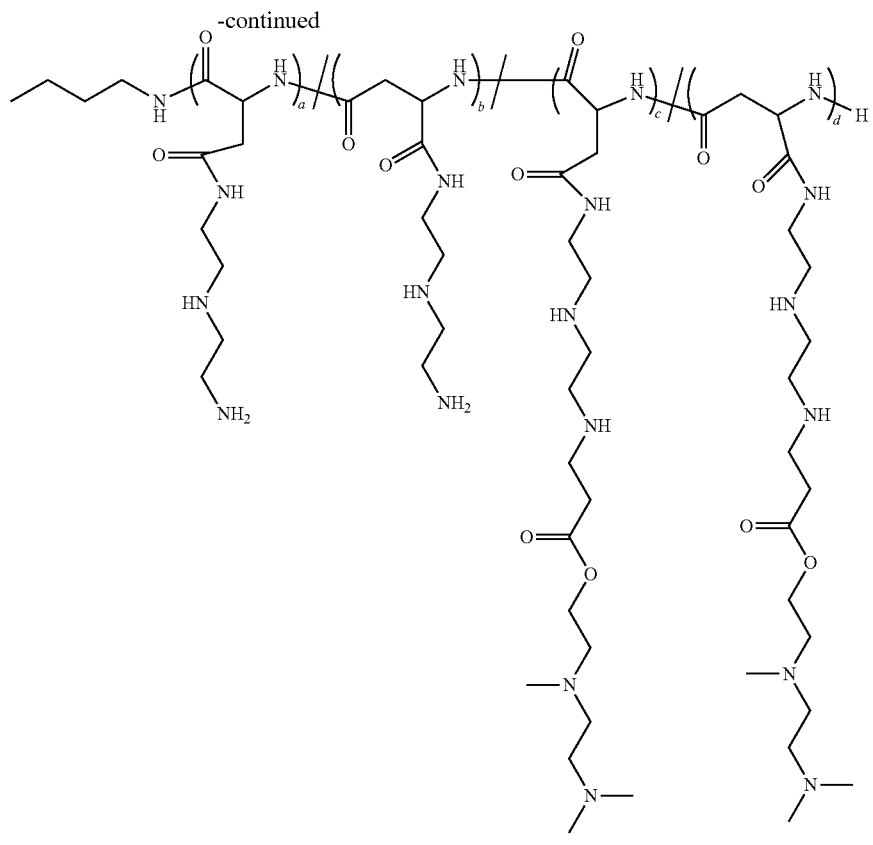

Polymer 5

In a glass vial, pAsp(DET) (5 mg, 0.22 μmol) was suspended in dimethyl sulfoxide ("DMSO"; 700 μL). To the suspension was added 30 μL of trimethylamine ("TEA") and the resulting suspension was stirred until all polymers completely dissolved. To the reaction mixture was added acrylate 1 (1.15 mg, 5.5 μmol) and the reaction mixture was stirred for 40 hours at room temperature. The crude product was purified by precipitation into acetonitrile and washed with acetonitrile three times to yield 4 mg of Polymer 5, wherein (a+b) is 55 and (c+d) is 25. $^1$H NMR (400 MHz, D$_2$O): δ 4.8-4.6 (bs, 4H), 4.2 (t, 2H), 3.4-2.4 (m, 40H).

As demonstrated by Scheme 1, Michael Addition with acrylate 1 results in an amine-based bond (see, for example, Polymer 5). Thus, the original amine-functionality in pAsp (DET) remains intact.

A similar procedure can be used to prepare additional polymers of Formula 1 (e.g., Polymers 1-4 and 6-12). Nucleophilic substitution can be used to provide polymers 28 and 29.

Furthermore, the procedure can be applied to a different starting polymer, such as a polymer prepared as shown in Example 7, to provide other polymers of Formula 1 (e.g., starting with polymer 30 or 32, demethylated at the terminal nitrogen to provide a primary or secondary amine, the method can provide Polymers 13-24).

Example 2

This example provides guidance for the synthesis of a polymer described herein. The synthesis includes a Michael Addition with an acrylate. An exemplary procedure is as follows.

Scheme 1.

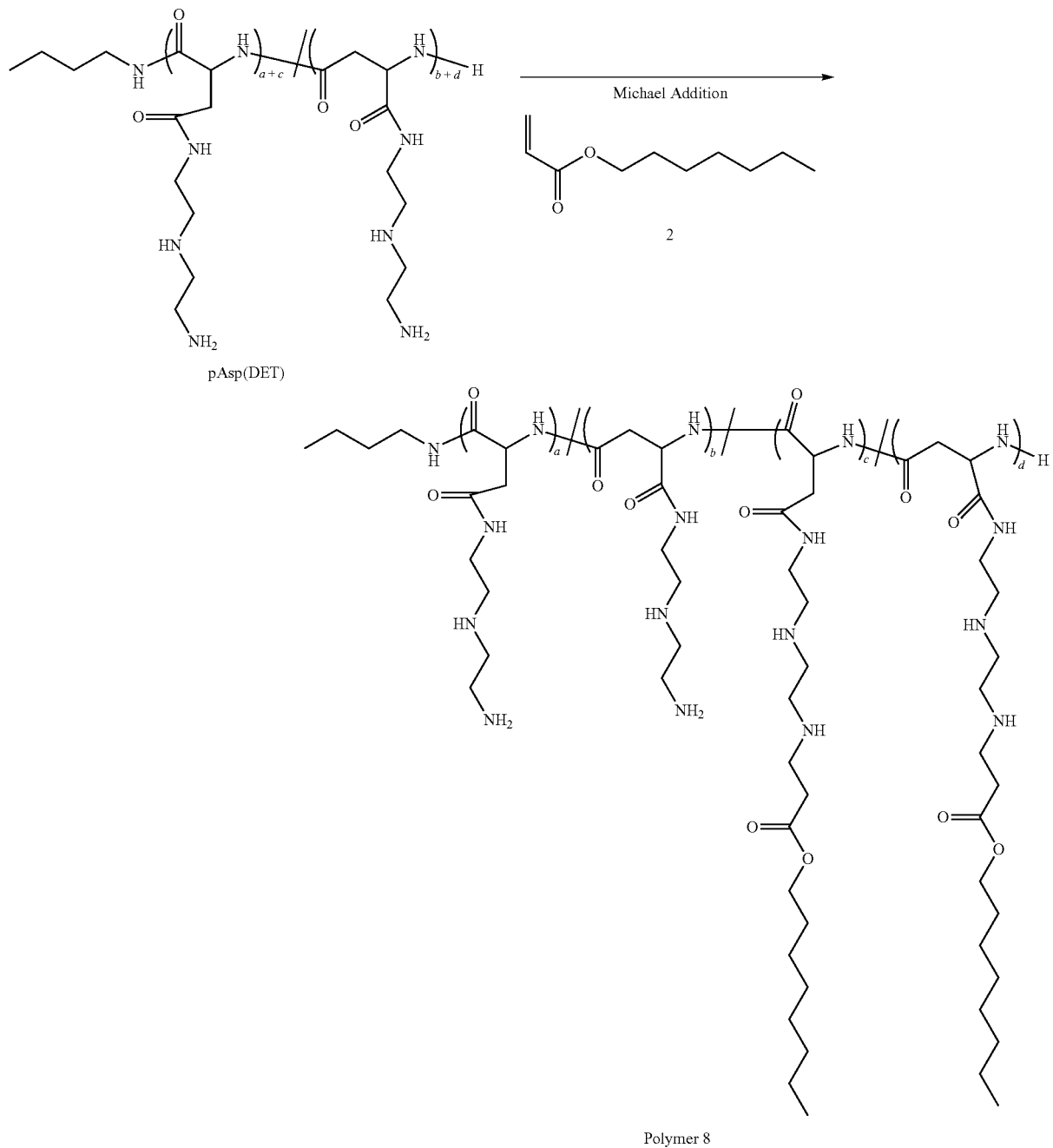

In a glass vial pASP(DET) (5 mg, 0.22 µmol) was suspended into anhydrous methanol (300 µL) and a 30 µL of triethylamine ("TEA") was added into the suspension. The resulting solution was stirred at room temperature for 10 min to completely dissolve the polymer. The solution was diluted with 300 µL of DCM. To the reaction mixture was added acrylate 2 (1.05 mg, 5.5 µmol) in 30 µL of DCM, and the reaction mixture was stirred at room temperature for 48 hours. The crude product was purified by precipitation in large excess of diethyl ether to yield 4.3 mg of Polymer 8, wherein (a+b) is 55 and (c+d) is 25. $^1$H NMR (400 MHz, $D_2O$): δ 4.8-4.6 (bs, 4H), 4.03 (t, 2H), 3.8-2.5 (m, 27H), 1.5 (t, 2H), 1.25 (s, 12H), 0.7 (t, 3H).

As demonstrated by Scheme 2, Michael Addition with acrylate 2 results in an amine-based bond (see, for example, Polymer 8). Thus, the original amine-functionality in pAsp (DET) remains intact.

Example 3

This example demonstrates the ability of the polymers described herein to deliver a Cas9 ribonucleoprotein ("Cas9 RNP") into the cell. The level of Cas9 RNP delivery was assessed using green fluorescent protein ("GFP") inducible HEK293T ("GFP-HEK") cells.

10 pmole of Cas9 RNP was mixed with (i) Polymer 5, (ii) Polymer 8, and (iii) pAsp(DET) as a control. GFP-HEK cells were treated with the resulting mixture in non-serum conditions. Polymers were added in dosages of 0.375 µg, 0.75 µg, 1.25 µg, 2.5 µg, 5 µg, and 10 µg to screen an optimal dose that gives the highest efficiency and minimal toxicity. The results are set forth in FIG. 3.

FIG. 3 shows the level of Cas9 RNP delivery as measured by the GFP(-) percent of the GFP-HEK cells treated with the three mixtures. All three polymers (i.e., Polymer 5, Polymer 8, and pAsp(DET)) showed similar levels of gene editing at polymer dosages of 0.375 µg to 2.5 µg. However, Polymer 8 and pAsp(DET) showed significant levels of cell toxicity (cell viability less than 50%) at polymer dosages of 5 µg and 10 µg. Whereas, Polymer 5 showed optimal delivery at a polymer dosage of 5 µg, as demonstrated by the level of GFP %, without significant toxicity.

Example 4

This example demonstrates the ability of the polymers described herein to deliver Cre recombinase, which can change loxP sequences, into the cell.

Figure 4:
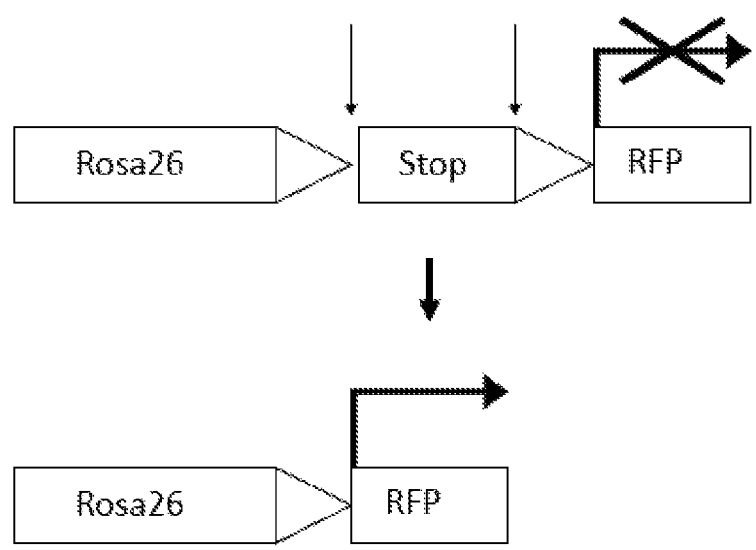
FIG. 4 is a schematic illustration of an ai9 reporter allele.

Using primary myoblasts from ai9 mice, which have a stop sequence in between loxP (see gray arrow in FIG. 4), the level of Cre recombinase delivered can be measured by RFP expression. Ai9 reporter allele contains a STOP cassette, which is flanked by the loxP sequence, thereby preventing RFP transcription. Cre recombinase removes the STOP cassette, flanked by the loxP sequence, and allows transcription of RFP.

Cre recombinase (2 ug) was mixed with was mixed with (i) Polymer 5 and (ii) pAsp(DET) as a control to produce nanoparticles. Polymers were added in dosages of 1.25 µg, 2.5 µg, 5 µg, 10 µg, and 20 µg to screen an optimal dose that gives the highest efficiency and minimal toxicity. Ai9 myoblasts were treated with the resulting nanoparticles, and the RFP+ population was quantified using flow cytometry 4 days after treatment. The results are set forth in FIG. 5.

Figure 5:
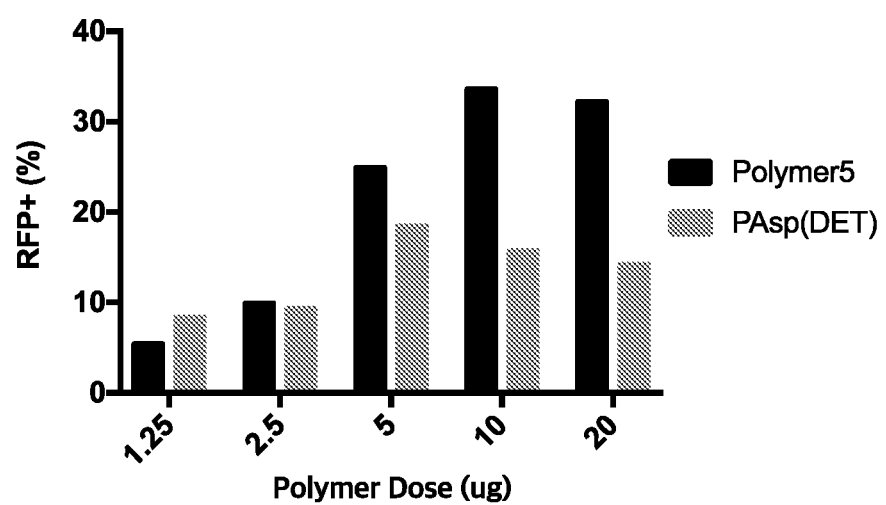
FIG. 5 shows the level of Cre recombinase delivery to primary myoblasts as measured by the amount of RFP+ expression at different concentrations of polymer/Cre compositions.

FIG. 5 shows the level of Cre recombinase delivery to primary myoblasts as measured by the amount of RFP+ expression. As shown in FIG. 5, Polymer 5 produced higher levels of RFP+ expression than the control (pAsp(DET)) at polymer dosages of 5 µg, 10 µg, and 20 µg, thereby demonstrating that Polymer 5 was more efficient at Cre recombinase delivery than pAsp(DET) at higher dosages.

Example 5

This example demonstrates the ability of the polymers described herein to deliver Cre recombinase in vivo in mice.

Ai9 mice were injected with (i) Cre recombinase only and (ii) a PEGylated polymer nanoparticle (i.e., a mixture of Polymer 5 and PEG-polymer) encapsulating Cre recombinase. Cre recombinase (35 ug) was delivered with a Polymer 5 and PEG-PAsp(DET) mixture (100 ug). Co-mixing of Polymer 5 and PEG-PAsp(DET) helps to control the size of polymer nanoparticles. Gastrocnemius muscle was harvested from ai9 mice two weeks after the injection. The harvested cross-sections of muscle were imaged to visualize red fluorescence protein that had been generated as a result of DNA recombination. The results are set forth in FIG. 6.

Figure 6:
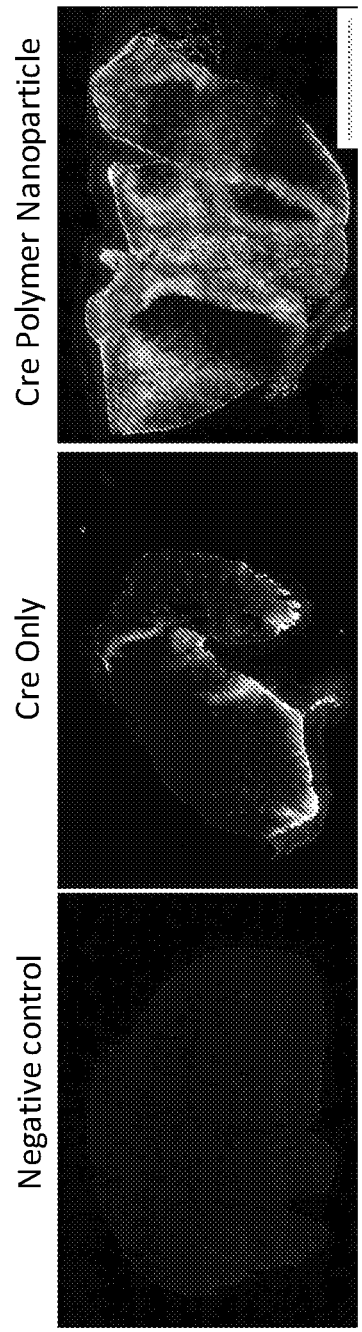
FIG. 6 illustrates the level of Cre recombinase delivery in mouse muscle visualized by red fluorescence protein (lighter-colored portions indicate fluorescence).

FIG. 6 shows that Cre recombinase delivery in mouse muscle was enhanced by the polymer nanoparticle. Injection with Cre recombinase only resulted in RFP expression in limited areas of muscle, as demonstrated by less red fluorescence protein visualized. Whereas, injection with Cre recombinase encapsulated by the polymer nanoparticle shows RFP expression in most of areas in gastrocnemius muscle.

A challenge of protein delivery is how widely protein can be delivered and affect large areas of tissue. The nanoparticle derived from a mixture of Polymer 5 and PEG-polymer can efficiently deliver and help distribution of Cre recombinase in ai9 mice.

Example 6

This example demonstrates the ability of the polymers described herein to deliver Cas9 to GFP expressing neuronal cells.

GFP expressing neuronal cells, which were differentiated from neuronal progenitor cells, were used to investigate whether Polymer 5 can deliver Cas9 RNP into neuronal cells. GFP expressing neuronal cells were treated with sgRNA and Cas9 protein using polymers described herein as a delivery method. Seven days after the treatment, genomic DNA was extracted from the cells and PCR amplification of GFP gene was conducted. TIDE analysis (TIDE software by Desktop Genetics, Netherlands Cancer Institute) was conducted to measure the frequency of indel mutation due to gene editing by Cas9. The results are set forth in FIG. 7.

Figure 7:
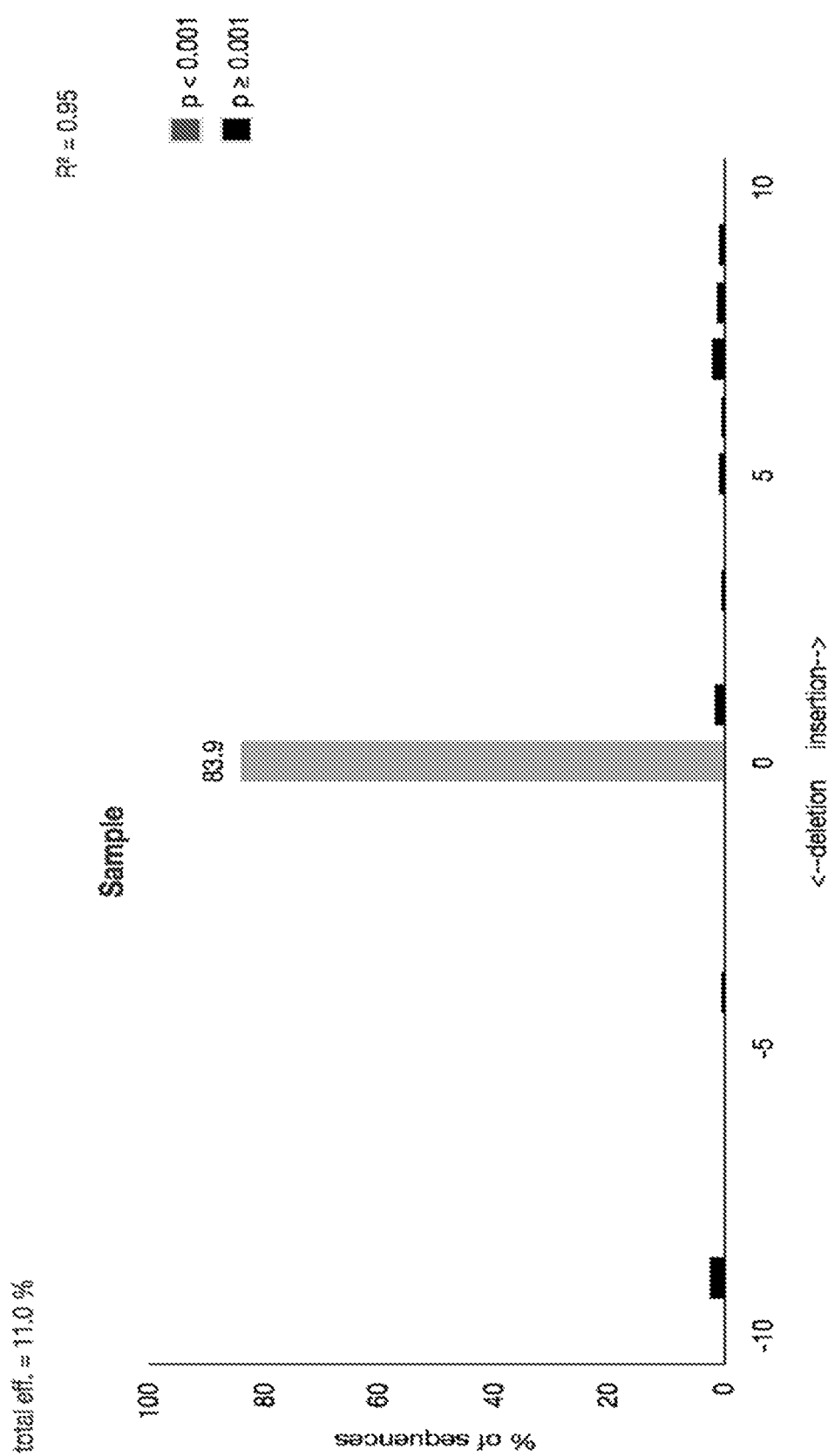
FIG. 7 shows the indel mutation rate of human neuronal stem cells exhibited by Cas9 delivery.

As demonstrated by FIG. 7, Polymer 5 was able to deliver Cas9 RNP and induced 11% indel mutation in neuronal cells.

Example 7

This example provides guidance for the synthesis of a polymer described herein. The synthesis includes a ring-opening polymerization, followed by further modification, to produce a polymer of Formula 4. An exemplary procedure is as follows.

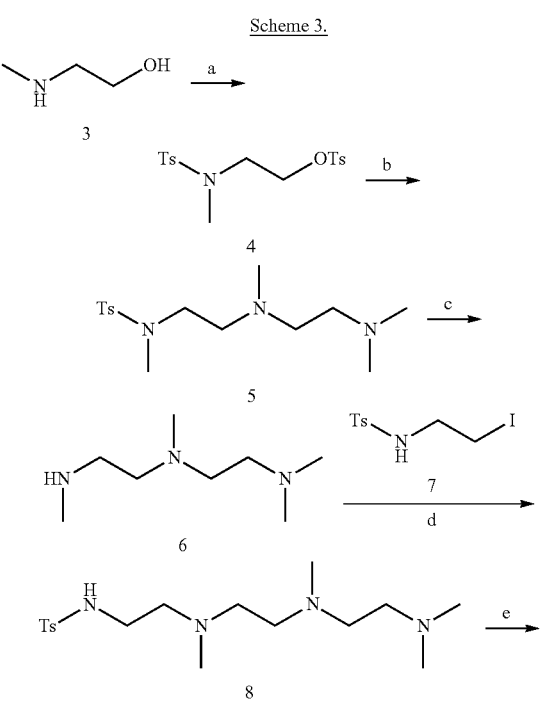

Scheme 3.

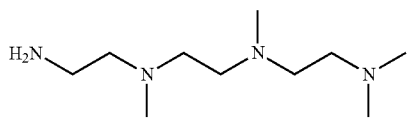

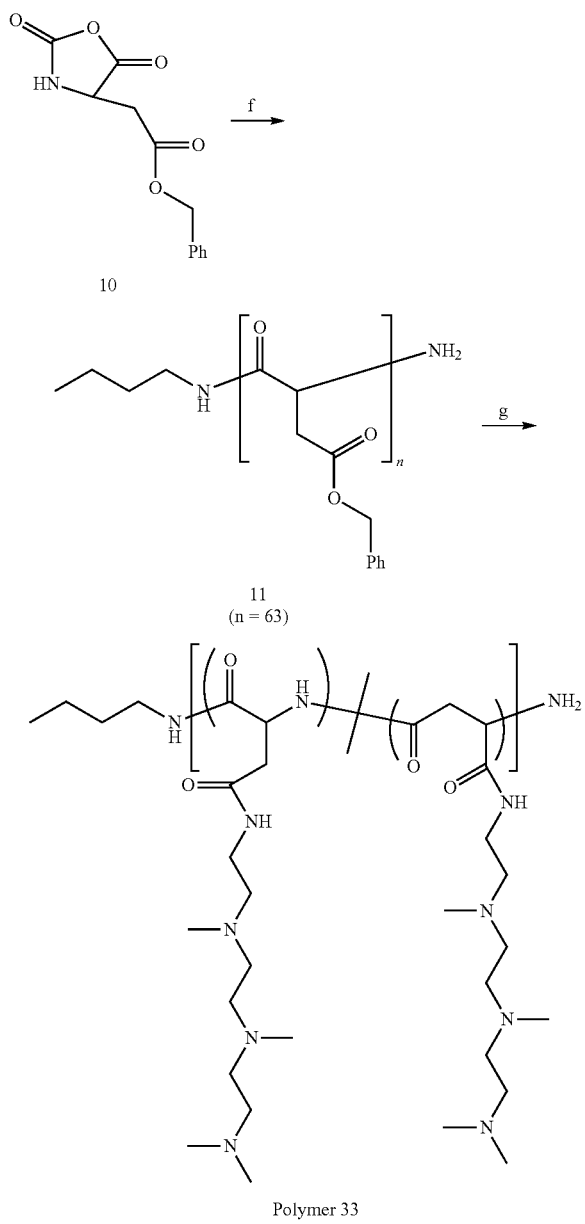

Polymer 33

Synthesis of Polymer 33: (a) Tosyl Chloride, TEA, DCM; (b) N,N,N-trimethylethylenediamine, $K_2CO_3$, Acetonitrile, reflux; (c) $LiAlH_4$, THF; (d) 7, $K_2CO_3$, acetonitrile, reflux; (e) $LiAlH_4$, THF; (f) butylamine, DCM-DMF (9:1), 48 hours; (g) 9, NMP, 6 hours.

As demonstrated by Scheme 3, ring-opening polymerization of compound 10 results in propagation to form compound 11 with n=63, which can be further modified to form Polymer 33 upon treatment with compound 9.

A similar procedure can be used to prepare other polymers of Formula 4 (e.g., polymers 30-32). Additionally, the terminal tertiary amine on the sidechains of the polymer can be demethylated by routine techniques to provide polymers 39-42.

Example 8

This example demonstrates the ability of the polymers described herein to deliver Cre recombinase, which can change loxP sequences, into the cell.

Figure 8:
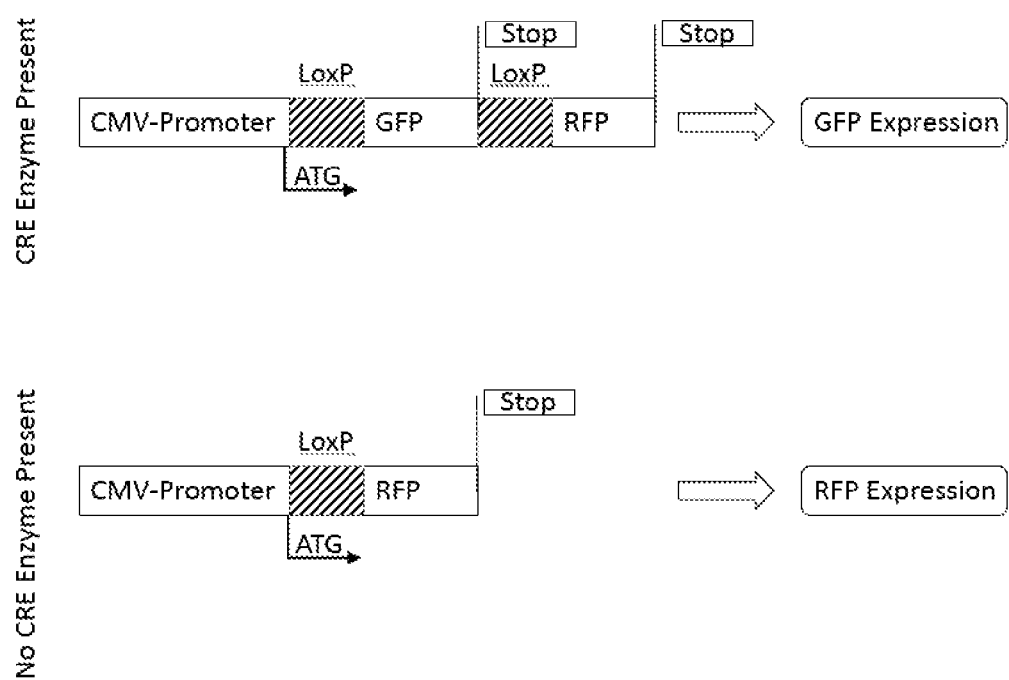
FIG. 8 is a schematic illustration of a traffic light reporter in HEK 293T.

Using traffic light reporter (TLR)-HEK 293T cells, which were generated with viral transduction of traffic light reporter in HEK 293T (see FIG. 8), the level of Cre recombinase delivered can be measured by red fluorescent protein ("RFP") expression. The traffic light reporter in HEK 293T contains a STOP cassette, and two loxP sequences that flank a GFP sequence, thereby preventing RFP transcription, and in turn expressing GFP in the absence of Cre. Cre recombinase removes the loxP sequences, and allows transcription of RFP.

Cre recombinase (1 ug) was mixed with Polymer 33 as prepared in Example 7, or pAsp(DET) as a comparative, to produce nanoparticles. Polymers were added in dosages of 1.25 μg or 2.5 μg to screen an optimal dose that gives the highest efficiency and minimal toxicity. TLR-HEK293T cells were treated with the resulting nanoparticles, and the RFP+ population was quantified using flow cytometry 3 days after treatment. The results are set forth in FIG. 9.

Figure 9:
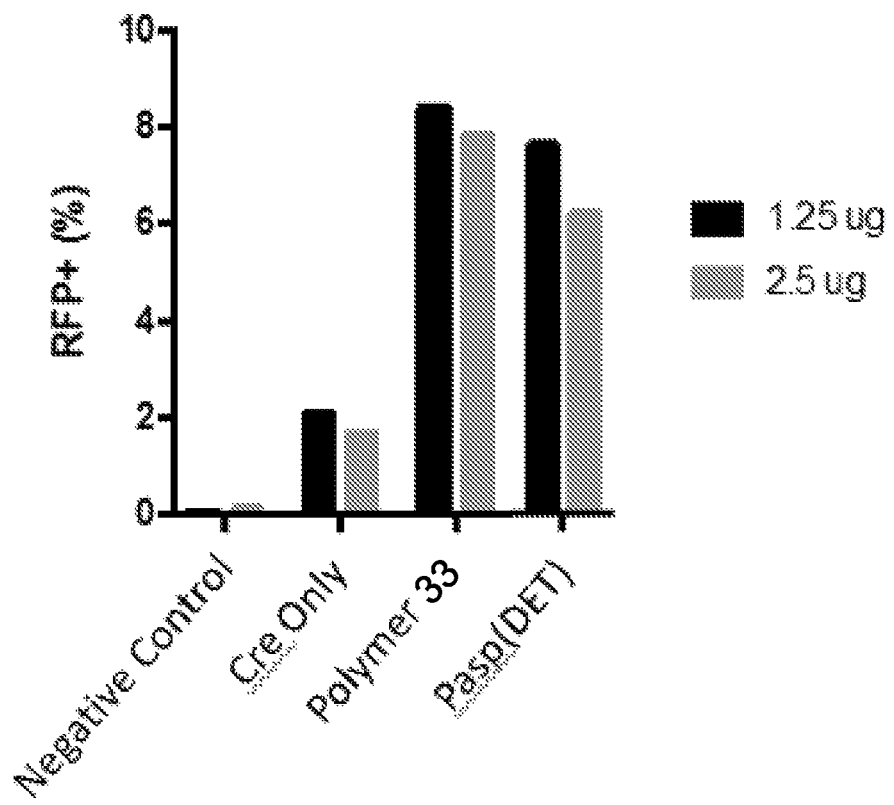
FIG. 9 shows the level of Cre recombinase delivery to TLR-HEK 293T as measured by the amount of RFP+ expression at different concentrations of polymer/Cre compositions.

FIG. 9 shows the level of Cre recombinase delivery to (TLR)-HEK 293T cells as measured by the amount of RFP+ expression. As shown in FIG. 9, Polymer 33 provided enhanced delivery over the samples containing Cre only and the comparative, pAsp(DET), at polymer dosages of 1.25 μg and 2.5 μg.

Example 9

This example demonstrates the ability of the polymers described herein to deliver a Cas9 ribonucleoprotein ("Cas9 RNP") into the cell. The level of Cas9 RNP delivery was assessed using green fluorescent protein ("GFP") inducible HEK293T ("GFP-HEK") cells.

15 pmole of Cas9 RNP (sgRNA+Cas9 Protein) was mixed with Polymer 33 as prepared in Example 7, or pAsp(DET) as a comparative, to produce nanoparticles. Polymers were added in dosages 2.5 μg. GFP-HEK cells were treated with the resulting mixture in non-serum conditions. The results are set forth in FIG. 10.

Figure 10:
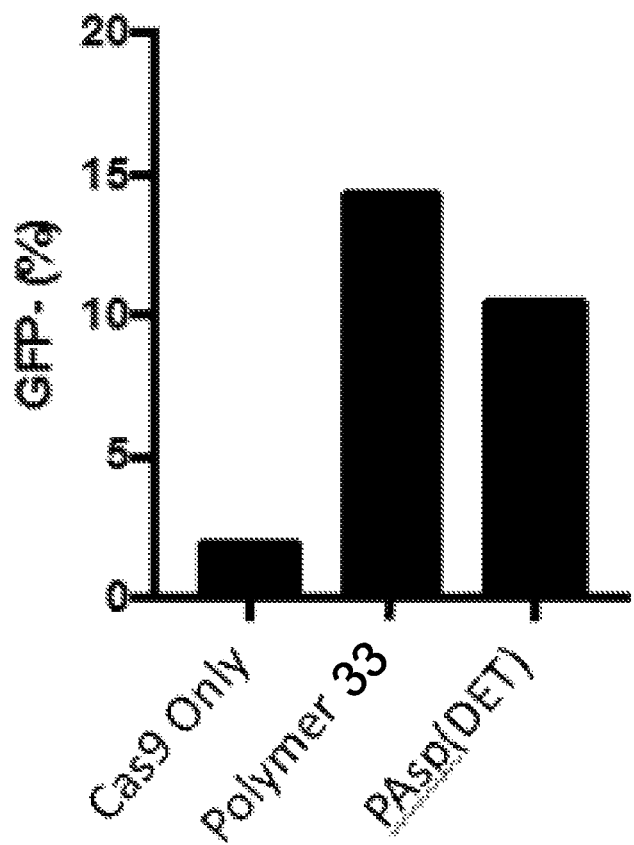
FIG. 10 is a graph of the level of Cas9 RNP delivery as measured by green fluorescence protein ("GFP") % in GFP-HEK cells at different dosages of polymer/Cas9 compositions.

FIG. 10 shows the level of Cas9 RNP delivery as measured by the GFP % of the GFP-HEK cells treated with the two mixtures. Both polymers (i.e., Polymer 33 and pAsp (DET)) showed an ability to deliver Cas9 RNP at a polymer dosage of 2.5 μg, relative to the control. However, Polymer 33 outperformed pAsp(DET) at a polymer dosage of 2.5 μg.

Example 10

This example demonstrates the ability of the polymers described herein to deliver nucleic acids. The level of eGFP mRNA delivery to HEK 293T cells was assessed using green fluorescent protein ("GFP").

eGFP mRNA (200 ng) was mixed with Polymer 33 (600 ng) as prepared in Example 7, and incubated for 5 min. The resulting polymer nanoparticles were treated to HEK 293T cells in OptiMEM medium. After 24 hours, the cells were detached from the plate and analyzed with flow cytometry. Lipofectamine was used as a positive control for eGFP mRNA delivery. The results are set forth in FIG. 11.

Figure 11:
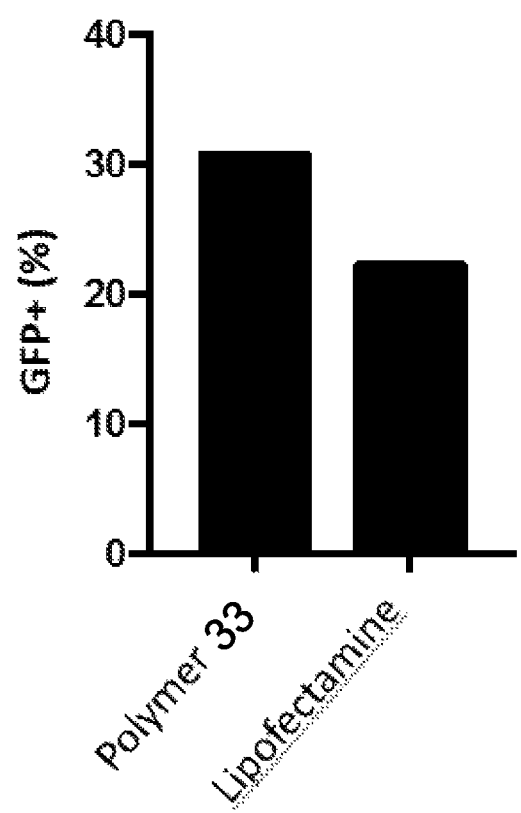
FIG. 11 illustrates the level of eGFP mRNA delivery to HEK 293T cells as measured by GFP %.

FIG. 11 shows that relative to the control, Polymer 33 provides increased delivery of eGFP mRNA to HEK 293T cells.

Example 11

This example demonstrates the effect incubation time has on the ability of the polymers described herein to deliver nucleic acids. The level of eGFP mRNA delivery to HEK 293T cells was assessed using green fluorescent protein ("GFP").

eGFP mRNA (200 ng) was mixed with Polymer 33 (1.2 µg) as prepared in Example 7, and incubated for periods of 2 min, 5 min, 10 min, and 30 min. The resulting polymer nanoparticles were treated to HEK 293T cells in OptiMEM medium. After 24 hours, the cells were detached from the plate and analyzed with flow cytometry. Lipofectamine was used as a positive control for eGFP mRNA delivery. The results are set forth in FIG. 12.

Figure 12:
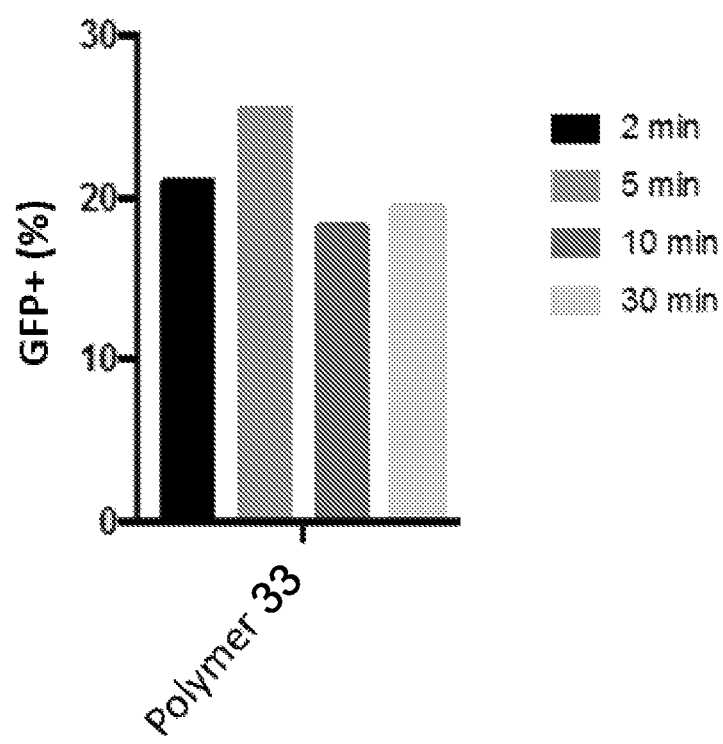
FIG. 12 shows the incubation time dependence of the level of eGFP mRNA delivery to HEK 293T cells as measured by GFP %.

FIG. 12 shows that nanoparticles formed within 2 minutes of incubation and polymer 33 provided efficient delivery of eGFP mRNA at all incubation times.

Example 12

This example demonstrates the ability of the polymers described herein to deliver mRNA. The level of red fluorescent protein ("RFP") mRNA delivery to HEK 293T cells was assessed using RFP+ expression.

RFP mRNA (200 ng) was mixed with Polymer 33 as prepared in Example 7, or pAsp(DET) as a comparative to produce nanoparticles. Polymer 33 and pAsp(DET) were added in dosages of (i) 600 ng or (ii) 480 ng in combination with 120 ng of a 1.5 kDa PEG-PAsp(DET) polymer. The 1.5 kDa PEG-PAsp(DET) polymer can help play a role in controlling the size of the nanoparticles. TLR-HEK293T cells were treated with the resulting nanoparticles, and the RFP+ population was quantified using flow cytometry 24 hours after treatment. The results are set forth in FIG. 13.

Figure 13:
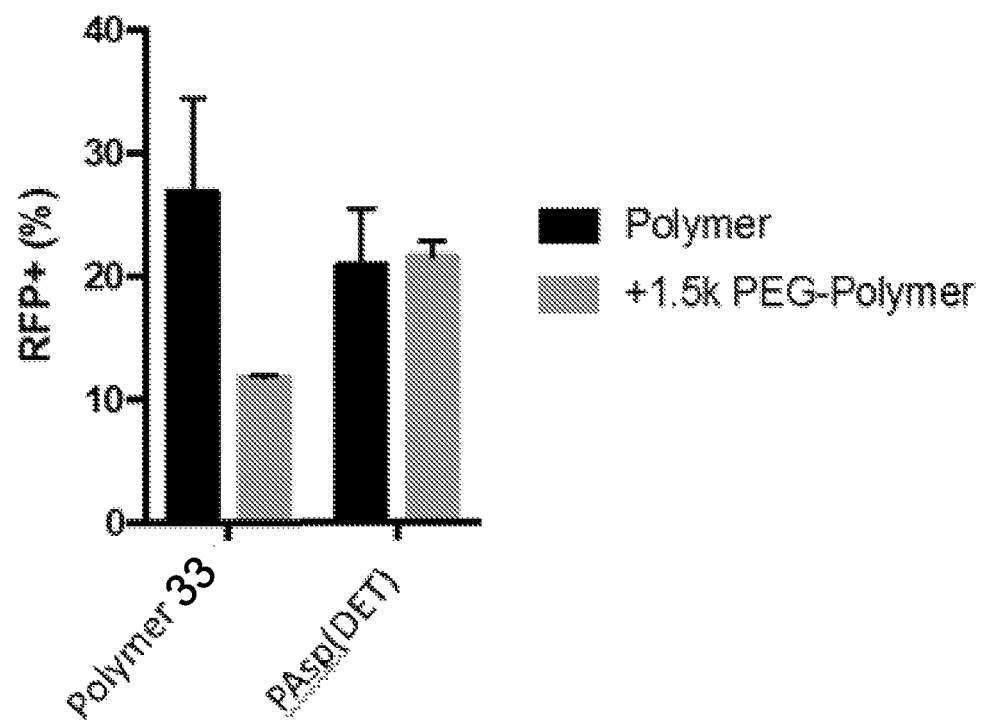
FIG. 13 illustrates level of red fluorescent protein ("RFP") mRNA delivery to HEK 293T cells as measured by RFP+ expression in both the presence and absence of a 1.5 kDa PEG-PAsp(DET) polymer.

FIG. 13 shows that relative to the comparative polymer (PAsp(DET)), Polymer 33 improved delivery of mRNAs to HEK 293T cells in the absence of the 1.5 kDa PEG-PAsp (DET) polymer. In addition, FIG. 13 shows that 600 ng of Polymer 33 provides more efficient delivery of mRNAs to HEK 293T cells than 480 ng Polymer 33 in combination with 120 ng of a 1.5 kDa PEG-PAsp(DET) polymer.

Example 13

This example demonstrates the ability of the polymers described herein to deliver mRNAs. The level of red fluorescent protein ("RFP") mRNA delivery to HEK 293T cells was assessed using RFP+ expression.

RFP mRNA (200 ng) was mixed with Polymer 33 as prepared in Example 7, or pAsp(DET) as a comparative to produce nanoparticles. Polymer 33 and pAsp(DET) were added in dosages of (i) 1 µg or (ii) 800 ng in combination with 200 ng of a 1.5 kDa PEG-PAsp(DET) polymer. The 1.5 kDa PEG-PAsp(DET) polymer can help play a role in controlling the size of the nanoparticles. TLR-HEK293T cells were treated with the resulting nanoparticles, and the RFP+ population was quantified using flow cytometry 24 hours after treatment. The results are set forth in FIG. 14.

Figure 14:
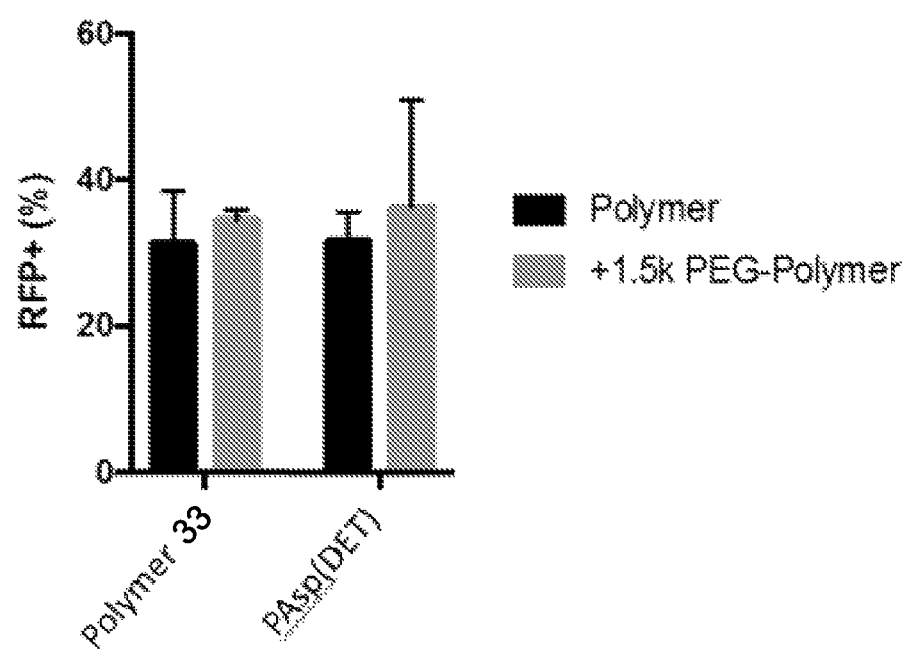
FIG. 14 illustrates level of red fluorescent protein ("RFP") mRNA to HEK 293T cells as measured by RFP+ expression in both the presence and absence of a 1.5 kDa PEG-PAsp (DET) polymer.

FIG. 14 shows that relative to the comparative polymer (PAsp(DET)), Polymer 33 provides comparable delivery of mRNA to HEK 293T cells, both in the presence and in the absence of the 1.5 kDa PEG-PAsp(DET) polymer at dosages of (i) 1 µg or (ii) 800 ng in combination with 200 ng of a 1.5 kDa PEG-PAsp(DET) polymer.

Example 14

This example demonstrates the ability of the polymers described herein to deliver a Cas9 ribonucleoprotein ("Cas9 RNP") into the cell using different buffers. The level of Cas9 RNP delivery was assessed using green fluorescent protein ("GFP") inducible HEK293T ("GFP-HEK") cells.

30 pmole of Cas9 RNP (sgRNA+Cas9 Protein) was mixed with 4 µg of Polymer 33 as prepared in Example 7 or 5 µg of or pAsp(DET) as a comparative, to produce nanoparticles. GFP-HEK cells (200,000 cells) were treated under three different buffer conditions, namely (i) (4-(2-hydroxyethyl)-1-piperazineethanesulfonic acid) ("HEPES"; 20 mM), (ii) Opti-MEM™ (commercially available from Thermo Fisher Scientific; Waltham, Mass.), or Dulbecco's Modified Eagle's Medium ("DMEM"; commercially available from Thermo Fisher Scientific; Waltham, Mass.). The results are set forth in FIG. 15.

Figure 15:
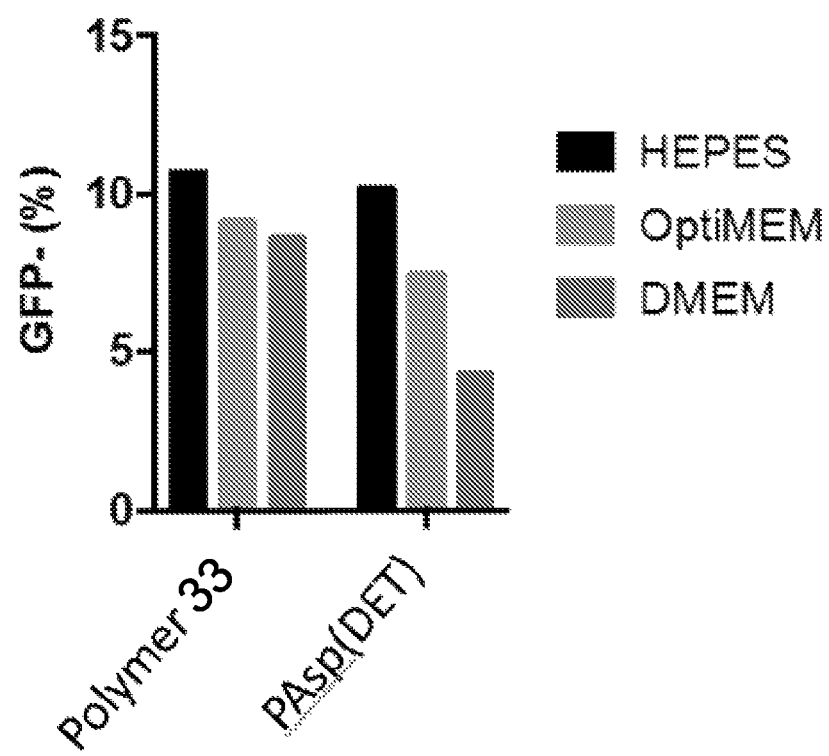
FIG. 15 is a graph of the level of Cas9 RNP delivery as measured by green fluorescence protein ("GFP") % in GFP-HEK cells for polymer/Cas9 nanoparticles in a buffer.

FIG. 15 shows the level of Cas9 RNP delivery as measured by the GFP(−) percent of the GFP-HEK cells treated with the two mixtures (i.e., 4 µg of Polymer 33 or 5 µg of or pAsp(DET)) under the three different buffer conditions. Both polymers (i.e., Polymer 33 and pAsp(DET)) showed the same trend for the three different buffers, with HEPES outperforming Opti-MEM™, and Opti-MEM™ outperforming DMEM. In addition, Polymer 33 outperformed pAsp(DET) in all three buffers.

Example 15

This example demonstrates the ability of the polymers described herein to stably encapsulate a nucleic acid.

Figure 18:
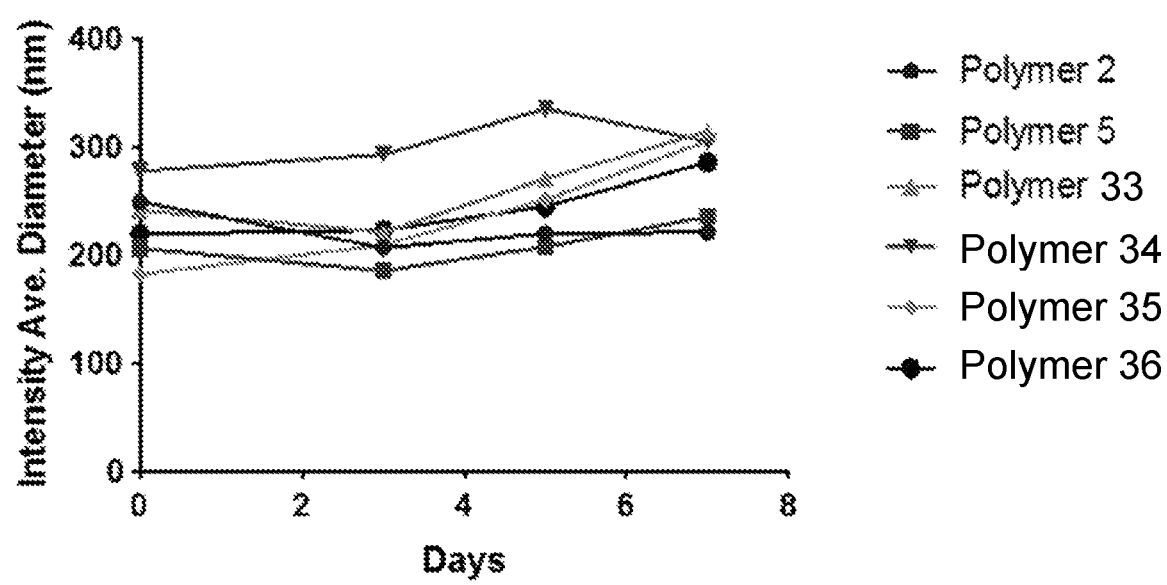
FIG. 18 is a graph showing the intensity averaged particle diameter (nm) of Polymers 2, 5, 33, 34, 35, and 36 as a function of time.

Polymers 2, 5, and 33 of the present disclosure (1 ug/uL, 10 mM HEPES) was pipet mixed with oligionucleotdies (1 ug/uL, 10 mM HEPES) at a 5:1 mass ratio, and then left for 10 minutes at room temperature to form nanoparticles. They were stored at 4 C when not in use. Nanoparticles from stock were diluted at ~1:20 ratio with 10 mM HEPES and characterized by dynamic light scattering (DLS) at 0, 3, 5 and 7 days (n=1) post preparation. Intensity averaged particle size is displayed in FIG. 18.

Nanoparticle size between 150 nm to 350 nm was observed. The polymers showed minimal size changes over 7 days, indicating that the nanoparticles were stable. pAsp [DET] was run as a control (data not shown), and demonstrated a somewhat greater size change by day 7 than the other tested nanoparticles.

Example 16

This example demonstrates the preparation of a polymer according to the disclosure To a 100 mg (0.0074 mmol) of poly(O-benzyl 1-aspartate) (PBLA) was dissolved Into 3 mL of NMP. To this reaction mixture was added 1.5 gm of 1,4,7,10-tetramethyl-triethylenetetraamine and reaction was stirred for 16 h at RT. Crude reaction mixture was precipitated into diethyl ether and the crude product was collected via centrifuge (5000 g for 15 min). Crude product was dissolved into 3 mL of 1M HCl and dialyzed against water to achieve resulting pH=6. The resulting polymer solution was lyophilized to obtain polymer 41 as a white power.

Example 17

This example demonstrates the use of the polymers described herein to deliver mRNA to a cell.

mRNA encoding green or red fluorescent protein was mixed with test polymer and combined with one of several different cell types as indicated in Table 2. Transfection was measured as a function of fluoresence. The results are presented in Table 2, which shows that almost all polymers produced some level of transfection in at least one cell type.

TABLE 2

| Polymer | Hepatocyte | | Mouse Primary Myoblast | | Human Neural Stem Cell | | HEK293 | Hematopoietic Stem Cell |
|---|---|---|---|---|---|---|---|---|
| | HUH-7 | HEPG2 | No-Serum | Serum | No-Serum | Serum | No-Serum | No-Serum |
| 1 | 0 | 0 | 0 | 0 | 0 | 1 | 0 | 0.0 |
| 2 | 0 | 0 | 0 | 0 | 0 | 1 | 0 | 4.1 |
| 3 | 0 | 0 | 0 | 1 | 12 | 1 | 0 | 0.3 |
| 4 | 0 | 0 | 0 | 0 | 0 | 1 | 1 | 0.0 |
| 5 | 0 | 0 | 3 | 1 | 19 | 3 | 12 | 0.2 |
| 6 | 0 | 0 | 0 | 0 | 0 | 0 | 0 | 0.0 |
| 7 | 9 | 0 | 0 | 1 | 7 | 3 | 6 | 1.9 |
| 8 | 7 | 0 | N/A | N/A | N/A | N/A | N/A | N/A |
| 9 | 0 | 0 | 25 | 0 | 4 | 2 | 3 | 0.9 |
| 10 | 0 | 0 | 8 | 0 | 25 | 3 | 19 | 0.7 |
| 11 | 0 | 0 | 23 | 0.5 | 18 | 4 | 25 | 0.2 |
| 12 | N/A | N/A | N/A | N/A | N/A | N/A | 9 | N/A |
| 33 | 0 | 0 | 26 | 2 | 41 | 4 | 27 | N/A |
| Lipofectamine | 84 | 43 | 39 | 52 | 49 | N/A | 26 | 0.0 |
| Mock | 0 | 0 | 0 | 0 | N/A | N/A | N/A | N/A |
| pAsp[DET] | 0 | 0 | N/A | N/A | 39 | 3 | 28 | 0.0 |

N/A = Not tested
Mock = polymer without mRNA
Mouse primary myoblast testing was performed using mRNA encoding green fluorescent protein. All other cell types were tested using mRNA encoding red fluorescent protein.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a complex" includes a plurality of such complexes and reference to "the Cas9 polypeptide" includes reference to one or more Cas9 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention claimed is:
1. A polymer comprising a structure of Formula 1:

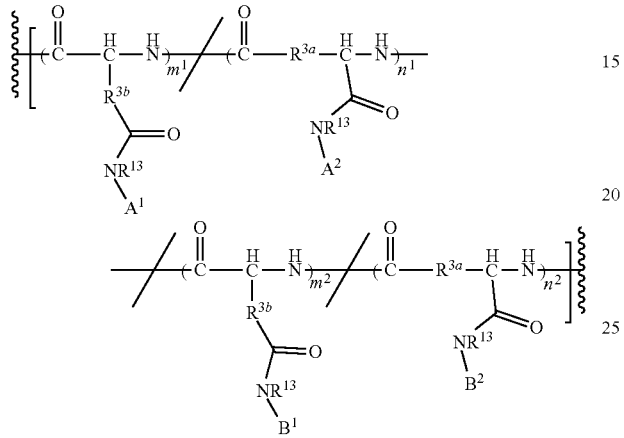

wherein:
  each of $m^1$ and $n^1$ is an integer from 0 to 1000;
  each of $m^2$ and $n^2$ is an integer from 0 to 1000, provided that the sum of $m^2+n^2$ is greater than 5;
  the symbol "/" indicates that the units separated thereby are linked randomly or in any order;
  $R^{3a}$ and $R^{3b}$ are each independently a methylene or ethylene group;
  each instance of $R^{13}$ is independently hydrogen or a $C_1$-$C_{12}$ alkyl group, alkenyl group, cycloalkyl group, or cycloalkenyl group;
  $A^1$ and $A^2$ are each independently a group of formula —(CH$_2$)$_{p1}$—[NR$^2$—(CH$_2$)$_{q1}$-]$_{r1}$NR$^2_2$;

—(CH$_2$)$_{p2}$—N[—(CH$_2$)$_{q2}$—NR$^2_2$]$_2$;

—(CH$_2$)$_{p3}$—N{[—(CH$_2$)$_{q3}$—NR$^2_2$][—(CH$_2$)$_{q4}$—NR$_2$-]$_{r2}$R$^2$}; or

—(CH$_2$)$_{p4}$—N{—(CH$_2$)$_{q5}$—N[—(CH$_2$)$_{q6}$—NR$^2_2$]$_2$}$_2$, $B^1$ and $B^2$ are each independently —(CH$_2$)$_{p1}$—[NR$^2$—(CH$_2$)$_{q1}$-]$_{r1}$NR$^2$—(CH$_2$)$_{s1}$—R$^4$—R$^5$;

—(CH$_2$)$_{p2}$—N[—(CH$_2$)$_{q2}$—NR$^2$—(CH$_2$)$_{s2}$—R$^4$—R$^5$]$_2$;

—(CH$_2$)$_{p3}$—N{[—(CH$_2$)$_{q3}$—NR$^2_2$][—(CH$_2$)$_{q4}$—NR$^2$-]$_{r2}$(CH$_2$)$_{s3}$—R$^4$—R$^5$};

—(CH$_2$)$_{p4}$—N{—(CH$_2$)$_{q5}$—N[—(CH$_2$)$_{q6}$—NR$^2$—(CH$_2$)$_{s4}$—R$^4$—R$^5$]$_2$}$_2$;

—(CH$_2$)$_{p1}$—[NR$^2$—(CH$_2$)$_{q1}$-]$_{r1}$NR$^2$—CH$_2$—CHOH—R$^5$;

—(CH$_2$)$_{p2}$—N[—(CH$_2$)$_{q2}$—NR$^2$—CH$_2$—CHOH—R$^5$]$_2$;

—(CH$_2$)$_{p3}$—N{[—(CH$_2$)$_{q3}$—NR$^2_2$][—(CH$_2$)$_{q4}$—NR$^2$-]$_{r2}$—CH$_2$—CHOH—R$^5$};

—(CH$_2$)$_{p4}$—N{—(CH$_2$)$_{q5}$—N[—(CH$_2$)$_{q6}$—NR$^2$—CH$_2$—CHOH—R$^5$]$_2$}$_2$;

—(CH$_2$)$_{p2}$—N[—(CH$_2$)$_{q2}$—NR$^2$—(CH$_2$)$_{s2}$—R$^5$]$_2$;

—(CH$_2$)$_{p3}$—N{[—(CH$_2$)$_{q3}$—NR$^2_2$][—(CH$_2$)$_{q4}$—NR$^2$-]$_{r2}$(CH$_2$)$_{s3}$—R$^5$};

—(CH$_2$)$_{p4}$—N{—(CH$_2$)$_{q5}$—N[—(CH$_2$)$_{q6}$—NR$^2$—(CH$_2$)$_{s4}$—R$^5$]$_2$}$_2$;

—(CH$_2$)$_{p1}$—[N{(CH$_2$)$_{s1}$—R$^4$—R$^5$}—(CH$_2$)$_{q1}$-]$_{r1}$NR$^2_2$; or

—(CH$_2$)$_{p1}$—[N{(CH$_2$)$_{s1}$—R$^5$}—(CH$_2$)$_{q1}$-]$_{r1}$NR$^2_2$, wherein p1 to p4, q1 to q6, r1 and r2, and s1 to s4 are each independently an integer of 1 to 5;

each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, heterocyclic group, or combination thereof optionally comprising from 1 to 8 secondary or tertiary amines or a substituent comprising a tissue-specific or cell-specific targeting moiety.

2. The polymer of claim 1, wherein each of $A^1$ and $A^2$ is a group of formula —(CH$_2$)$_2$—NH—(CH$_2$)$_2$—NH$_2$, and each of $B^1$ and $B^2$ is a group of formula —(CH$_2$)$_2$—NH—(CH$_2$)$_2$—NH—(CH$_2$)$_2$—R$^4$—R$^5$.

3. The polymer of claim 1 having the structure of Formula 1A:

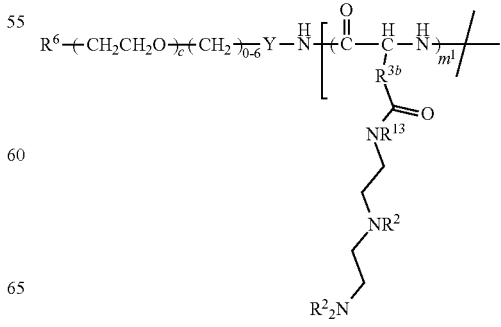

-continued

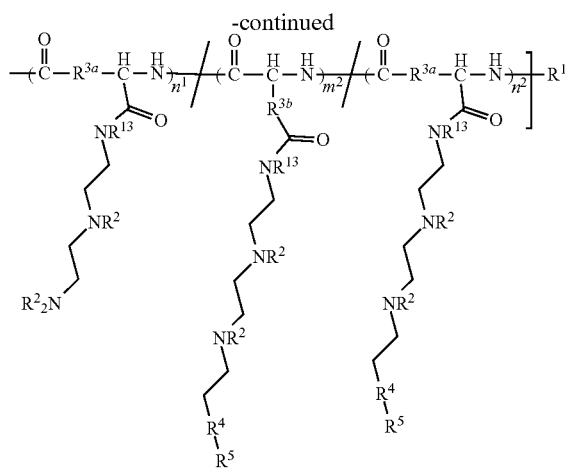

wherein
- c is an integer from 0 to 50;
- Y is optionally present and is a cleavable linker;
- each of $m^1$ and $n^1$ is an integer from 0 to 1000;
- each of $m^2$ and $n^2$ is an integer from 0 to 1000, provided that the sum of $m^2+n^2$ is greater than 5;
- the symbol "/" indicates that the units separated thereby are linked randomly or in any order;
- $R^1$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;
- each instance of $R^2$ is independently hydrogen or a $C_1$-$C_{12}$ alkyl group, alkenyl group, cycloalkyl group, or cycloalkenyl group;
- $R^{3a}$ and $R^{3a}$ are each independently a methylene or ethylene group;
- each instance of $R^{13}$ is independently hydrogen or a $C_1$-$C_{12}$ alkyl group, alkenyl group, cycloalkyl group, or cycloalkenyl group;
- each instance of $R^4$ is —C(O)O—, —C(O) NH—, or —S(O)(O)—;
- each instance of $R^5$ is independently an alkyl group, cycloalkyl group, alkenyl group, cycloalkenyl group, aryl group, heteroalkyl group, heterocyclic group, or combination thereof optionally comprising from 1 to 8 secondary or tertiary amines or a substituent comprising a tissue-specific or cell-specific targeting moiety; and
- $R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety.

4. The polymer of claim 1, wherein $R^4$ is —C(O)—O—.

5. The polymer of claim 1, wherein $R^5$ is

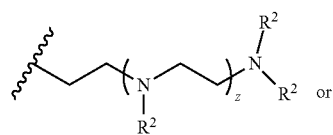 or

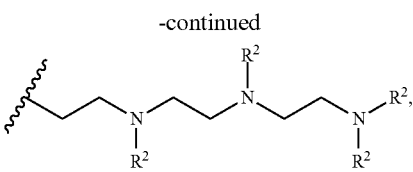

wherein z is an integer from 1 to 5.

6. The polymer of claim 1, wherein the ratio of $(m^1+n^1)/(m^2+n^2)$ is about 20 or less, and, optionally, about 0.2 or more.

7. The polymer of claim 1, wherein the tissue-specific or cell-specific targeting moiety is:

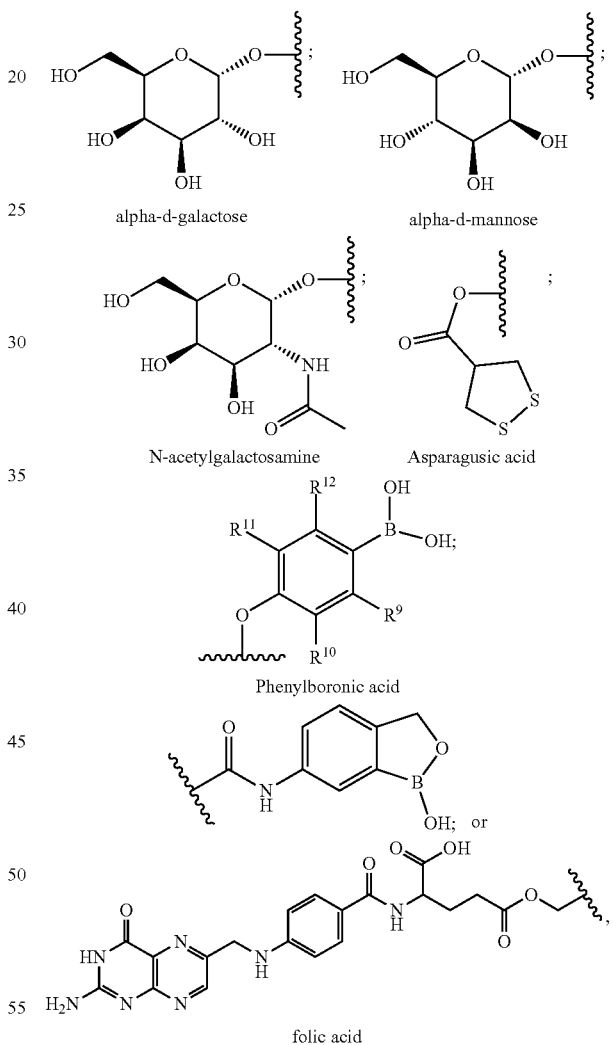

wherein each of $R^9$, $R^{10}$, $R^{11}$, and $R^{12}$ is independently hydrogen, halogen, $C_1$-$C_4$ alkyl, or $C_1$-$C_4$ alkoxy, optionally substituted with one or more amino groups; or an antibody or protein antigen.

8. The polymer of claim 1, wherein the polymer is a cationic polymer.

9. A composition comprising e the polymer of claim 1 and a nucleic acid and/or polypeptide.

10. The composition of claim 9, wherein the composition comprises a guide nucleic acid and/or donor nucleic acid; an RNA-guided endonuclease or nucleic acid encoding same; or combination thereof.

11. The composition of claim 10, wherein the RNA-guided endonuclease is Cas9, Cpf1, or a combination thereof.

12. The composition of claim 9, wherein the composition comprises a DNA recombinase, a zinc finger nuclease, a transcription activator-like effector nuclease, or a combination thereof.

13. The composition of claim 9, wherein the composition comprises a nanoparticle comprising the polymer and the nucleic acid and/or polypeptide.

14. The composition of claim 9, wherein the composition comprises a second polymer that comprises polyethylene oxide.

15. A method of delivering a nucleic acid and/or polypeptide to a cell, the method comprising administering the composition of claim 9 to the cell.

16. The method of claim 15, wherein the cell is in a subject and the composition is administered to the subject, and wherein the polymer comprises a tissue-specific targeting moiety that localizes the polymer to tissues of a peripheral nervous system, a central nervous system, liver, muscle, lung, bone, or an eye of the subject.

17. The method of claim 16, wherein the polymer comprises a targeting moiety that preferentially binds to tumor cells.

18. A polymer comprising a structure of Formula 1:

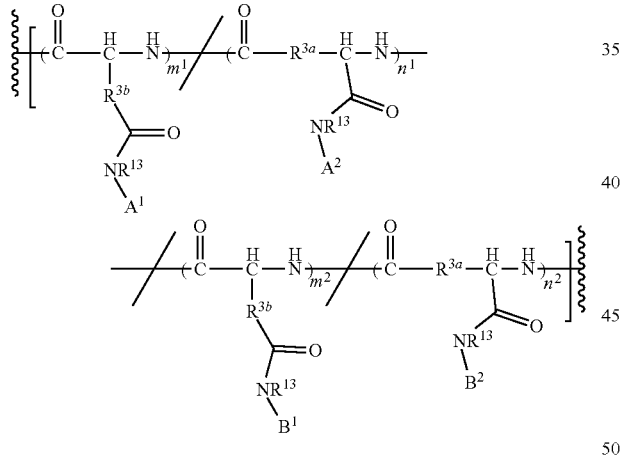

wherein:
each of $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
$R^{3a}$ and $R^{3b}$ are each independently a methylene or ethylene group;
each instance of $R^{13}$ is independently hydrogen or a $C_1$-$C_{12}$ alkyl group, alkenyl group, cycloalkyl group, or cycloalkenyl group;
$A^1$ and $A^2$ are each independently a group of formula —$(CH_2)_{p1}$—[$NR^2$—$(CH_2)_{q1}$-]$_{r1}NR^2_2$;

—$(CH_2)_{p2}N[$—$(CH_2)_{q2}$—$NR^2_2]_2$;

—$(CH_2)_{p3}$—N{[—$(CH_2)_{q3}$—$NR^2_2$][—$(CH_2)_{q4}$—$NR^2$-]$_{r2}R^2$}; or

—$(CH_2)_{p4}$—N{—$(CH_2)_{q5}$—N[—$(CH_2)_{q6}$—$NR^2_2]_2\}_2$, $B^1$ and $B^2$ are each independently —$(CH_2)_{p1}$—[$NR^2$—$(CH_2)_{q1}$-]$_{r1}NR^2$—$(CH_2)_{s1}$—$R^4$—$R^5$;

—$(CH_2)_{p2}$—N[—$(CH_2)_{q2}$—$NR^2$—$(CH_2)_{s2}$—$R^4$—$R^5]_2$;

—$(CH_2)_{p3}$—N{[—$(CH_2)_{q3}$—$NR^2_2$][—$(CH_2)_{q4}$—$NR^2$-]$_{r2}(CH_2)_{s3}$—$R^4$—$R^5$};

—$(CH_2)_{p4}$—N{—$(CH_2)_{q5}$—N[—$(CH_2)_{q6}$—$NR^2$—$(CH_2)_{s4}$—$R^4$—$R^5]_2\}_2$;

—$(CH_2)_{p1}$—[$NR^2$—$(CH_2)_{q1}$-]$_{r1}NR^2$—$CH_2$—CHOH—$R^5$;

—$(CH_2)_{p2}$—N[—$(CH_2)_{q2}$—$NR^2$—$CH_2$—CHOH—$R^5]_2$;

—$(CH_2)_{p3}$—N{[—$(CH_2)_{q3}$—$NR^2_2$][—$(CH_2)_{q4}$—$NR^2$-]$_{r2}$—$CH_2$—CHOH—$R^5$};

—$(CH_2)_{p4}$—N{—$(CH_2)_{q5}$—N[—$(CH_2)_{q6}$—$NR^2$—$CH_2$—CHOH—$R^5]_2\}_2$;

—$(CH_2)_{p2}$—N[—$(CH_2)_{q2}$—$NR^2$—$(CH_2)_{s2}$—$R^5]_2$;

—$(CH_2)_{p3}$—N{[—$(CH_2)_{q3}$—$NR^2_2$][—$(CH_2)_{q4}$—$NR^2$-]$_{r2}(CH_2)_{s3}$—$R^5$};

—$(CH_2)_{p4}$—N{—$(CH_2)_{q5}$—N[—$(CH_2)_{q6}$—$NR^2$—$(CH_2)_{s4}$—$R^5]_2\}_2$;

—$(CH_2)_{p1}$—[N{$(CH_2)_{s1}$—$R^4$—$R^5$}—$(CH_2)_{q1}$—]$_{r1}NR^2_2$; or

—$(CH_2)_{p1}$—[N{$(CH_2)_{s1}$—$R^5$}—$(CH_2)_{q1}$-]$_{r1}NR^2_2$, wherein p1 to p4, q1 to q6, r1 and r2, and s1 to s4 are each independently an integer of 1 to 5:
each instance of $R^2$ is independently hydrogen or a $C_1$-$C_{12}$ alkyl group, alkenyl group, cycloalkyl group, or cycloalkenyl group: each instance of $R^4$ is independently —C(O)O—, —C(O)NH—, or —S(O)(O)—; and each instance of $R^5$ is independently:

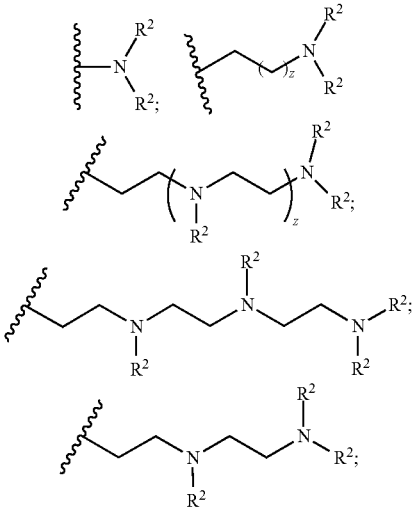

149
-continued

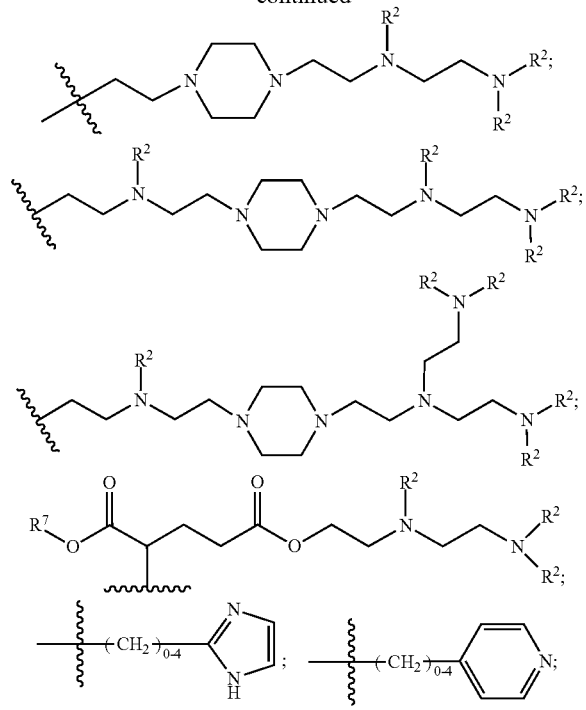

150
-continued

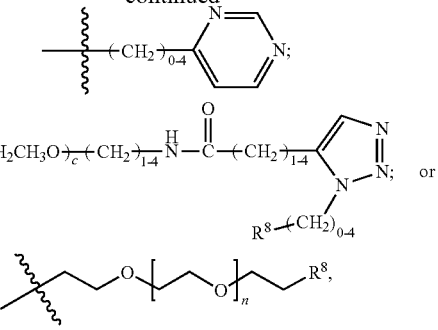

wherein
each instance of $R^2$ is independently hydrogen or a $C_1$-$C_{12}$ alkyl group, alkenyl group, cycloalkyl group, or cycloalkenyl group;
$R^7$ is a $C_1$-$C_{50}$ alkyl group, alkenyl group, cycloalkyl group, or cycloalkenyl group optionally substituted with one or more amines;
z is an integer from 1 to 5;
c is an integer from 0 to 50;
Y is optionally present and is a cleavable linker;
n is an integer from 0 to 50; and
$R^8$ is a tissue-specific or cell-specific targeting moiety.

19. A polymer of formula:

Polymer 1

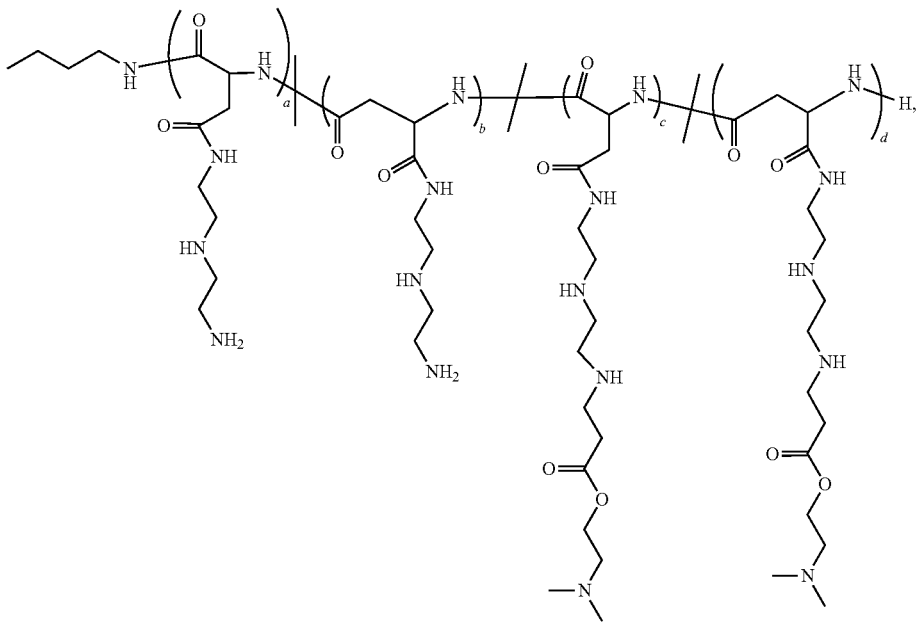

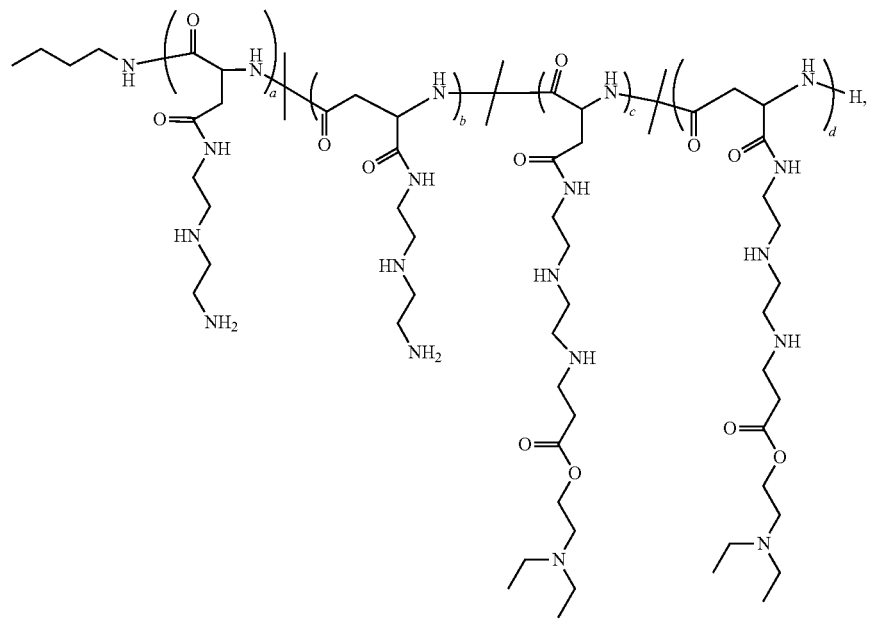
Polymer 2
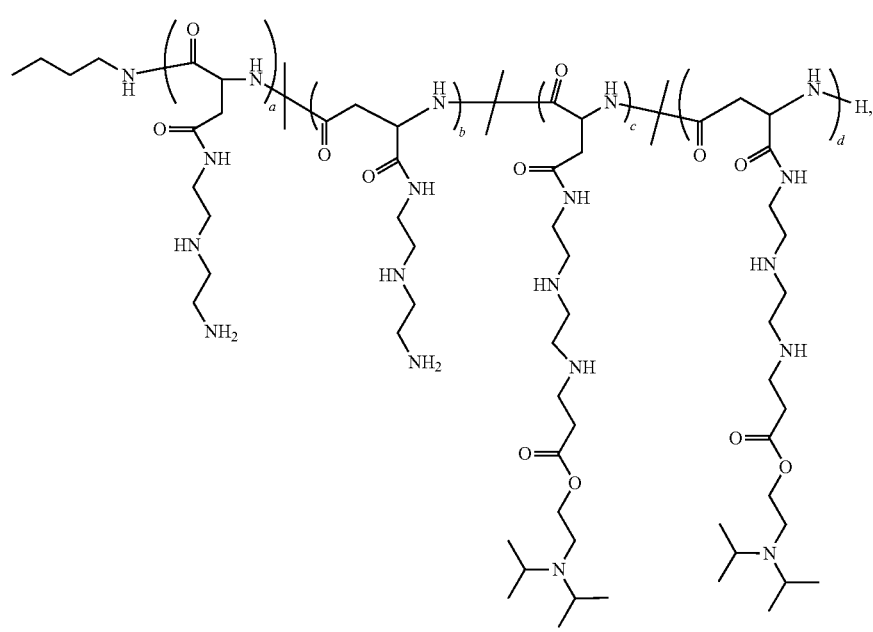
Polymer 3

Polymer 4
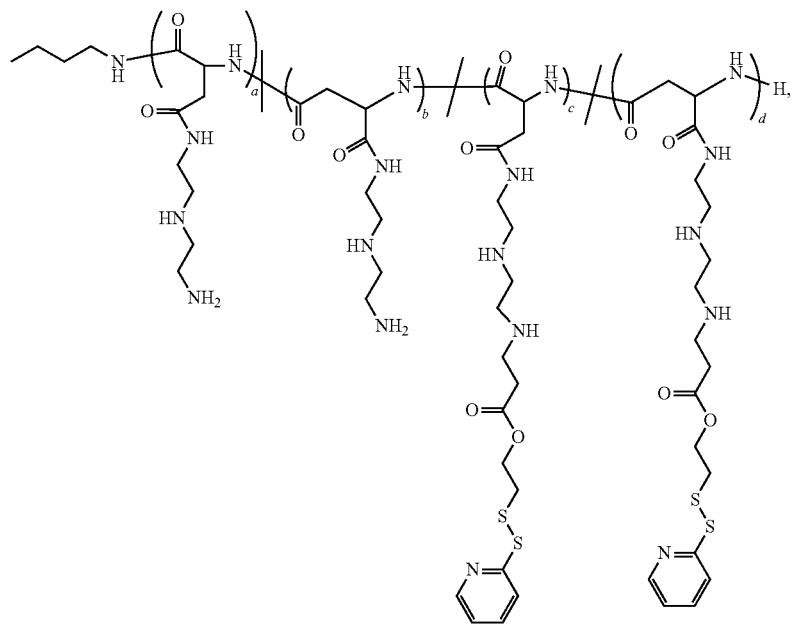
Polymer 5
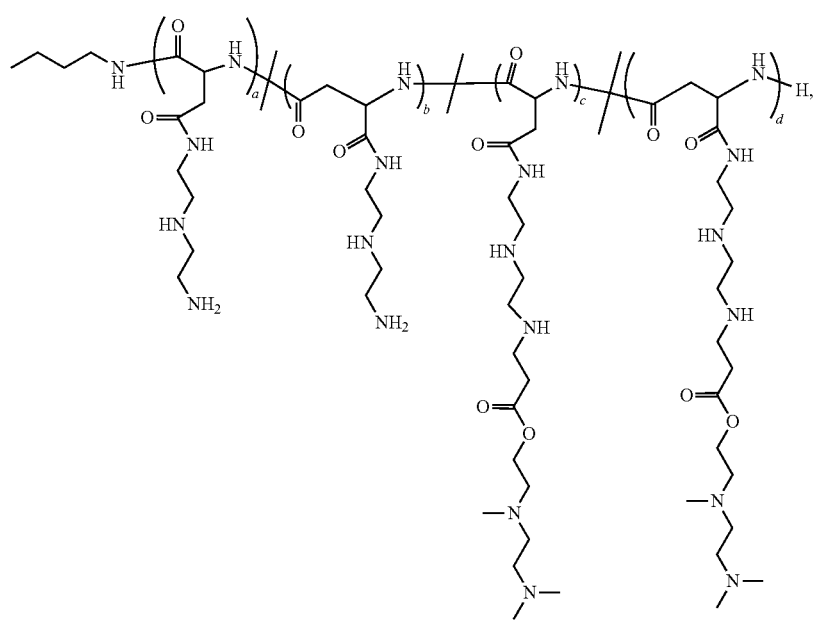

Polymer 6
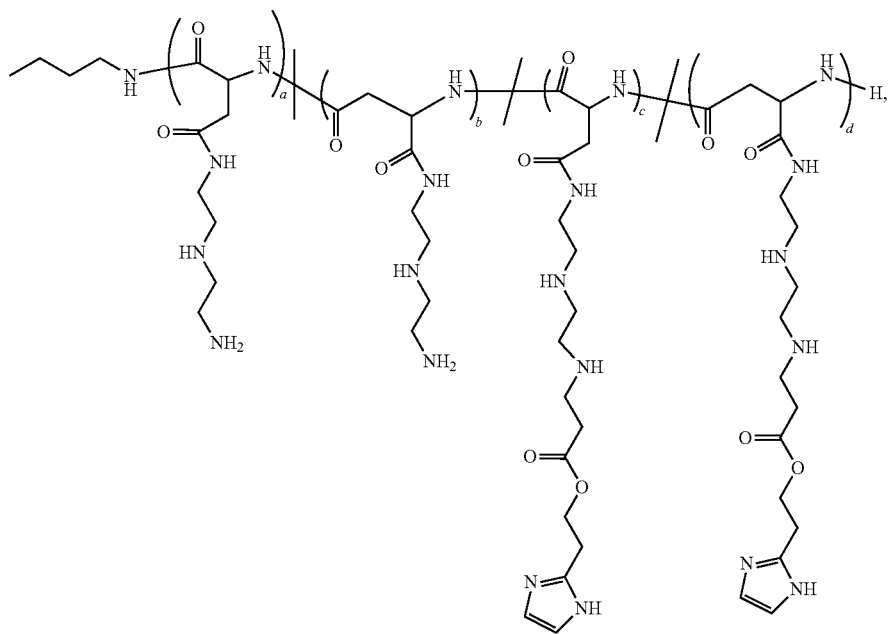
Polymer 7
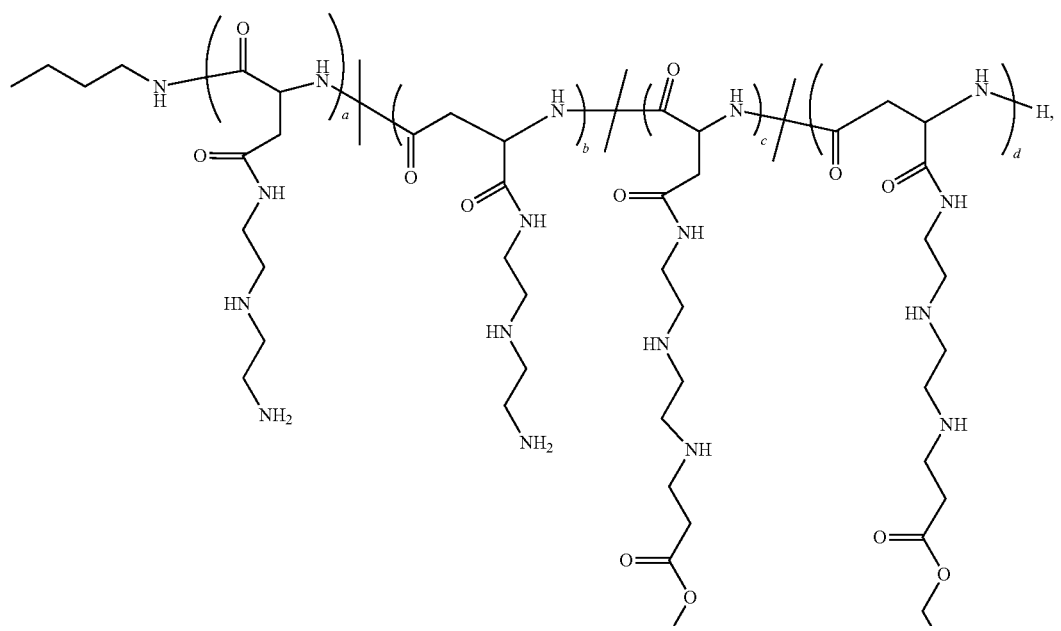

-continued
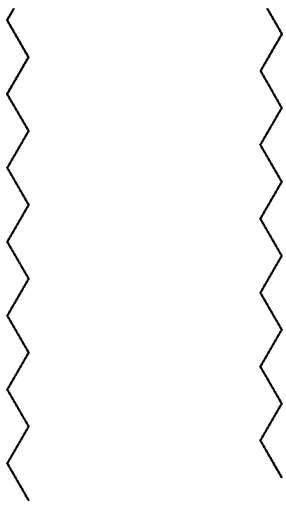
Polymer 8
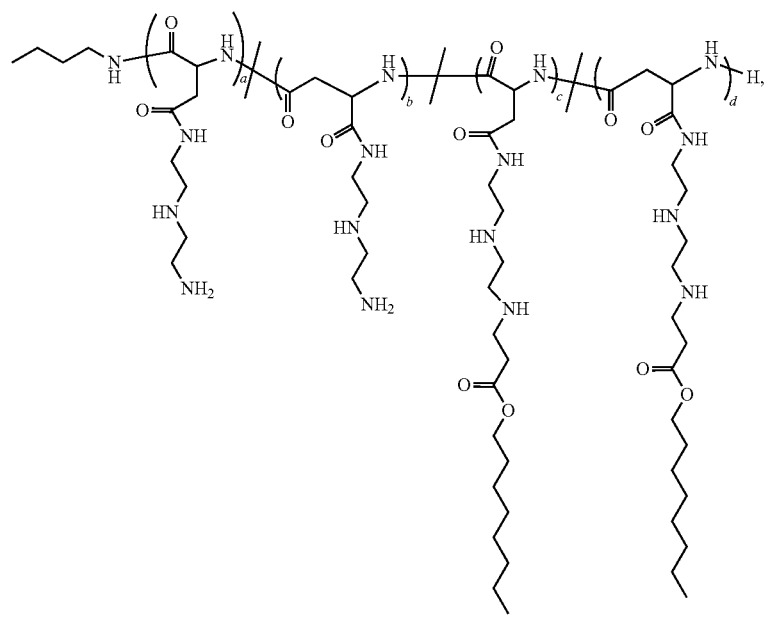
Polymer 9
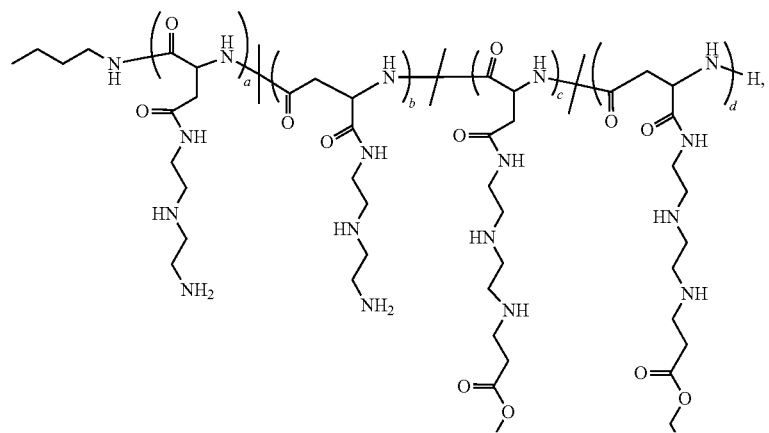

-continued
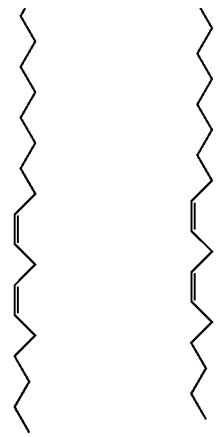
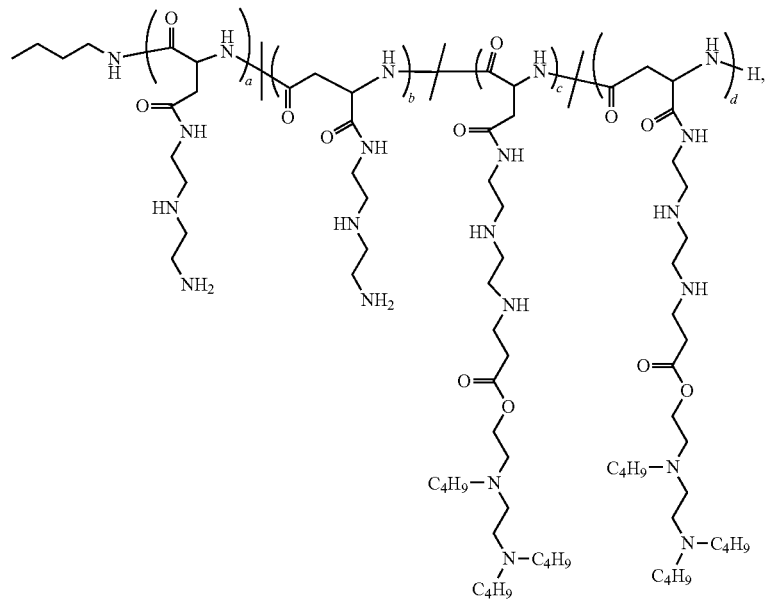
Polymer 10
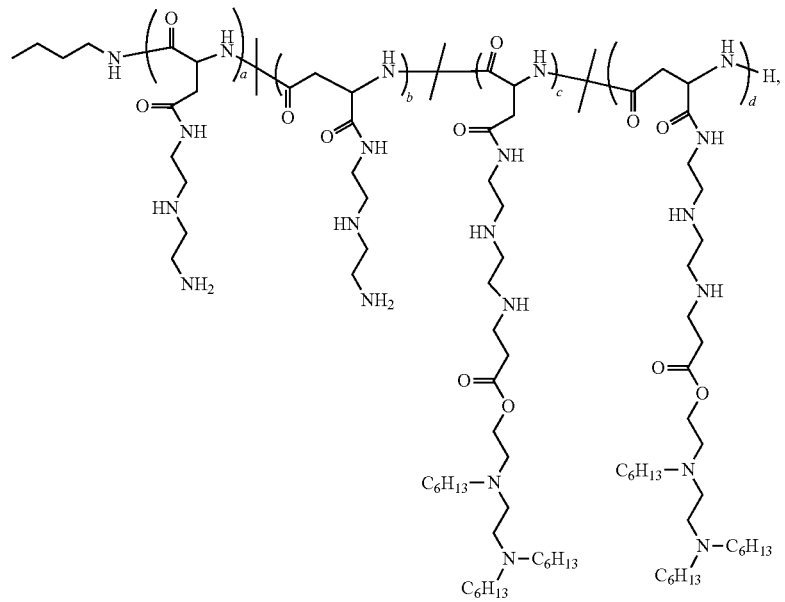
Polymer 11

Polymer 12
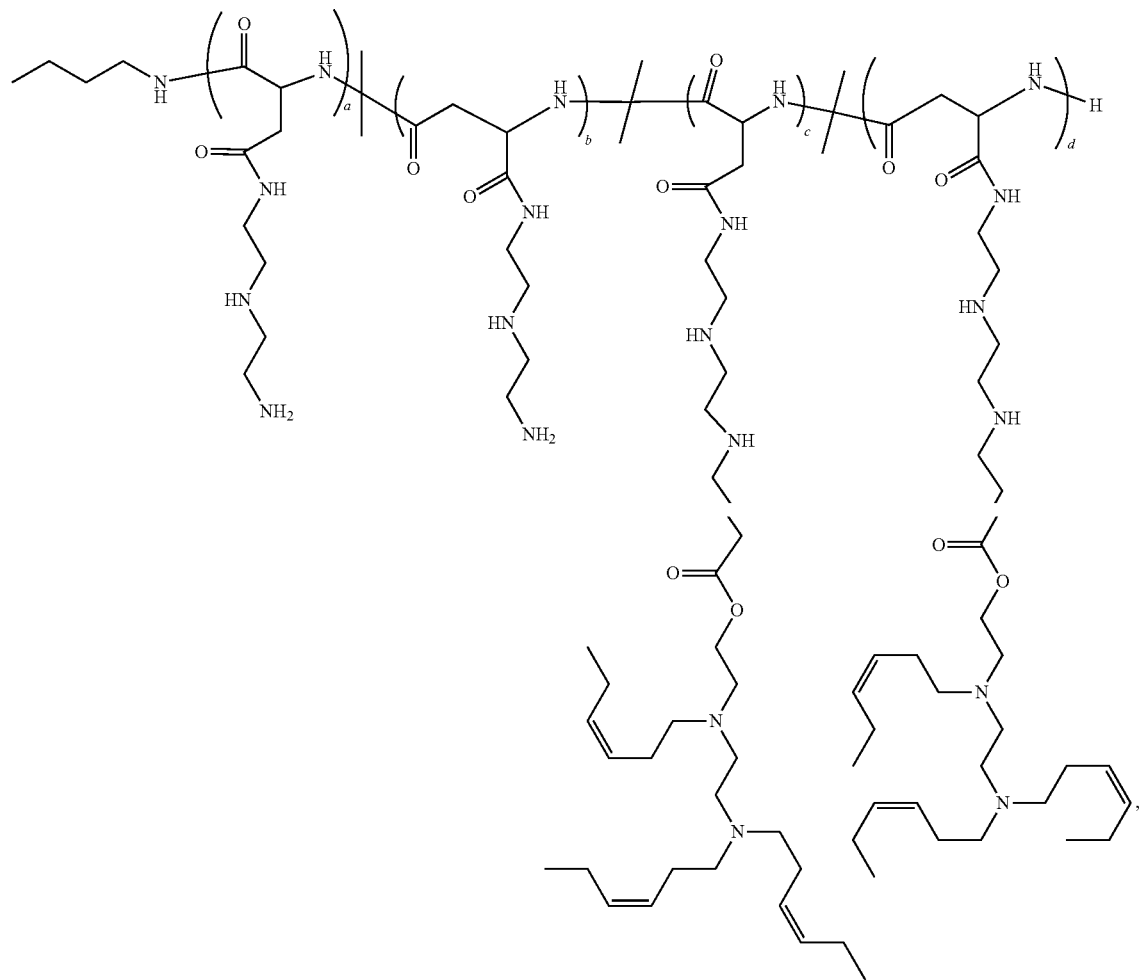
Polymer 13
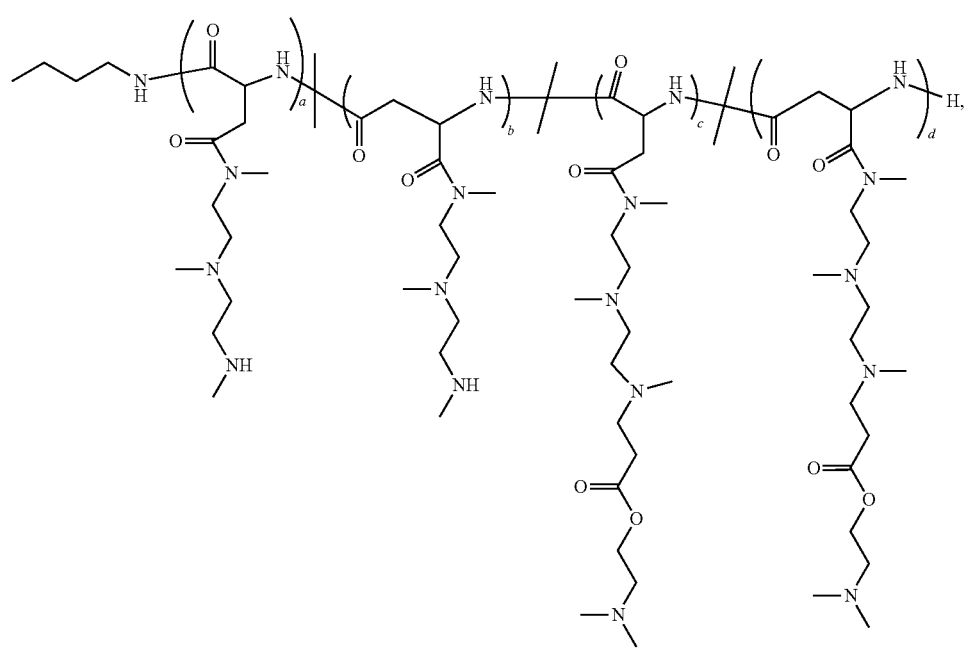

-continued
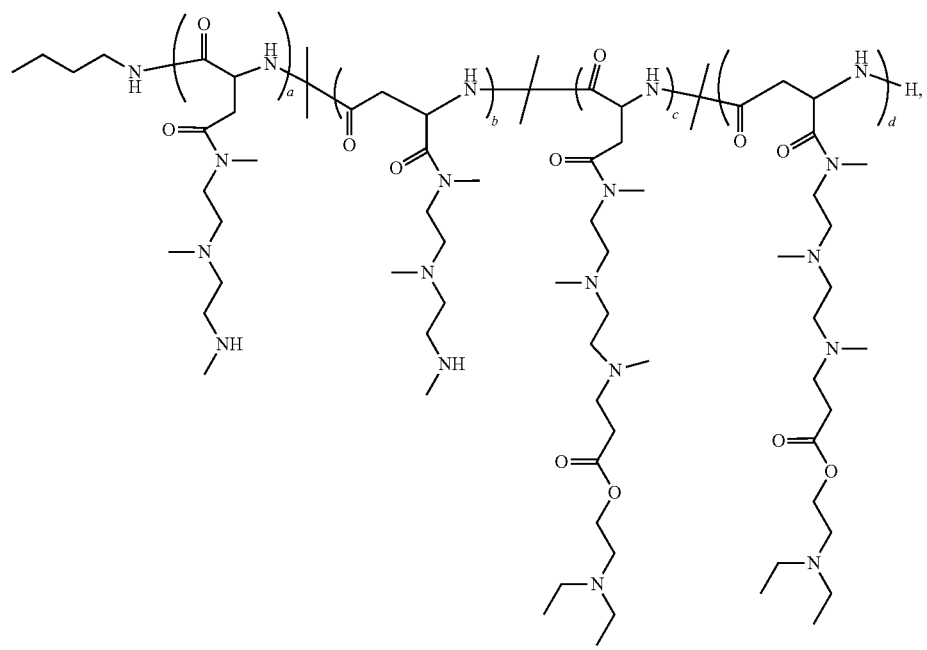
Polymer 14
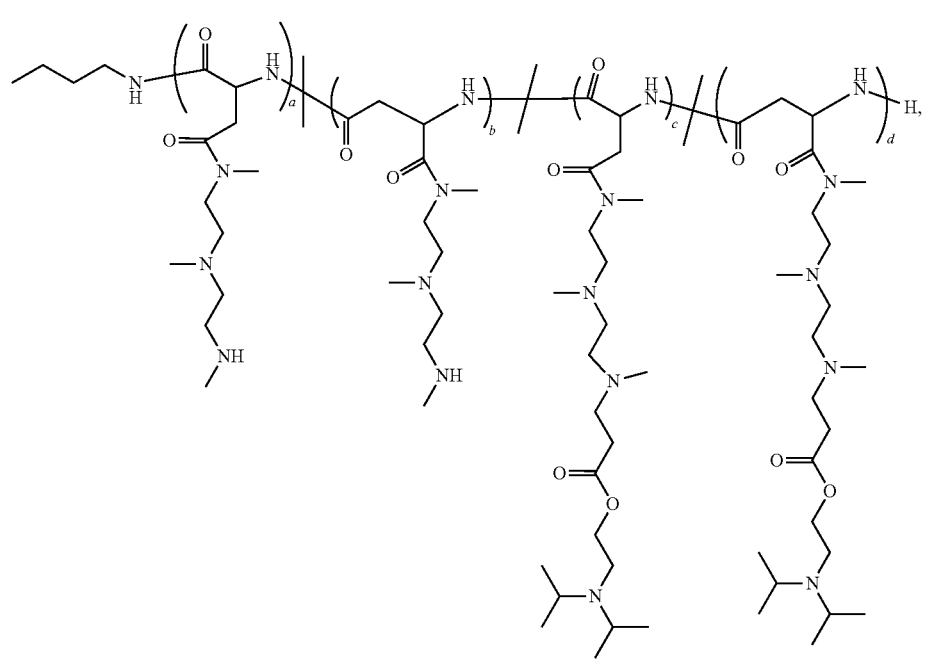
Polymer 15

Polymer 16
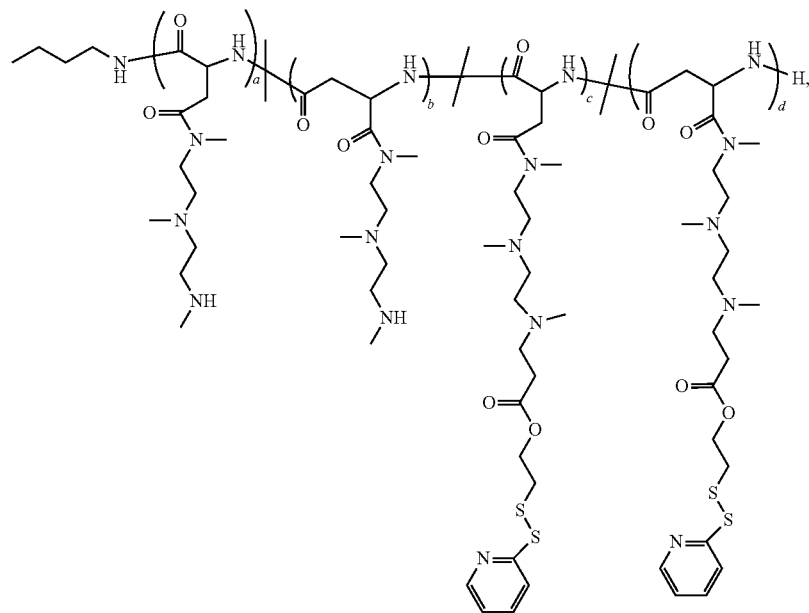
Polymer 17
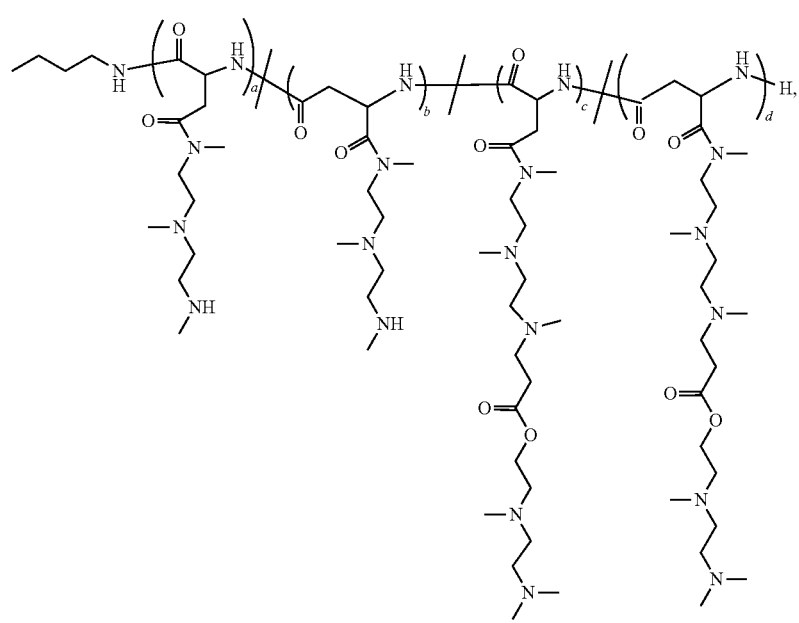

-continued
Polymer 18
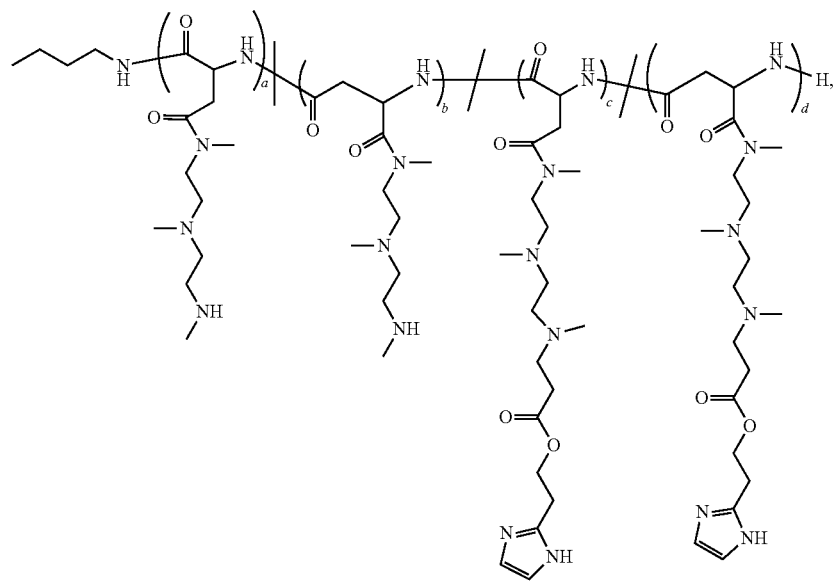
Polymer 19
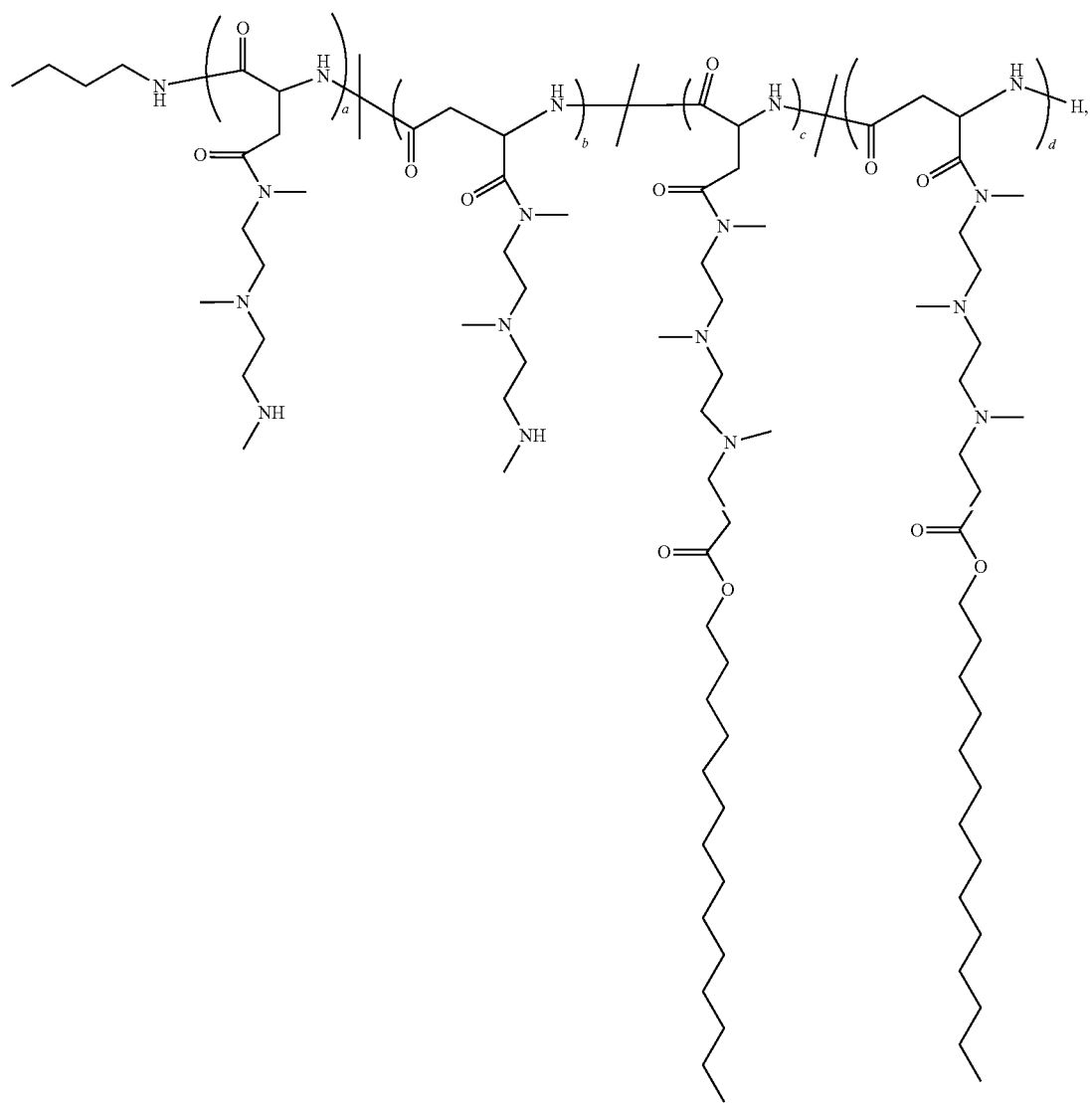

-continued
Polymer 20
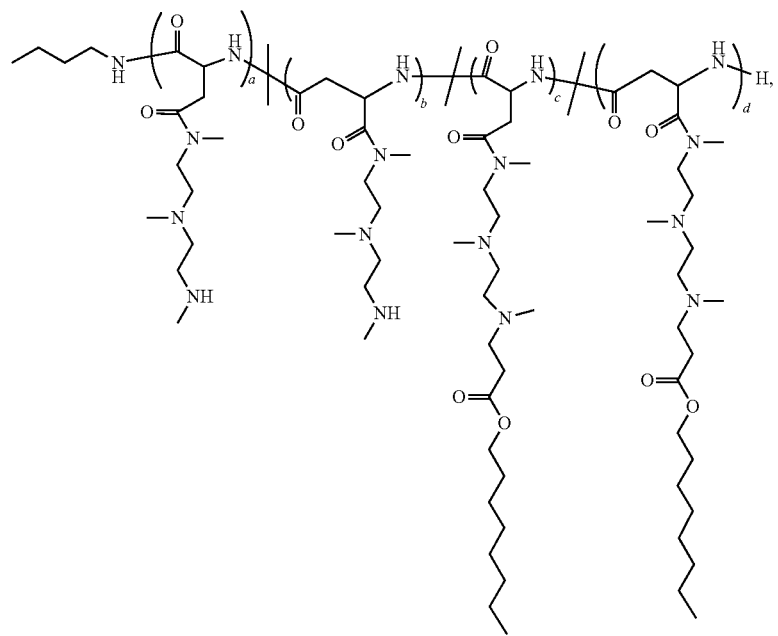
Polymer 21
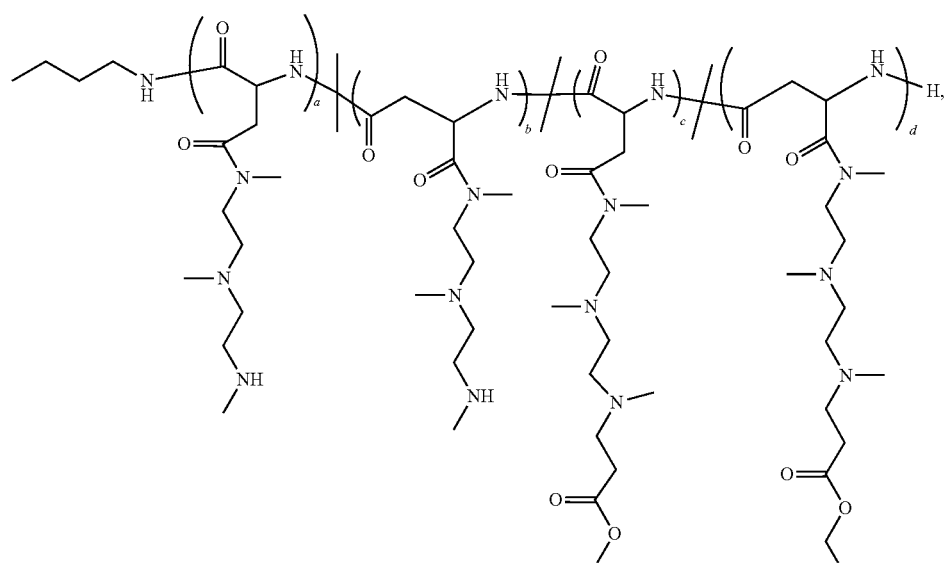

-continued
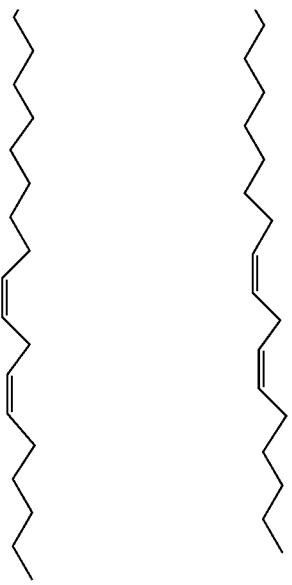
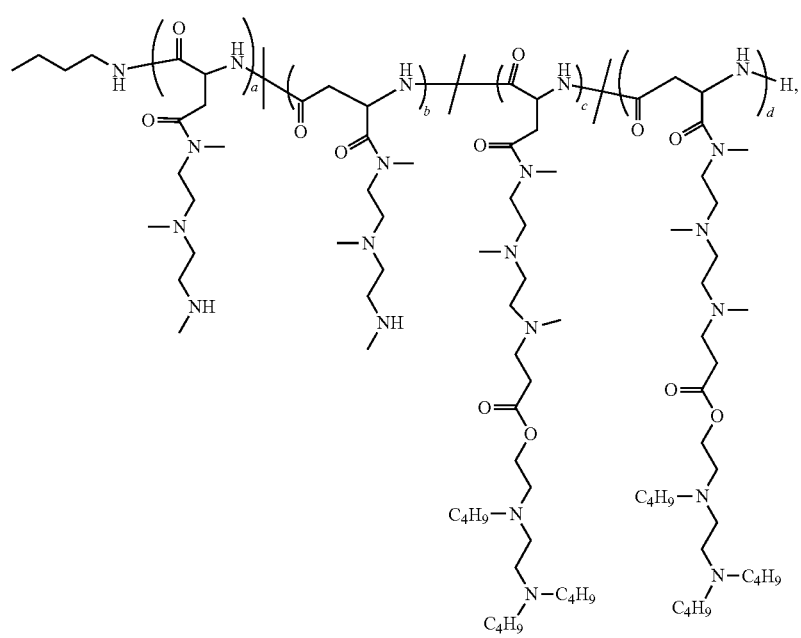
Polymer 22

-continued
Polymer 23
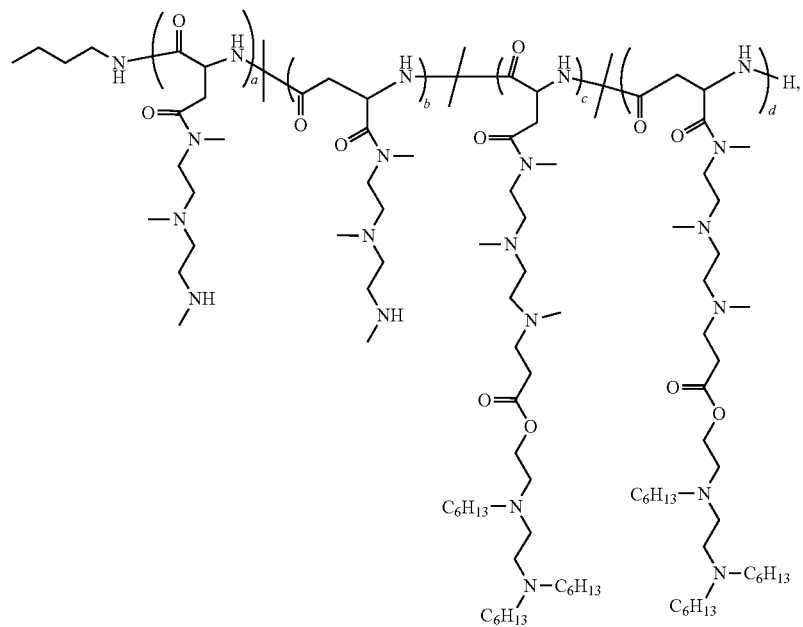
Polymer 24
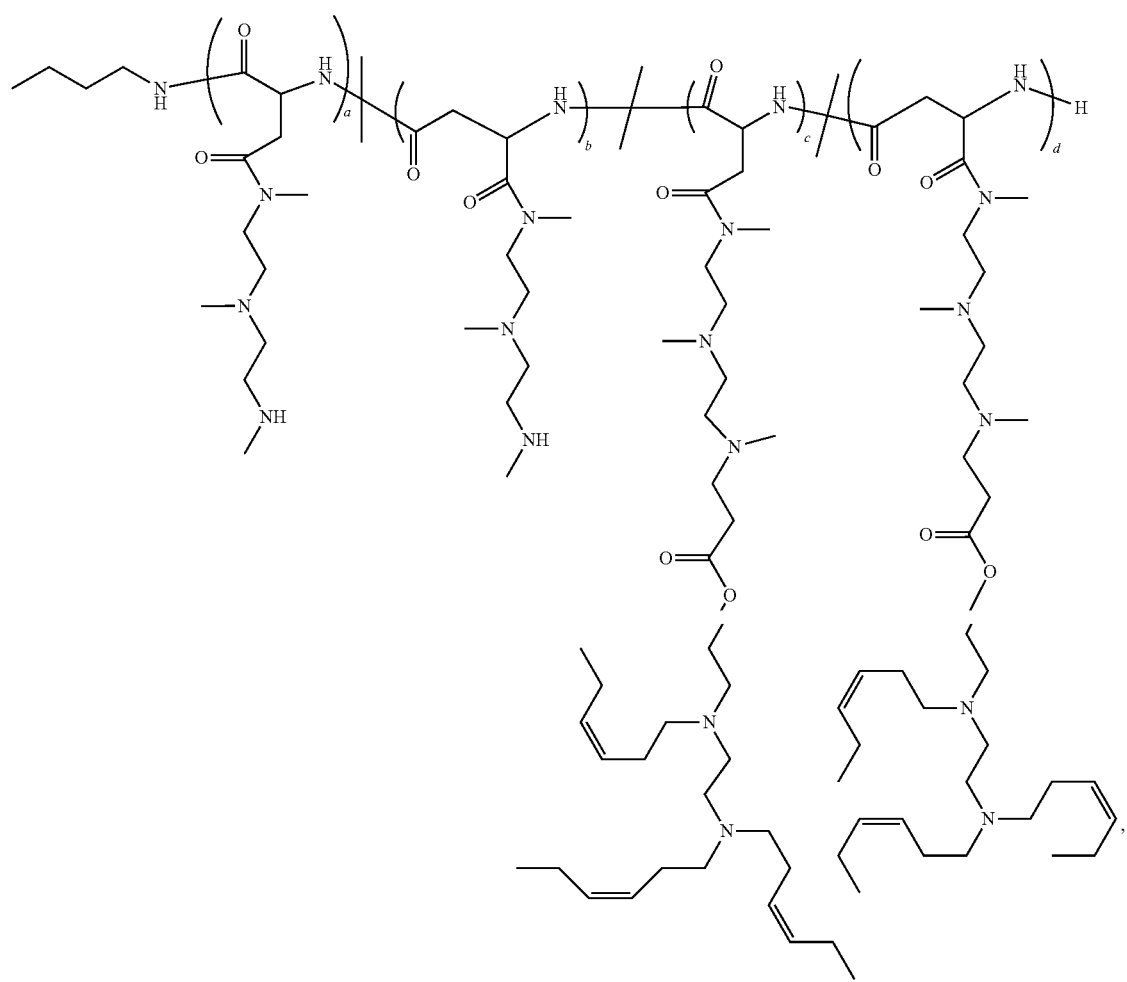

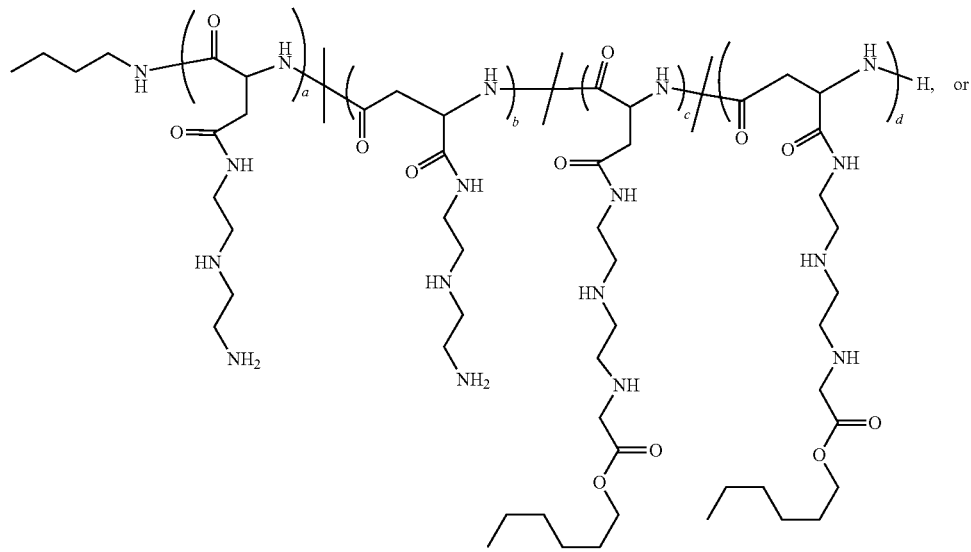

Polymer 28

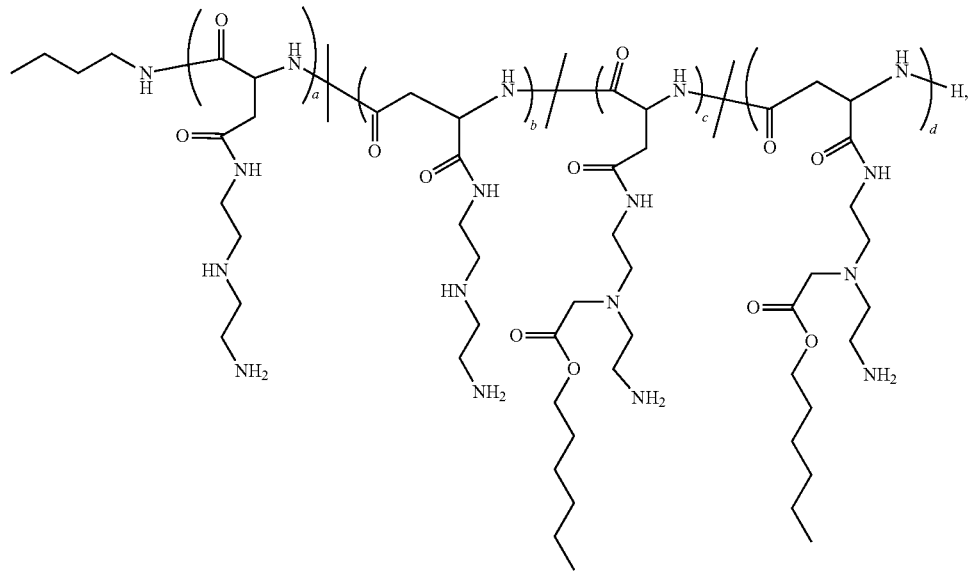

Polymer 29 wherein (a+b) is from about 0 to about 75 and (c+d) is from about 5 to about 80.

20. A composition comprising the polymer of claim 19 and a nucleic acid and/or polypeptide.

21. The composition of claim 20, wherein the composition comprises a guide nucleic acid and/or donor nucleic acid; an RNA-guided endonuclease or nucleic acid encoding same; or combination thereof.

22. The composition of claim 21, wherein the RNA-guided endonuclease is Cas9, Cpf1, or a combination thereof.

23. The composition of claim 20, wherein the composition comprises a DNA recombinase, a zinc finger nuclease, a transcription activator-like effector nuclease, or a combination thereof.

24. The composition of claim 20, wherein the composition comprises a nanoparticle comprising the polymer and the nucleic acid and/or polypeptide.

25. The composition of claim 20, wherein the composition comprises a second polymer that comprises polyethylene oxide.

26. A method of delivering a nucleic acid and/or polypeptide to a cell, the method comprising administering the composition of claim 20 to the cell.

27. The method of claim 26, wherein the cell is in a subject and the composition is administered to the subject, and wherein the polymer comprises a tissue-specific targeting moiety that localizes the polymer to tissues of a peripheral nervous system, a central nervous system, liver, muscle, lung, bone, or an eye of the subject.

28. The method of claim 27, wherein the polymer comprises a targeting moiety that preferentially binds to tumor cells.

* * * * *

SEQUENCE LISTING

<160> NUMBER OF SEQ ID NOS: 20

<210> SEQ ID NO 1
<211> LENGTH: 1368
<212> TYPE: PRT
<213> ORGANISM: Streptococcus pyogenes
<220> FEATURE:
<221> NAME/KEY: MISC_FEATURE
<222> LOCATION: (1)..(1368)
<223> OTHER INFORMATION: AKP81606.1

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765
```

```
Thr Thr Gln Lys Gly Gln Lys Asn Ser Arg Glu Arg Met Lys Arg Ile
    770             775                 780
Glu Glu Gly Ile Lys Glu Leu Gly Ser Gln Ile Leu Lys Glu His Pro
785             790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820              825                 830
Leu Ser Asp Tyr Asp Val Asp His Ile Val Pro Gln Ser Phe Leu Lys
        835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865             870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
```

-continued

```
                1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 2
<211> LENGTH: 2560
<212> TYPE: PRT
<213> ORGANISM: Francisella tularensis

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

```
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Ser Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
```

-continued

```
                595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
    1010                1015                1020
```

-continued

```
Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Met Ser Ile
1250                1255                1260

Tyr Gln Glu Phe Val Asn Lys Tyr Ser Leu Ser Lys Thr Leu Arg
1265                1270                1275

Phe Glu Leu Ile Pro Gln Gly Lys Thr Leu Glu Asn Ile Lys Ala
1280                1285                1290

Arg Gly Leu Ile Leu Asp Asp Glu Lys Arg Ala Lys Asp Tyr Lys
1295                1300                1305

Lys Ala Lys Gln Ile Ile Asp Lys Tyr His Gln Phe Phe Ile Glu
1310                1315                1320

Glu Ile Leu Ser Ser Val Cys Ile Ser Glu Asp Leu Leu Gln Asn
1325                1330                1335

Tyr Ser Asp Val Tyr Phe Lys Leu Lys Lys Ser Asp Asp Asp Asn
1340                1345                1350

Leu Gln Lys Asp Phe Lys Ser Ala Lys Asp Thr Ile Lys Lys Gln
1355                1360                1365

Ile Ser Glu Tyr Ile Lys Asp Ser Glu Lys Phe Lys Asn Leu Phe
1370                1375                1380

Asn Gln Asn Leu Ile Asp Ala Lys Lys Gly Gln Glu Ser Asp Leu
1385                1390                1395

Ile Leu Trp Leu Lys Gln Ser Lys Asp Asn Gly Ile Glu Leu Phe
1400                1405                1410
```

```
Lys Ala Asn Ser Asp Ile Thr Asp Ile Asp Glu Ala Leu Glu Ile
1415                1420                1425

Ile Lys Ser Phe Lys Gly Trp Thr Thr Tyr Phe Lys Gly Phe His
1430                1435                1440

Glu Asn Arg Lys Asn Val Tyr Ser Ser Asn Asp Ile Pro Thr Ser
1445                1450                1455

Ile Ile Tyr Arg Ile Val Asp Asp Asn Leu Pro Lys Phe Leu Glu
1460                1465                1470

Asn Lys Ala Lys Tyr Glu Ser Leu Lys Asp Lys Ala Pro Glu Ala
1475                1480                1485

Ile Asn Tyr Glu Gln Ile Lys Lys Asp Leu Ala Glu Glu Leu Thr
1490                1495                1500

Phe Asp Ile Asp Tyr Lys Thr Ser Glu Val Asn Gln Arg Val Phe
1505                1510                1515

Ser Leu Asp Glu Val Phe Glu Ile Ala Asn Phe Asn Asn Tyr Leu
1520                1525                1530

Asn Gln Ser Gly Ile Thr Lys Phe Asn Thr Ile Ile Gly Gly Lys
1535                1540                1545

Phe Val Asn Gly Glu Asn Thr Lys Arg Lys Gly Ile Asn Glu Tyr
1550                1555                1560

Ile Asn Leu Tyr Ser Gln Gln Ile Asn Asp Lys Thr Leu Lys Lys
1565                1570                1575

Tyr Lys Met Ser Val Leu Phe Lys Gln Ile Leu Ser Asp Thr Glu
1580                1585                1590

Ser Lys Ser Phe Val Ile Asp Lys Leu Glu Asp Asp Ser Asp Val
1595                1600                1605

Val Thr Thr Met Gln Ser Phe Tyr Glu Gln Ile Ala Ala Phe Lys
1610                1615                1620

Thr Val Glu Glu Lys Ser Ile Lys Glu Thr Leu Ser Leu Leu Phe
1625                1630                1635

Asp Asp Leu Lys Ala Gln Lys Leu Asp Leu Ser Lys Ile Tyr Phe
1640                1645                1650

Lys Asn Asp Lys Ser Leu Thr Asp Leu Ser Gln Gln Val Phe Asp
1655                1660                1665

Asp Tyr Ser Val Ile Gly Thr Ala Val Leu Glu Tyr Ile Thr Gln
1670                1675                1680

Gln Ile Ala Pro Lys Asn Leu Asp Asn Pro Ser Lys Lys Glu Gln
1685                1690                1695

Glu Leu Ile Ala Lys Lys Thr Glu Lys Ala Lys Tyr Leu Ser Leu
1700                1705                1710

Glu Thr Ile Lys Leu Ala Leu Glu Glu Phe Asn Lys His Arg Asp
1715                1720                1725

Ile Asp Lys Gln Cys Arg Phe Glu Glu Ile Leu Ala Asn Phe Ala
1730                1735                1740

Ala Ile Pro Met Ile Phe Asp Glu Ile Ala Gln Asn Lys Asp Asn
1745                1750                1755

Leu Ala Gln Ile Ser Ile Lys Tyr Gln Asn Gln Gly Lys Lys Asp
1760                1765                1770

Leu Leu Gln Ala Ser Ala Glu Asp Asp Val Lys Ala Ile Lys Asp
1775                1780                1785

Leu Leu Asp Gln Thr Asn Asn Leu Leu His Lys Leu Lys Ile Phe
1790                1795                1800

His Ile Ser Gln Ser Glu Asp Lys Ala Asn Ile Leu Asp Lys Asp
```

-continued

```
            1805                1810                1815

Glu His Phe Tyr Leu Val Phe Glu Glu Cys Tyr Phe Glu Leu Ala
            1820                1825                1830

Asn Ile Val Pro Leu Tyr Asn Lys Ile Arg Asn Tyr Ile Thr Gln
            1835                1840                1845

Lys Pro Tyr Ser Asp Glu Lys Phe Lys Leu Asn Phe Glu Asn Ser
            1850                1855                1860

Thr Leu Ala Asn Gly Trp Asp Lys Asn Lys Glu Pro Asp Asn Thr
            1865                1870                1875

Ala Ile Leu Phe Ile Lys Asp Asp Lys Tyr Tyr Leu Gly Val Met
            1880                1885                1890

Asn Lys Lys Asn Asn Lys Ile Phe Asp Asp Lys Ala Ile Lys Glu
            1895                1900                1905

Asn Lys Gly Glu Gly Tyr Lys Lys Ile Val Tyr Lys Leu Leu Pro
            1910                1915                1920

Gly Ala Asn Lys Met Leu Pro Lys Val Phe Phe Ser Ala Lys Ser
            1925                1930                1935

Ile Lys Phe Tyr Asn Pro Ser Glu Asp Ile Leu Arg Ile Arg Asn
            1940                1945                1950

His Ser Thr His Thr Lys Asn Gly Ser Pro Gln Lys Gly Tyr Glu
            1955                1960                1965

Lys Phe Glu Phe Asn Ile Glu Asp Cys Arg Lys Phe Ile Asp Phe
            1970                1975                1980

Tyr Lys Gln Ser Ile Ser Lys His Pro Glu Trp Lys Asp Phe Gly
            1985                1990                1995

Phe Arg Phe Ser Asp Thr Gln Arg Tyr Asn Ser Ile Asp Glu Phe
            2000                2005                2010

Tyr Arg Glu Val Glu Asn Gln Gly Tyr Lys Leu Thr Phe Glu Asn
            2015                2020                2025

Ile Ser Glu Ser Tyr Ile Asp Ser Val Val Asn Gln Gly Lys Leu
            2030                2035                2040

Tyr Leu Phe Gln Ile Tyr Asn Lys Asp Phe Ser Ala Tyr Ser Lys
            2045                2050                2055

Gly Arg Pro Asn Leu His Thr Leu Tyr Trp Lys Ala Leu Phe Asp
            2060                2065                2070

Glu Arg Asn Leu Gln Asp Val Val Tyr Lys Leu Asn Gly Glu Ala
            2075                2080                2085

Glu Leu Phe Tyr Arg Lys Gln Ser Ile Pro Lys Lys Ile Thr His
            2090                2095                2100

Pro Ala Lys Glu Ala Ile Ala Asn Lys Asn Lys Asp Asn Pro Lys
            2105                2110                2115

Lys Glu Ser Val Phe Glu Tyr Asp Leu Ile Lys Asp Lys Arg Phe
            2120                2125                2130

Thr Glu Asp Lys Phe Phe Phe His Cys Pro Ile Thr Ile Asn Phe
            2135                2140                2145

Lys Ser Ser Gly Ala Asn Lys Phe Asn Asp Glu Ile Asn Leu Leu
            2150                2155                2160

Leu Lys Glu Lys Ala Asn Asp Val His Ile Leu Ser Ile Asp Arg
            2165                2170                2175

Gly Glu Arg His Leu Ala Tyr Tyr Thr Leu Val Asp Gly Lys Gly
            2180                2185                2190

Asn Ile Ile Lys Gln Asp Thr Phe Asn Ile Ile Gly Asn Asp Arg
            2195                2200                2205
```

```
Met Lys Thr Asn Tyr His Asp Lys Leu Ala Ala Ile Glu Lys Asp
2210                2215                2220

Arg Asp Ser Ala Arg Lys Asp Trp Lys Ile Asn Asn Ile Lys
2225                2230                2235

Glu Met Lys Glu Gly Tyr Leu Ser Gln Val Val His Glu Ile Ala
2240                2245                2250

Lys Leu Val Ile Glu Tyr Asn Ala Ile Val Val Phe Glu Asp Leu
2255                2260                2265

Asn Phe Gly Phe Lys Arg Gly Arg Phe Lys Val Glu Lys Gln Val
2270                2275                2280

Tyr Gln Lys Leu Glu Lys Met Leu Ile Glu Lys Leu Asn Tyr Leu
2285                2290                2295

Val Phe Lys Asp Asn Glu Phe Asp Lys Thr Gly Gly Val Leu Arg
2300                2305                2310

Ala Tyr Gln Leu Thr Ala Pro Phe Glu Thr Phe Lys Lys Met Gly
2315                2320                2325

Lys Gln Thr Gly Ile Ile Tyr Tyr Val Pro Ala Gly Phe Thr Ser
2330                2335                2340

Lys Ile Cys Pro Val Thr Gly Phe Val Asn Gln Leu Tyr Pro Lys
2345                2350                2355

Tyr Glu Ser Val Ser Lys Ser Gln Glu Phe Phe Ser Lys Phe Asp
2360                2365                2370

Lys Ile Cys Tyr Asn Leu Asp Lys Gly Tyr Phe Glu Phe Ser Phe
2375                2380                2385

Asp Tyr Lys Asn Phe Gly Asp Lys Ala Ala Lys Gly Lys Trp Thr
2390                2395                2400

Ile Ala Ser Phe Gly Ser Arg Leu Ile Asn Phe Arg Asn Ser Asp
2405                2410                2415

Lys Asn His Asn Trp Asp Thr Arg Glu Val Tyr Pro Thr Lys Glu
2420                2425                2430

Leu Glu Lys Leu Leu Lys Asp Tyr Ser Ile Glu Tyr Gly His Gly
2435                2440                2445

Glu Cys Ile Lys Ala Ala Ile Cys Gly Glu Ser Asp Lys Lys Phe
2450                2455                2460

Phe Ala Lys Leu Thr Ser Val Leu Asn Thr Ile Leu Gln Met Arg
2465                2470                2475

Asn Ser Lys Thr Gly Thr Glu Leu Asp Tyr Leu Ile Ser Pro Val
2480                2485                2490

Ala Asp Val Asn Gly Asn Phe Phe Asp Ser Arg Gln Ala Pro Lys
2495                2500                2505

Asn Met Pro Gln Asp Ala Asp Ala Asn Gly Ala Tyr His Ile Gly
2510                2515                2520

Leu Lys Gly Leu Met Leu Leu Gly Arg Ile Lys Asn Asn Gln Glu
2525                2530                2535

Gly Lys Lys Leu Asn Leu Val Ile Lys Asn Glu Glu Tyr Phe Glu
2540                2545                2550

Phe Val Gln Asn Arg Asn Asn
2555                2560

<210> SEQ ID NO 3
<211> LENGTH: 15
<212> TYPE: PRT
<213> ORGANISM: Artificial Sequence
<220> FEATURE:
```

```
<223> OTHER INFORMATION: Synthetic

<400> SEQUENCE: 3

Ile Gly Leu Asp Ile Gly Thr Asn Ser Val Gly Trp Ala Val Ile
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 4

Ile Val Ile Glu Met Ala Arg Glu
1               5

<210> SEQ ID NO 5
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 5

Asp Val Asp His Ile Val Pro Gln Ser Phe Leu Lys Asp Asp Ser Ile
1               5                   10                  15

Asp Asn Lys Val Leu Thr Arg Ser Asp Lys Asn
            20                  25

<210> SEQ ID NO 6
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 6

His His Ala His Asp Ala Tyr Leu
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 7

Tyr Gly Arg Lys Lys Arg Arg Gln Arg Arg Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 8

Arg Arg Gln Arg Arg Thr Ser Lys Leu Met Lys Arg
1               5                   10

<210> SEQ ID NO 9
<211> LENGTH: 27
<212> TYPE: PRT
```

```
<213> ORGANISM: Artificial Sequence
<220> FEATURE:
<223> OTHER INFORMATION: Synthetic Sequence

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 10

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 11
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 12

Tyr Gly Arg Lys Lys Arg Arg Gln Arg Arg Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 13

Arg Lys Lys Arg Arg Gln Arg Arg Arg
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 14
```

Tyr Gly Arg Lys Lys Arg Arg Gln Arg Arg
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 15

Arg Lys Lys Arg Arg Gln Arg Arg
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 16

Tyr Ala Arg Ala Ala Ala Arg Gln Ala Arg Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 17

Thr His Arg Leu Pro Arg Arg Arg Arg Arg
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 18

Gly Gly Arg Arg Ala Arg Arg Arg Arg Arg
1               5                   10

<210> SEQ ID NO 19
<211> LENGTH: 1307
<212> TYPE: PRT
<213> ORGANISM: Artificial Sequence
<220> FEATURE:
<223> OTHER INFORMATION: Synthetic Sequence

<400> SEQUENCE: 19

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

```
Asp Ser Tyr Arg Lys Glu Lys Thr Glu Thr Arg Asn Ala Leu Ile
                85                  90                  95

Glu Glu Gln Ala Thr Tyr Arg Asn Ala Ile His Asp Tyr Phe Ile Gly
               100                 105                 110

Arg Thr Asp Asn Leu Thr Asp Ala Ile Asn Lys Arg His Ala Glu Ile
               115                 120                 125

Tyr Lys Gly Leu Phe Lys Ala Glu Leu Phe Asn Gly Lys Val Leu Lys
    130                 135                 140

Gln Leu Gly Thr Val Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
    275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495
```

```
Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Pro Tyr Ser Val
        515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
        610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
        690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
        820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
```

```
                915                 920                 925
Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr  Gly Ile Ala Glu
        995                 1000                1005

Lys Ala  Val Tyr Gln Gln  Phe Glu Lys Met  Leu Ile  Asp Lys Leu
    1010                1015                1020

Asn Cys  Leu Val Leu Lys  Asp Tyr Pro Ala  Glu Lys  Val Gly Gly
    1025                1030                1035

Val Leu  Asn Pro Tyr Gln  Leu Thr Asp Gln  Phe Thr  Ser Phe Ala
    1040                1045                1050

Lys Met  Gly Thr Gln Ser  Gly Phe Leu Phe  Tyr Val  Pro Ala Pro
    1055                1060                1065

Tyr Thr  Ser Lys Ile Asp  Pro Leu Thr Gly  Phe Val  Asp Pro Phe
    1070                1075                1080

Val Trp  Lys Thr Ile Lys  Asn His Glu Ser  Arg Lys  His Phe Leu
    1085                1090                1095

Glu Gly  Phe Asp Phe Leu  His Tyr Asp Val  Lys Thr  Gly Asp Phe
    1100                1105                1110

Ile Leu  His Phe Lys Met  Asn Arg Asn Leu  Ser Phe  Gln Arg Gly
    1115                1120                1125

Leu Pro  Gly Phe Met Pro  Ala Trp Asp Ile  Val Phe  Glu Lys Asn
    1130                1135                1140

Glu Thr  Gln Phe Asp Ala  Lys Gly Thr Pro  Phe Ile  Ala Gly Lys
    1145                1150                1155

Arg Ile  Val Pro Val Ile  Glu Asn His Arg  Phe Thr  Gly Arg Tyr
    1160                1165                1170

Arg Asp  Leu Tyr Pro Ala  Asn Glu Leu Ile  Ala Leu  Leu Glu Glu
    1175                1180                1185

Lys Gly  Ile Val Phe Arg  Asp Gly Ser Asn  Ile Leu  Pro Lys Leu
    1190                1195                1200

Leu Glu  Asn Asp Asp Ser  His Ala Ile Asp  Thr Met  Val Ala Leu
    1205                1210                1215

Ile Arg  Ser Val Leu Gln  Met Arg Asn Ser  Asn Ala  Ala Thr Gly
    1220                1225                1230

Glu Asp  Tyr Ile Asn Ser  Pro Val Arg Asp  Leu Asn  Gly Val Cys
    1235                1240                1245

Phe Asp  Ser Arg Phe Gln  Asn Pro Glu Trp  Pro Met  Asp Ala Asp
    1250                1255                1260

Ala Asn  Gly Ala Tyr His  Ile Ala Leu Lys  Gly Gln  Leu Leu Leu
    1265                1270                1275

Asn His  Leu Lys Glu Ser  Lys Asp Leu Lys  Leu Gln  Asn Gly Ile
    1280                1285                1290

Ser Asn  Gln Asp Trp Leu  Ala Tyr Ile Gln  Glu Leu  Arg Asn
    1295                1300                1305

<210> SEQ ID NO 20
```

```
<211> LENGTH: 1228
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (559)..(559)
<223> OTHER INFORMATION: Xaa can be any naturally occurring amino acid
<220> FEATURE:
<221> NAME/KEY: misc_feature
<222> LOCATION: (593)..(593)
<223> OTHER INFORMATION: Xaa can be any naturally occurring amino acid
<220> FEATURE:
<221> NAME/KEY: misc_feature
<222> LOCATION: (604)..(604)
<223> OTHER INFORMATION: Xaa can be any naturally occurring amino acid
<220> FEATURE:
<221> NAME/KEY: misc_feature
<222> LOCATION: (627)..(627)
<223> OTHER INFORMATION: Xaa can be any naturally occurring amino acid
<220> FEATURE:
<221> NAME/KEY: misc_feature
<222> LOCATION: (702)..(702)
<223> OTHER INFORMATION: Xaa can be any naturally occurring amino acid
<220> FEATURE:
<221> NAME/KEY: misc_feature
<222> LOCATION: (723)..(723)
<223> OTHER INFORMATION: Xaa can be any naturally occurring amino acid
<220> FEATURE:
<221> NAME/KEY: misc_feature
<222> LOCATION: (747)..(747)
<223> OTHER INFORMATION: Xaa can be any naturally occurring amino acid
<220> FEATURE:
<221> NAME/KEY: misc_feature
<222> LOCATION: (950)..(950)
<223> OTHER INFORMATION: Xaa can be any naturally occurring amino acid
<220> FEATURE:
<221> NAME/KEY: misc_feature
<222> LOCATION: (958)..(958)
<223> OTHER INFORMATION: Xaa can be any naturally occurring amino acid
<220> FEATURE:
<221> NAME/KEY: misc_feature
<222> LOCATION: (987)..(987)
<223> OTHER INFORMATION: Xaa can be any naturally occurring amino acid
<220> FEATURE:
<221> NAME/KEY: misc_feature
<222> LOCATION: (1036)..(1036)
<223> OTHER INFORMATION: Xaa can be any naturally occurring amino acid
<220> FEATURE:
<221> NAME/KEY: misc_feature
<222> LOCATION: (1129)..(1129)
<223> OTHER INFORMATION: Xaa can be any naturally occurring amino acid
<220> FEATURE:
<221> NAME/KEY: misc_feature
<222> LOCATION: (1132)..(1132)
<223> OTHER INFORMATION: Xaa can be any naturally occurring amino acid
<220> FEATURE:
<221> NAME/KEY: misc_feature
<222> LOCATION: (1135)..(1135)
<223> OTHER INFORMATION: Xaa can be any naturally occurring amino acid
<220> FEATURE:
<221> NAME/KEY: misc_feature
```

<222> LOCATION: (1138)..(1138)
<223> OTHER INFORMATION: Xaa can be any naturally occurring amino acid

<400> SEQUENCE: 20

```
Ala Ala Ser Lys Leu Glu Lys Phe Thr Asn Cys Tyr Ser Leu Ser Lys
1               5                   10                  15

Thr Leu Arg Phe Lys Ala Ile Pro Val Gly Lys Thr Gln Glu Asn Ile
            20                  25                  30

Asp Asn Lys Arg Leu Leu Val Glu Asp Glu Lys Arg Ala Glu Asp Tyr
        35                  40                  45

Lys Gly Val Lys Lys Leu Leu Asp Arg Tyr Tyr Leu Ser Phe Ile Asn
    50                  55                  60

Asp Val Leu His Ser Ile Lys Leu Lys Asn Leu Asn Asn Tyr Ile Ser
65                  70                  75                  80

Leu Phe Arg Lys Lys Thr Arg Thr Glu Lys Glu Asn Lys Glu Leu Glu
                85                  90                  95

Asn Leu Glu Ile Asn Leu Arg Lys Glu Ile Ala Lys Ala Phe Lys Gly
            100                 105                 110

Ala Ala Gly Tyr Lys Ser Leu Phe Lys Lys Asp Ile Ile Glu Thr Ile
        115                 120                 125

Leu Pro Glu Ala Ala Asp Asp Lys Asp Glu Ile Ala Leu Val Asn Ser
    130                 135                 140

Phe Asn Gly Phe Thr Thr Ala Phe Thr Gly Phe Phe Asp Asn Arg Glu
145                 150                 155                 160

Asn Xaa Phe Ser Glu Glu Ala Lys Ser Thr Ser Ile Ala Phe Arg Cys
                165                 170                 175

Ile Asn Glu Asn Leu Thr Arg Tyr Ile Ser Asn Xaa Asp Ile Phe Glu
            180                 185                 190

Lys Val Asp Ala Ile Phe Asp Lys His Glu Val Gln Glu Ile Lys Glu
        195                 200                 205

Lys Ile Leu Asn Ser Asp Tyr Asp Val Glu Asp Phe Phe Glu Gly Glu
    210                 215                 220

Phe Phe Asn Phe Val Leu Thr Gln Glu Gly Ile Asp Val Tyr Asn Ala
225                 230                 235                 240

Ile Ile Gly Gly Phe Val Thr Glu Ser Gly Glu Lys Ile Lys Gly Leu
                245                 250                 255

Asn Glu Tyr Ile Asn Leu Tyr Asn Ala Lys Thr Lys Gln Ala Leu Pro
            260                 265                 270

Lys Phe Lys Pro Leu Tyr Lys Gln Val Leu Ser Asp Arg Glu Ser Leu
        275                 280                 285

Ser Phe Tyr Gly Glu Gly Tyr Thr Ser Asp Glu Glu Val Leu Glu Val
    290                 295                 300

Phe Arg Asn Thr Leu Asn Lys Asn Ser Glu Ile Phe Ser Ser Ile Lys
305                 310                 315                 320

Lys Leu Glu Lys Leu Phe Lys Asn Phe Asp Glu Tyr Ser Ser Ala Gly
                325                 330                 335

Ile Phe Val Lys Asn Gly Pro Ala Ile Ser Thr Ile Ser Lys Asp Ile
            340                 345                 350

Phe Gly Glu Trp Asn Leu Ile Arg Asp Lys Trp Asn Ala Glu Tyr Asp
        355                 360                 365

Asp Ile His Leu Lys Lys Lys Ala Val Val Thr Glu Lys Tyr Glu Asp
    370                 375                 380

Asp Arg Arg Lys Ser Phe Lys Lys Ile Gly Ser Phe Ser Leu Glu Gln
385                 390                 395                 400
```

```
Leu Gln Glu Tyr Ala Asp Ala Asp Leu Ser Val Val Glu Lys Leu Lys
                405                 410                 415

Glu Ile Ile Ile Gln Lys Val Asp Glu Ile Tyr Lys Val Tyr Gly Ser
            420                 425                 430

Ser Glu Lys Leu Phe Asp Ala Asp Phe Val Leu Glu Lys Ser Leu Lys
        435                 440                 445

Lys Asn Asp Ala Val Val Ala Ile Xaa Lys Asp Leu Leu Asp Ser Val
    450                 455                 460

Lys Ser Phe Glu Asn Tyr Ile Lys Ala Phe Phe Gly Glu Gly Lys Glu
465                 470                 475                 480

Thr Asn Arg Asp Glu Ser Phe Tyr Gly Asp Phe Val Leu Ala Tyr Asp
                485                 490                 495

Ile Leu Leu Lys Val Asp His Ile Tyr Asp Ala Ile Arg Asn Tyr Val
            500                 505                 510

Thr Gln Lys Pro Tyr Ser Lys Asp Lys Phe Lys Leu Tyr Phe Gln Asn
        515                 520                 525

Pro Gln Phe Xaa Gly Gly Trp Asp Lys Asp Lys Glu Thr Asp Tyr Arg
    530                 535                 540

Ala Thr Ile Leu Arg Tyr Gly Ser Lys Tyr Tyr Leu Ala Ile Xaa Asp
545                 550                 555                 560

Lys Lys Tyr Ala Lys Cys Leu Gln Lys Ile Asp Lys Asp Asp Val Asn
                565                 570                 575

Gly Asn Tyr Glu Lys Ile Asn Tyr Lys Leu Leu Pro Gly Pro Asn Lys
            580                 585                 590

Xaa Leu Pro Lys Val Phe Phe Ser Lys Lys Trp Xaa Ala Tyr Tyr Asn
        595                 600                 605

Pro Ser Glu Asp Ile Gln Lys Ile Tyr Lys Asn Gly Thr Phe Lys Lys
    610                 615                 620

Gly Asp Xaa Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
            660                 665                 670

Glu Val Glu Glu Gln Gly Tyr Lys Val Ser Phe Glu Ser Ala Ser Lys
        675                 680                 685

Lys Glu Val Asp Lys Leu Val Glu Glu Gly Lys Leu Tyr Xaa Phe Gln
    690                 695                 700

Ile Tyr Asn Lys Asp Phe Ser Asp Lys Ser His Gly Thr Pro Asn Leu
705                 710                 715                 720

His Thr Xaa Tyr Phe Lys Leu Leu Phe Asp Glu Asn Asn His Gly Gln
                725                 730                 735

Ile Arg Leu Ser Gly Gly Ala Glu Leu Phe Xaa Arg Arg Ala Ser Leu
            740                 745                 750

Lys Lys Glu Glu Leu Val Val His Pro Ala Asn Ser Pro Ile Ala Asn
        755                 760                 765

Lys Asn Pro Asp Asn Pro Lys Lys Thr Thr Thr Leu Ser Tyr Asp Val
    770                 775                 780

Tyr Lys Asp Lys Arg Phe Ser Glu Asp Gln Tyr Glu Leu His Ile Pro
785                 790                 795                 800

Ile Ala Ile Asn Lys Cys Pro Lys Asn Ile Phe Lys Ile Asn Thr Glu
                805                 810                 815
```

```
Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Asp Gly Lys
        835                 840                 845

Gly Asn Ile Val Glu Gln Tyr Ser Leu Asn Glu Ile Ile Asn Asn Phe
850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
            885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
            915                 920                 925

Asn Ser Gly Phe Lys Asn Ser Arg Val Lys Val Glu Lys Gln Val Tyr
            930                 935                 940

Gln Lys Phe Glu Lys Xaa Leu Ile Asp Lys Leu Asn Tyr Xaa Val Asp
945                 950                 955                 960

Lys Lys Ser Asn Pro Cys Ala Thr Gly Gly Ala Leu Lys Gly Tyr Gln
            965                 970                 975

Ile Thr Asn Lys Phe Glu Ser Phe Lys Ser Xaa Ser Thr Gln Asn Gly
            980                 985                 990

Phe Ile Phe Tyr Ile Pro Ala Trp Leu Thr Ser Lys Ile Asp Pro Ser
            995                 1000                1005

Thr Gly Phe Val Asn Leu Leu Lys Thr Lys Tyr Thr Ser Ile Ala
    1010                1015                1020

Asp Ser Lys Lys Phe Ile Ser Ser Phe Asp Arg Ile Xaa Tyr Val
    1025                1030                1035

Pro Glu Glu Asp Leu Phe Glu Phe Ala Leu Asp Tyr Lys Asn Phe
    1040                1045                1050

Ser Arg Thr Asp Ala Asp Tyr Ile Lys Lys Trp Lys Leu Tyr Ser
    1055                1060                1065

Tyr Gly Asn Arg Ile Arg Ile Phe Ala Ala Ala Lys Lys Asn Asn
    1070                1075                1080

Val Phe Ala Trp Glu Glu Val Cys Leu Thr Ser Ala Tyr Lys Glu
    1085                1090                1095

Leu Phe Asn Lys Tyr Gly Ile Asn Tyr Gln Gln Gly Asp Ile Arg
    1100                1105                1110

Ala Leu Leu Cys Glu Gln Ser Asp Lys Ala Phe Tyr Ser Ser Phe
    1115                1120                1125

Xaa Ala Leu Xaa Ser Leu Xaa Leu Gln Xaa Arg Asn Ser Ile Thr
    1130                1135                1140

Gly Arg Thr Asp Val Asp Phe Leu Ile Ser Pro Val Lys Asn Ser
    1145                1150                1155

Asp Gly Ile Phe Tyr Asp Ser Arg Asn Tyr Glu Ala Gln Glu Asn
    1160                1165                1170

Ala Ile Leu Pro Lys Asn Ala Asp Ala Asn Gly Ala Tyr Asn Ile
    1175                1180                1185

Ala Arg Lys Val Leu Trp Ala Ile Gly Gln Phe Lys Lys Ala Glu
    1190                1195                1200
```

-continued

```
Asp Glu Lys Leu Asp Lys Val Lys Ile Ala Ile Ser Asn Lys Glu
    1205                1210                1215

Trp Leu Glu Tyr Ala Gln Thr Ser Val Lys
    1220                1225
```